US009150887B2

(12) United States Patent
Miller et al.

(10) Patent No.: US 9,150,887 B2
(45) Date of Patent: *Oct. 6, 2015

(54) ETHANOLOGENIC BACTERIA WITH INCREASED RESISTANCE TO FURFURAL

(75) Inventors: Elliot Norman Miller, Gainesville, FL (US); Laura R. Jarboe, Ames, IA (US); Lorraine P. Yomano, Gainesville, FL (US); Sean W. York, Gainesville, FL (US); Keelnatham Shanmugam, Gainesville, FL (US); Lonnie O'Neal Ingram, Gainesville, FL (US)

(73) Assignee: UNIVERSITY OF FLORIDA RESEARCH FOUNDATION, INC., Gainsville, FL (US)

( * ) Notice: Subject to any disclaimer, the term of this patent is extended or adjusted under 35 U.S.C. 154(b) by 273 days.

This patent is subject to a terminal disclaimer.

(21) Appl. No.: 13/147,155

(22) PCT Filed: Jan. 4, 2010

(86) PCT No.: PCT/US2010/020051
§ 371 (c)(1),
(2), (4) Date: Dec. 15, 2011

(87) PCT Pub. No.: WO2010/101665
PCT Pub. Date: Sep. 10, 2010

(65) Prior Publication Data
US 2012/0077241 A1    Mar. 29, 2012

Related U.S. Application Data

(60) Provisional application No. 61/209,334, filed on Mar. 5, 2009.

(51) Int. Cl.
| | |
|---|---|
| *C12N 1/20* | (2006.01) |
| *C12N 1/21* | (2006.01) |
| *C12N 9/04* | (2006.01) |
| *C12P 7/10* | (2006.01) |
| *C12P 7/06* | (2006.01) |
| *C12N 9/02* | (2006.01) |

(52) U.S. Cl.
CPC ............... *C12P 7/065* (2013.01); *C12N 9/0008* (2013.01); *Y02E 50/16* (2013.01); *Y02E 50/17* (2013.01)

(58) Field of Classification Search
CPC .................. C12N 1/20; C12N 9/0006; C12Y 101/01274; C12Y 101/01021
USPC .................. 435/252.3, 252.33, 190
See application file for complete search history.

(56) References Cited

U.S. PATENT DOCUMENTS

| | | |
|---|---|---|
| 7,371,558 B2 | 5/2008 | Cervin et al. |
| 2006/0252136 A1 | 11/2006 | Caimi et al. |
| 2008/0090283 A1* | 4/2008 | Lefebvre et al. ............... 435/245 |

FOREIGN PATENT DOCUMENTS

| | | |
|---|---|---|
| WO | WO 2006/121755 | 11/2006 |
| WO | WO 2008/021141 A2 * | 2/2008 |
| WO | WO 2008/116851 A1 * | 10/2008 |

OTHER PUBLICATIONS

Pérez et al., J. Biol. Chem. 283:7346-7353, Jan. 2008.*
Miller et al., Appl. Environmen. Microbiol. 75:4315-4323, Jul. 2009.*
Miller et al., Society for Industrial Microbiology Annual Meeting Abstract 6858, Aug. 2008, 1 page.*
Miller et al., Appl. Environ. Microbiol. 75:4315-4323, 2009.*
Turner et al., J. Ind. Microbiol. Biotechnol. 38:431-439, 2011.*
Clark et al., FEMS Microbiol. Rev. 63:223-234, 1989.*
Heer et al., Microb. Biotechnol. 1:497-506, 2008.*
Perez et al., J. Biol. Chem. 283:7346-7353, 2008.*
Baba et al., Mol. Syst. Biol. 2006.008, 2006, 11 pages.*
Baba et al., Mol. Syst. Biol. 2006.008, 2006, Supplementary Table 2, 50 pages.*
Dawes et al., "The formation of ethanol in *Escherichia coli*", Biochim Biophys Acta vol. 22, p. 253, 1956.*
Form PCT/ISA/210, Apr. 30, 2010, ISR for PCT/US2010/020051.
Form PCT/ISA/237, Apr. 30, 2010, Written Opinion or PCT/US2010/020051.
Miller et al., Characterization of a furfural resistant mutant of ethanologenic *Escherichia coli*. Society for Industrial Microbiology Annual Meeting Abstract 6858. [online] Aug. 2008. [retrieved Apr. 8, 2010] Available on the internet: <URL: http://sim.confex.com/sim/2008/preliminaryprogram/abstract_6858.htm> Abstract only.
GeneChip *E. coli*. Affymetrix (online) 2005 [retrieved on Apr. 19, 2010] Retrieved from the internet URL:<http://www.affymetrix.com/support/technical/datasheets/ecoli2_datasheet.pdf>, see p. 1, para 2.
Jarboe et al. Development of ethanologenic bacteria. Adv Biochem Eng Biotechnol Jul. 31, 2007 vol. 108 pp. 237-261. Especially p. 248 para 1.
Genebank AP009240.1 *Escherichia coli* SE11 DNA, complete genome Dec. 23, 2008 [online] [retrieved Apr. 9, 2010]. Available on the internet:<NRL: http://www.ncbi.nlm.nih.gov/nuccore/209910450?from=342154&to=3421691&report=gbwithparts>.
Yum et al. Identification of the yqhE and yafB Genes Encoding Two 2,5-Diketo-d-Gluconate Reductases in *Escherichia coli*. Appl Environ Microbiol Aug. 1999 vol. 65 No. 8 pp. 3341-3343. Especially p. 3345 left col para 1.

(Continued)

*Primary Examiner* — David J Steadman
(74) *Attorney, Agent, or Firm* — Saliwanchik, Lloyd & Eisenschenk

(57) ABSTRACT

The invention relates to bacterium that have increased resistance to furfural and methods of preparation. The invention also relates to methods of producing ethanol using the bacterium and corresponding kits.

12 Claims, 35 Drawing Sheets

(56) References Cited

OTHER PUBLICATIONS

Miller et al. Silencing of NADPH-dependent oxidoreductase genes (yqhD and dkgA) in furfural-resistant ethanologenic *Escherichia coli*. Appl environ Microbiol Jul. 2009 (ePub May 8, 2008) vol. 75 No. 13 pp. 4315-4323. Especially abstract, p. 4320 right col para 2.

Gutierrez et al. Purification and characterization of a furfural reductase (FFR) from *Escherichia coli* strain LYO1—an enzyme important in the detoxification of furfural during ethanol production. J Biotechnology Jan. 24, 2006 vol. 121 No. 2 pp. 154-164. Especially abstract.

Tao et al. Engineering a homo-ethanol pathway in *Escherichia coli*: increased glycolytic flux and levels of expression of glycolytic genes during xylose fermentation. J Bacteriol May 2001 vol. 183 No. 10 pp. 2979-2988. Especially abstract.

Fadl et al. Global gene expression of a murein (Braun) lipoprotein mutant of *Salmonella enterica* serovar Typhimurium by microarray analysis. Gene, vol. 374, Jun. 7, 2006, pp. 121-127, especially p. 124, table 3; and p. 125, para 1.

Miller, E. N. et al. "Genetic changes that increase 5-hydroxymethyl furfural resistance in ethanol-producing *Escherichia coli* LY180" *Biotechnology Letters*, 2010, pp. 661-667, vol. 32.

Davison, J. "Genetic Tools for Pseudomonads, Rhizobia, and Other Gram-Negative Bacteria" *BioTechniques*, Feb. 2002, pp. 386-401, vol. 32, No. 2.

\* cited by examiner 4,082 bps, Accession No. FJ404781

3,621 bps, Accession No. FJ387231

3,151 bps, Accession No. FJ404780

6,962 bps, Accession No. FJ404782

1,960 bps, Accession No. FJ404783

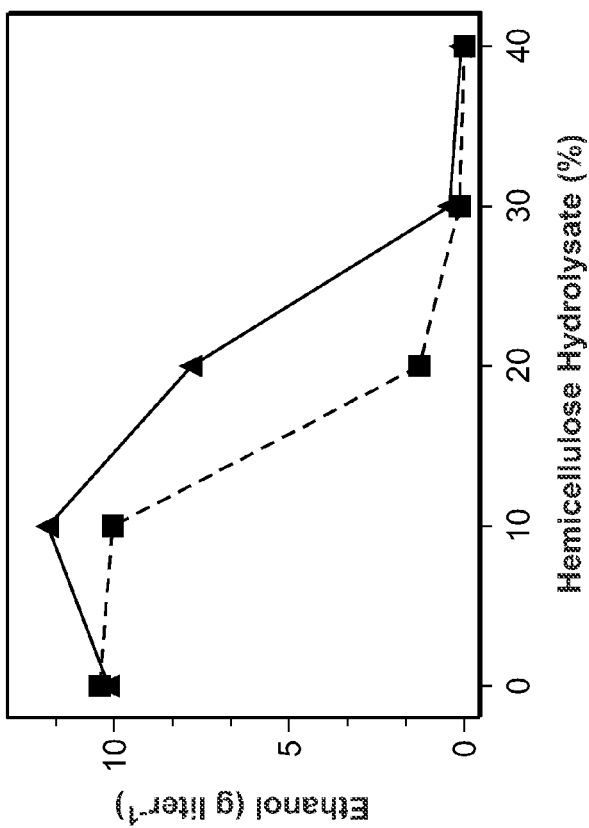
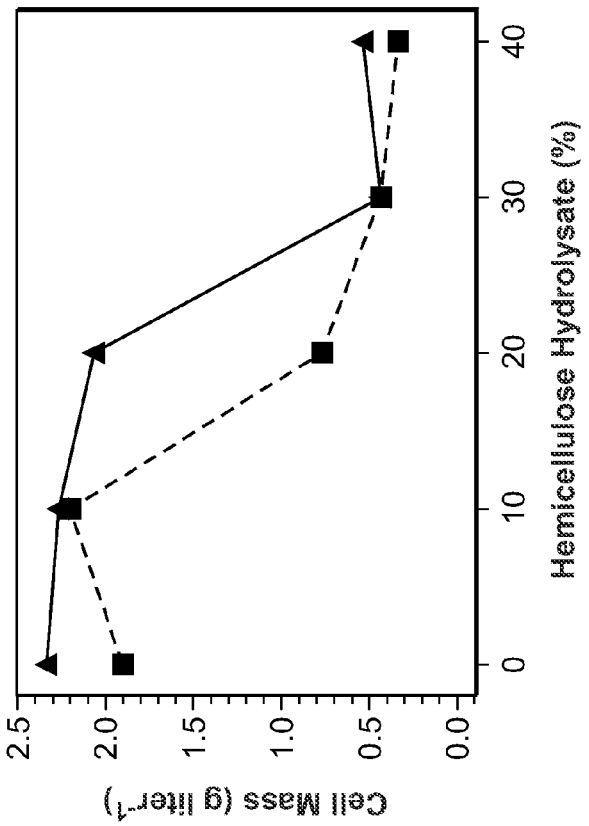
FIG. 7A
FIG. 7B

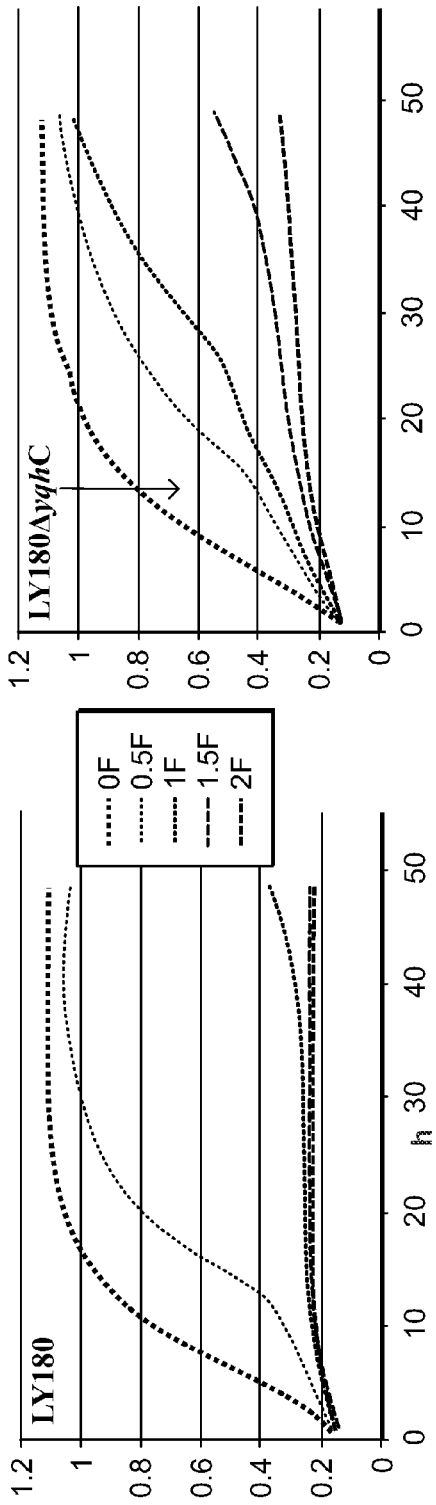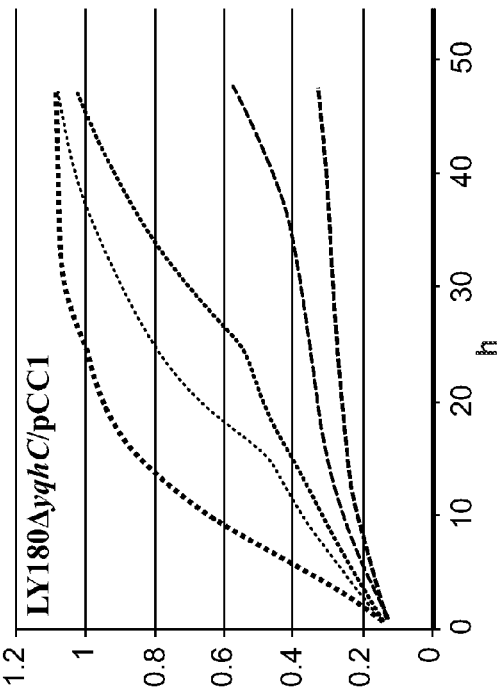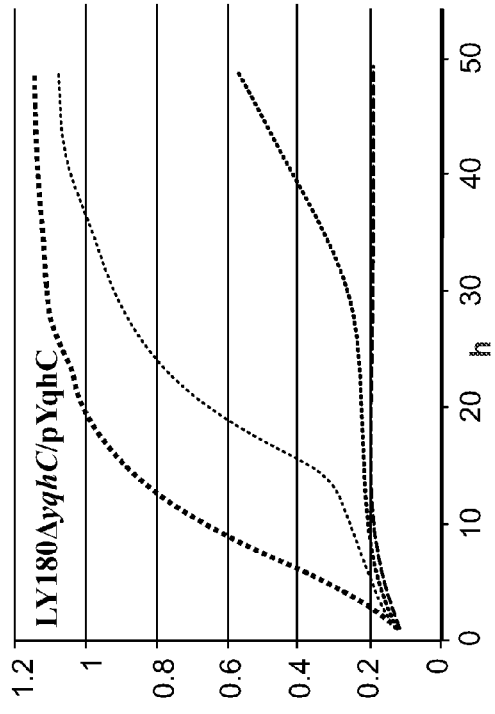

FIG. 16A

YqhD

MNNFNLHTPTRILFGKGAIAGLREQIPHDARVLITYGGGSVKKTGVLDQVLDALKGMDVL
EFGGIEPNPAYETLMNAVKLVREQKVTFLLAVGGGSVLDGTKFIAAAANYPENIDPWHIL
QTGGKEIKSAIPMGCVLTLPATGSESNAGAVISRKTTGDKQAFHSAHVQPVFAVLDPVYT
YTLPPRQVANGVVDAFVHTVEQYVTKPVDAKIQDRFAEGILLTLIEDGPKALKEPENYDV
RANVMWAATQALNGLIGAGVPQDWATHMLGHELTAMHGLDHAQTLAIVLPALWNEKRDTK
RAKLLQYAERVWNITEGSDDERIDAAIAATRNFFEQLGVPTHLSDYGLDGSSIPALLKKL
EEHGMTQLGENHDITLDVSRRIYEAAR

FIG. 16B yqhD atgaacaactttaatctgcacaccccaacccgcattctgtttggtaaaggcgcaatcgct
ggtttacgcgaacaaattcctcacgatgctcgcgtattgattacctacggcggcggcagc
gtgaaaaaaaccggcgttctcgatcaagttctggatgccctgaaaggcatggacgtgctg
gaatttggcggtattgagccaaaccggcttatgaaacgctgatgaacgccgtgaaactg
gttcgcgaacagaaagtgactttcctgctggcggttggcggcggttctgtactggacggc
accaaatttatcgccgcagcggctaactatccggaaaatatcgatccgtggcacattctg
caaacgggcggtaaagagattaaagcgccatcccgatgggctgtgtgctgacgctgcca
gcaaccggttcagaatccaacgcaggcgcggtgatctcccgtaaaaccacaggcgacaag
caggcgttccattctgcccatgttcagccggtatttgccgtgctcgatccggtttatacc
tacaccctgccgccgcgtcaggtggctaacggcgtagtggacgcctttgtacacaccgtg
gaacagtatgttaccaaaccggttgatgccaaaattcaggaccgtttcgcagaaggcatt
ttgctgacgctaatcgaagatggtccgaaagccctgaaagagccagaaaactacgatgtg
cgcgccaacgtcatgtgggcggcgactcaggcgctgaacggtttgattggcgctggcgta
ccgcaggactgggcaacgcatatgctgggccacgaactgactgcgatgcacggtctggat
cacgcgcaaacactggctatcgtcctgcctgcactgtggaatgaaaaacgcgataccaag
cgcgctaagctgctgcaatatgctgaacgcgtctggaacatcactgaaggttccgatgat
gagcgtattgacgccgcgattgccgcaacccgcaatttctttgagcaattaggcgtgccg
acccacctctccgactacggtctggacggcagctccatcccggctttgctgaaaaaactg
gaagagcacggcatgacccaactgggcgaaaatcatgacattacgttggatgtcagccgc
cgtatatacgaagccgcccgctaa

FIG. 17A

DkgA

MANPTVIKLQDGNVMPQLGLGVWQASNEEVITAIQKALEVGYRSIDTAAAYKNEEGVGKA
LKNASVNREELFITTKLWNDDHKRPREALLDSLKKLQLDYIDLYLMHWPVPAIDHYVEAW
KGMIELQKEGLIKSIGVCNFQIHHLQRLIDETGVTPVINQIELHPLMQQRQLHAWNATHK
IQTESWSPLAQGGKGVFDQKVIRDLADKYGKTPAQIVIRWHLDSGLVVIPKSVTPSRIAE
NFDVWDFRLDKDELGEIAKLDQGKRLGPDPDQFGG

FIG. 17B dkga atggctaatccaaccgttattaagctacaggatggcaatgtcatgccccagctgggactg
ggcgtctggcaagcaagtaatgaggaagtaatcaccgccattcaaaaagcgttagaagtg
ggttatcgctcgattgataccgccgcggcctacaagaacgaagaaggtgtcggcaaagcc
ctgaaaaatgcctcagtcaacagagaagaactgttcatcaccactaagctgtggaacgac
gaccacaagcgcccccgcgaagccctgctcgacagcctgaaaaaactccagcttgattat
atcgacctctacttaatgcactggcccgttcccgctatcgaccattatgtcgaagcatgg
aaaggcatgatcgaattgcaaaagagggattaatcaaaagcatcggcgtgtgcaacttc
cagatccatcacctgcaacgcctgattgatgaaactggcgtgacgcctgtgataaaccag
atcgaacttcatccgctgatgcaacaacgccagctacacgcctggaacgcgacacacaaa
atccagaccgaatcctggagcccattagcgcaaggagggaaaggcgttttcgatcagaaa
gtcattcgcgatctggcagataaatacggcaaaaccccggcgcagattgttatccgctgg
catctggatagcggcctggtggtgatcccgaaatcggtcacacttcacgtattgccgaa
aactttgatgtctgggatttccgtctcgacaaagacgaactcggcgaaattgcaaaactc
gatcagggcaagcgtctcggtcccgatcctgaccagttcggcggctaa

FIG. 18A

YqhC

MLQNCAQSNCRIIPKKLRDMKREEICRLLADKVNKLKNKENSLSGLLPDVRLLYGETPFA
RTPVMYEPGIIILFSGHKIGYINERVFRYDANEYLLLTVPLPFECETYATSEVPLAGLRL
NVDILQLQELLMDIGEDEHFQPSMAASGINSATLSEEILCAAERLLDVMERPLDARILGK
QIIREILYYVLTGPCGGALLALVSRQTHFSLISRVLKRIENKYTENLSVEQLAAEANMSV
SAFHHNFKSVTSTSPLQYLKNYRLHKARMMIIHDGMKASAAAMRVGYESASQFSREFKRY
FGVTPGEDAARMRAMQGN

FIG. 18B yqhC atgctacaaaattgcgcacaatcaaattgccgcattattcctaagaaattacgcgatatg
aaacgtgaagagatttgccgcttgctggcggataaagttaataaactgaaaaataaagaa
aatagtttgtcaggactgttgcccgatgtgcgtttgttgtatggcgagacgcctttcgca
cgtacaccggtgatgtacgagcctggcatcataattctcttttccgggcataaaatcggt
tatatcaatgaacgcgtgtttcgttatgatgccaatgaatacctgctgctgacggtgccg
ttgccgtttgagtgcgaaacctatgccacgtcagaggtgccgctggcagggttgcgtctc
aatgtcgatatttttgcagttacaggaactgttgatggacattggcgaagatgagcatttc
cagccgtcgatggcagccagcgggattaactccgccacgttatcagaagagatttatgc
gcggcggagcggttactcgacgtgatggagcgaccactggatgcgcgtattctcggcaaa
cagatcatccgcgaaattctgtactacgtgctgaccggaccttgcggcggcgcgttactg
gcgctggtcagtcgccagactcacttcagtctgattagccgcgtgctgaaacggattgag
aataaatacaccgaaaacctgagcgtcgagcaactggcggcagaagccaacatgagcgta
tcggcgttccaccataatttttaagtctgtcaccagtacctcgccgttgcagtatttgaag
aattaccgtctgcataaggcgcggatgatgatcatccatgacggcatgaaggccagcgca
gcagcgatgcgcgtcggctatgaaagcgcatcgcaatttagccgtgagtttaaacgttac
ttcggtgtgacgccggggaagatgcggcaagaatgcgggcgatgcaggggaattaa

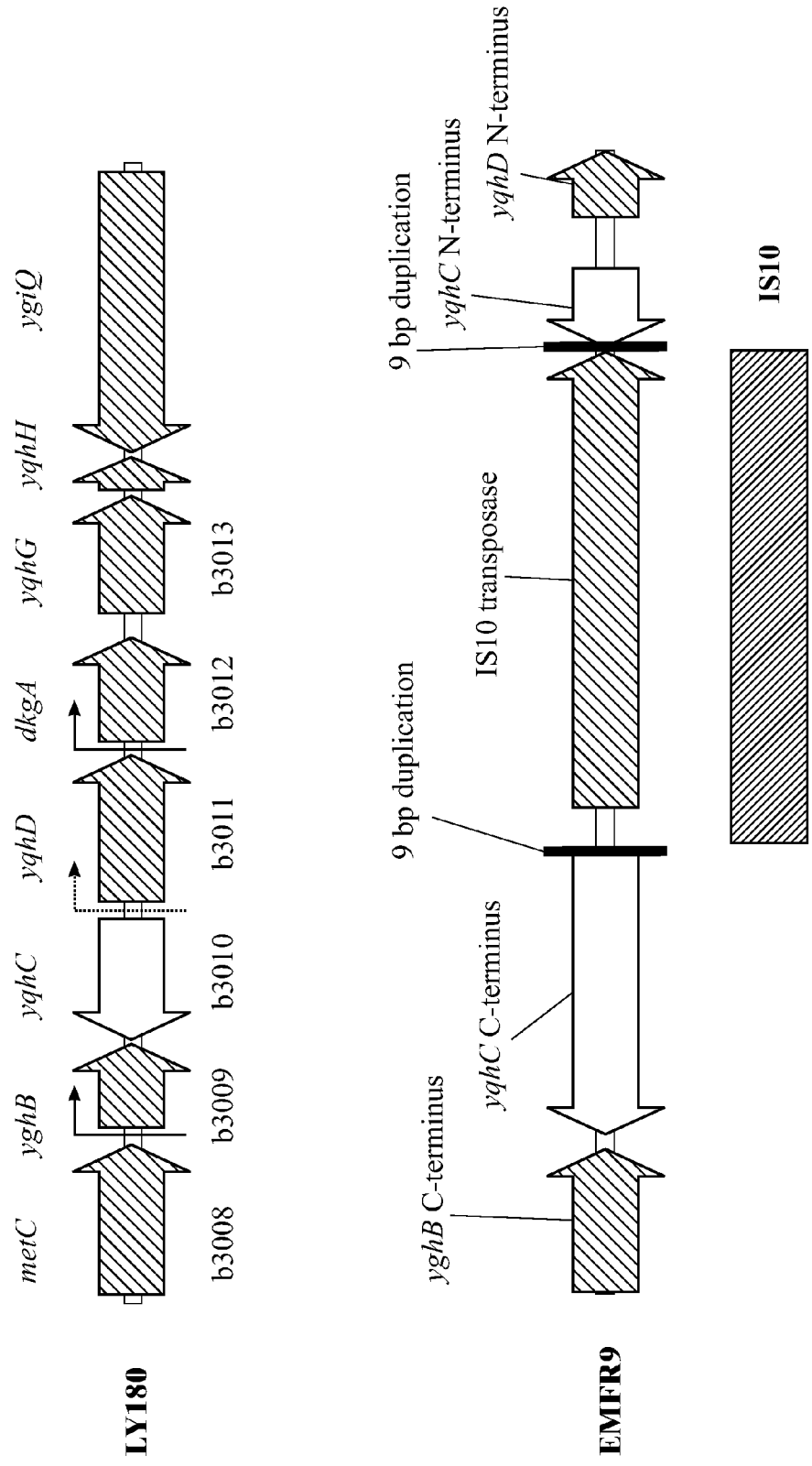

FIG. 23
Acinetobacter sp. ADP1
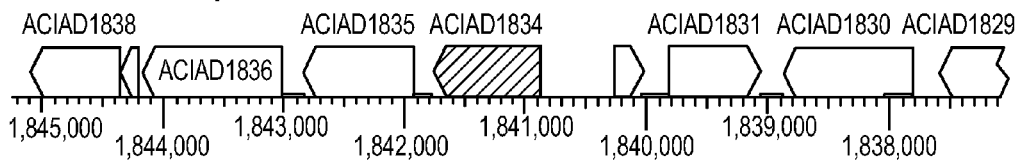
Xanthomonas campestris pv. campestris
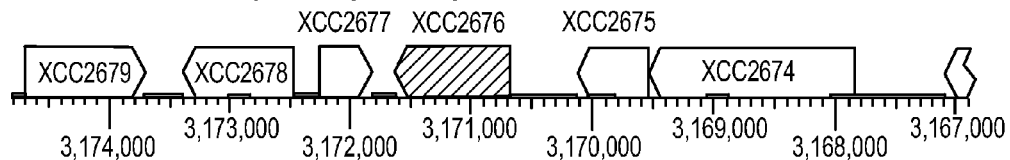
Aeromonas hydrophila subsp. Dhakensis *(yqhD)*
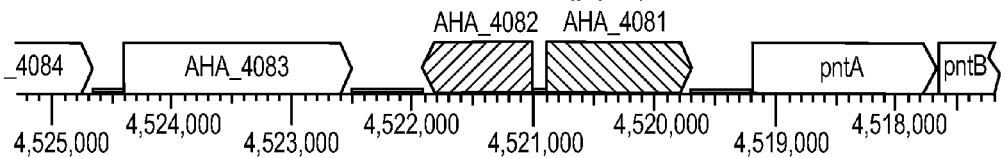
Vibrio parahaemolyticus *(yqhD)*
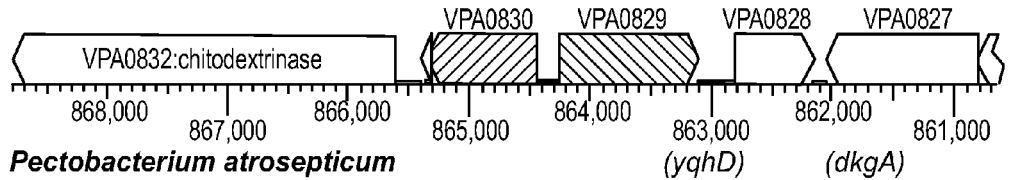
Pectobacterium atrosepticum *(yqhD)* *(dkgA)*
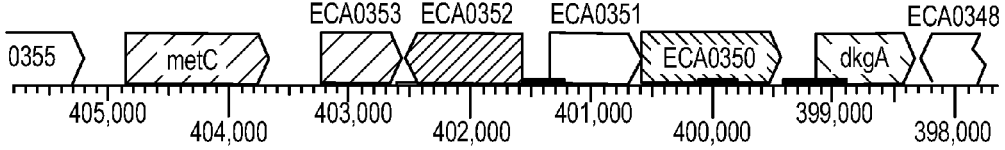
Yersinia pestis CO92 *(yqhD)* *(dkgA)*
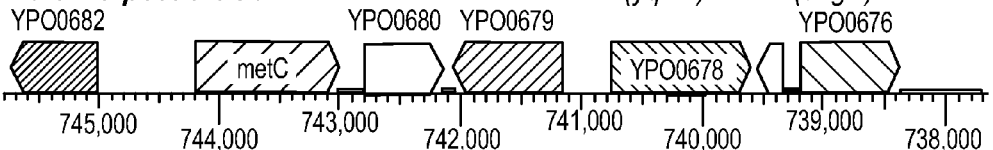
Klebsiella pneumoniae MGH 78578 *(yqhD)* *(dkgA)*
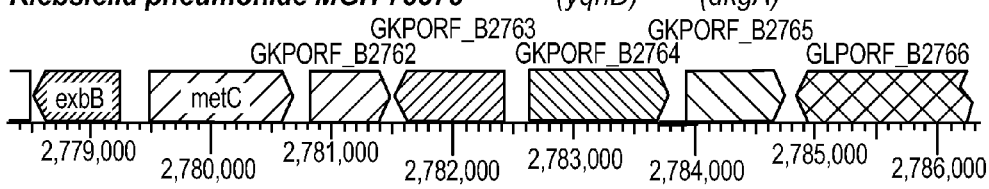
Escherichia coli K-12 MG1655 yqhC yqhD dkgA
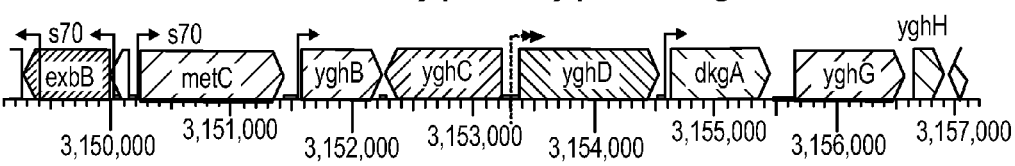

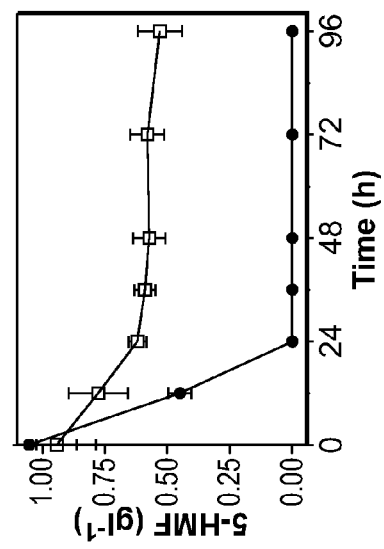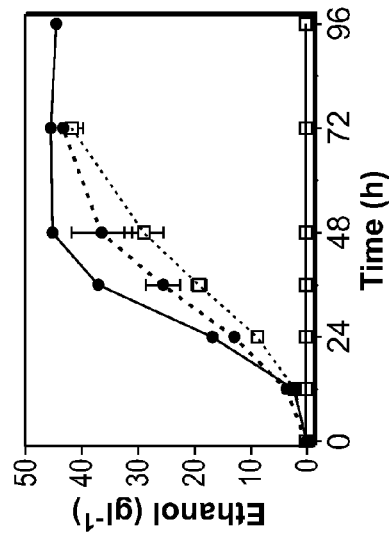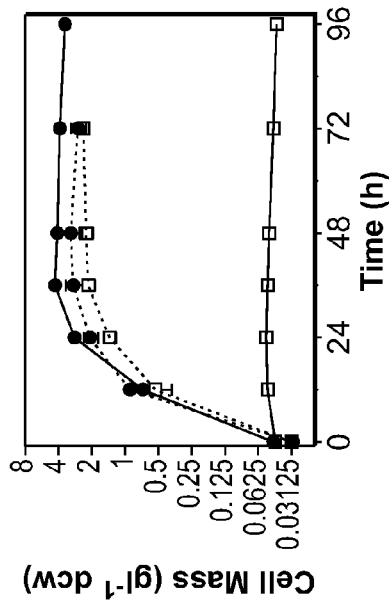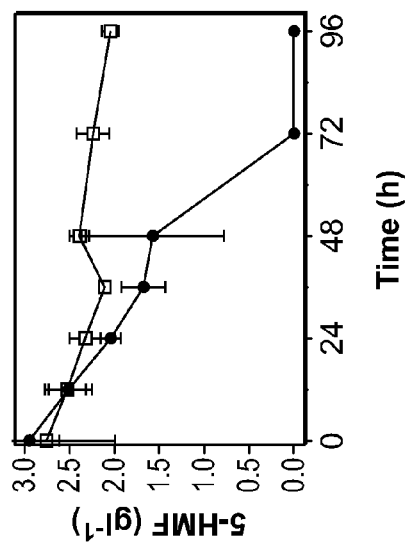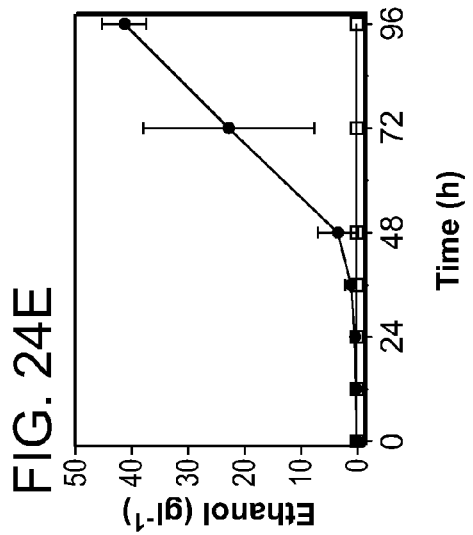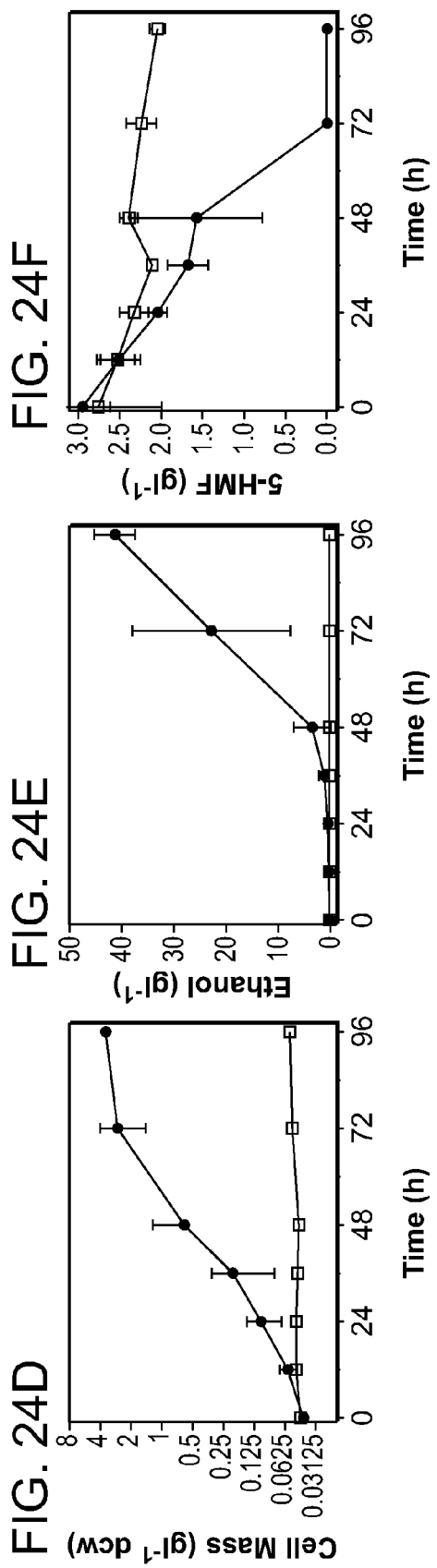
FIG. 24A  FIG. 24B  FIG. 24C
FIG. 24D  FIG. 24E  FIG. 24F yqhD (151 bp):
GCAATTTGTAGCATTTCTCCAGCACTCTGGAGGAATAGGCAAGACATTGGCAGAAATG
AGCATTGAGAGCCAGGGGCGCTGGCGATCACAATGAAAAACATCAGGCAGATCGTTCTCT
GCCCTCATATTGGCCCAGCAAAGGGAGCAAGTA dkgA (104 bp):
GCTTTTTACGCCTCAAACTTTCGTTTTCGGGCATTTCGTCCAGACTTAAGTTCACAACACC
TCACCGGAGCCTGCTCCGGTGAGTTCATATAAAGGAGGAACGT

FIG. 29A

```
   1 atggcggaca aaaagcttga tactcaactg gtgaatgcag gacgcagcaa aaaatacact
  61 ctcggcgcgg taaatagcgt gattcagcgc gcttcttcgc tggtctttga cagtgtggaa
 121 gccaaaaaac acgcgacgcg caatcgcgcc aatggtgagt tgttctatgg acggcgtgga
 181 acgttaaccc atttctcctt acaacaagcg atgtgtgaac tggaaggtgg cgcaggctgc
 241 gtgctatttc cctgcggggc ggcggcggtt gctaattcca ttcttgcttt tgtcgaacag
 301 ggcgatcatg tgctgatgac caacaccgcc tatgaaccga gtcaggattt ctgtagcaaa
 361 atcctcagca aactgggcgt aacgacatcg tggtttgatc cgctgattgg tgccgatatc
 421 gttaagcatc tgcagccaaa cactaaaatc gtgtttctgg aatcgccagg ctccatcacc
 481 atggaagtcc acgacgttcc ggcgattgtt gccgccgtac gcagtgtggc gccggatgcc
 541 atcattatga tcgacaacac ctgggcagcc ggtgtgctgt taaggcgct ggattttggc
 601 atcgatgttt ctattcaagc cgccaccaaa tatctggttg gcattcaga tgcgatgatt
 661 ggcactgccg tgtgcaatgc ccgttgctgg agcagctac gggaaaacgc ctatctgatg
 721 ggccagatgg tcgatgccga taccgcctat ataaccagcc gtggcctgcg cacattaggt
 781 gtgcgtttgc gtcaacatca tgaaagcagt ctgaaagtgg ctgaatggct ggcagaacat
 841 ccgcaagttg cgcgagttaa ccaccctgct ctgcctggca gtaaaggcca cgaattctgg
 901 aaacgagact ttacaggcag cagcgggcta ttttcctttg tgcttaagaa aaaactcagt
 961 aatgaagagc tggcgaacta tctggataac ttcagtttat tcagcatggc ctactcgtgg
1021 ggcgggtatg aatcgttgat cctggcgaat caaccagaac atatcgccgc cattcgccca
1081 caaggcgaga tcgattttag cgggaccttg attcgcctgc atattggtct ggaagatgtc
1141 gacgatctga ttgccgatct ggacgccggt tttgcgcgaa ttgtataaca ttgccacttt
1201 tggacaattt tgcagacatt taattgtgaa aagtcttaaa ttgttgcgtc cgggatcaag
1261 gcgtcccgga cgaatcagga gtacaatagg cagataaagg cttaaacgct gttccacagg
1321 aaagtccatg gctgttattc aagatatcat cgctgcgctc tggcaacacg actttgccgc
1381 gctggcggat cctcatattg ttagcgttgt ttactttgtc atgtttgcca cgctgttttt
1441 agaaaacggc ctgctgcccg cctcattttt gccaggcgac agcttgttga tactggcagg
1501 cgcattgatt gccaggggg tatggattt tctgcctacg attgcgattc tgaccgccgc
1561 agcaagtctg ggctgctggc taagttatat tcagggggc tggttaggga ataccaaaac
1621 ggtgaaaggc tggctggcac agcttcctgc taaatatcac cagcgcgcca cctgcatgtt
1681 tgaccgccac ggtctgctgg cgctgctggc tggacgtttt cttgcatttg tccgtacgct
1741 gctgccaacc atggcgggaa tttccggtct gccaaaccgc cgcttccagt ttttcaactg
1801 gttaagtgga ttgctgtggg tcagcgtggt aaccagtttt ggctatgcct taagtatgat
1861 tccgttcgtt aaacgccatg aagatcaggt aatgacgttc ctgatgatcc tgccaattgc
1921 cttgttaacc gctggcttgt taggcacgct gtttgtggtg attaaaaaaa aatactgtaa
1981 cgcctgacga ttttccccgt tccggctgc tgtaccggga acgtatttaa ttcccctgca
2041 tcgcccgcat tcttgccgca tcttcccccg gcgtcacacc gaagtaacgt ttaaactcac
```

FIG. 29A (continued)

```
2101 ggctaaattg cgatgcgctt tcatagccga cgcgcatcgc tgctgcgcta gccttcatgc
2161 cgtcatggat gatcatcatc cgcgccttat gcagacggta attcttcaaa tactgcaacg
2221 gcgaggtgct ggtgacagac ttaaaattat ggtggaacgc cgatacgctc atgttggctt
2281 ctgccgccag ttgctcgacg ctcaggtttt cggtgtattt attctcaatc cgtttcagca
2341 cgcggctaat cagactgaag tgagtctggc gactgaccag cgccagtaac gcgccgccgc
2401 aaggtccggt cagcacgtag tacagaattt cgcggatgat ctgtttgccg agaatacgcg
2461 catccagtgg tcgctccatc acgtcgagta accgctccgc cgcgcataaa atctcttctg
2521 ataacgtggc ggagttaatc ccgctggctg ccatcgacgg ctggaaatgc tcatcttcgc
2581 caatgtccat caacagttcc tgtaactgca aaatatcgac attgagacgc aaccctgcca
2641 gcggcacctc tgacgtggca taggtttcgc actcaaacgg caacggcacc gtcagcagca
2701 ggtattcatt ggcatcataa cgaaacacgc gttcattgat ataaccgatt ttatgcccgg
2761 aaaagagaat tatgatgcca ggctcgtaca tcaccggtgt acgtgcgaaa ggcgtctcgc
2821 catacaacaa acgcacatcg gcaacagtt ctgacaaact atttctttta attttcagtt
2881 tattaacttt atccgccagc aagcggcaaa tctcttcacg tttcatatcg cgtaatttct
2941 taggaataat gcggcaattt gattgtgcgc aattttgtag catttctcca gcactctgga
3001 ggaataggca agacattggc agaaatgagc attgagagcc agggcgctgg cgatcacaat
3061 gaaaaacatc aggcagatcg ttctctgccc tcatattggc ccagcaaagg gagcaagtaa
3121 tgaacaactt taatctgcac accccaaccc gcattctgtt tggtaaaggc gcaatcgctg
3181 gtttacgcga acaaattcct cacgatgctc gcgtattgat tacctacggt ggcggcagcg
3241 tgaaaaaaac cggcgttctc gatcaagttc tggatgccct gaaaggcatg gacgtgctgg
3301 aatttggcgg tattgagcca aacccggctt atgaaacgct gatgaacgcc gtgaaactgg
3361 ttcgcgaaca gaaagtgact ttcctgctgg cggttggcgg cggttctgta ctggacggca
3421 ccaaatttat cgccgcagcg gctaactatc cggaaaatat cgatccgtgg cacattctgc
3481 aaacgggcgg taaagagatt aaaagcgcca tcccgatggg ctgtgtgctg acgctgccag
3541 caaccggttc agaatccaac gcaggcgcgg tgatctcccg taaaaccaca ggcgacaagc
3601 aggcgttcca ttctgcccat gttcagccgg tatttgccgt gctcgatccg gtttatacct
3661 acaccctgcc gccgcgtcag gtggctaacg gcgtagtgga cgcctttgta cacaccgtgg
3721 aacagtatgt taccaaaccg gttgatgcca aaattcagga ccgtttcgca gaaggcattt
3781 tgctgacgct gatcgaagat ggtccgaaag ccctgaaaga gccagaaaac tacgatgtgc
3841 gcgccaacgt catgtggggg gcgacgcagg cgctgaacgg tttgattggc gctggcgtac
3901 cgcaggactg gcaacgcat atgctgggcc acgaactgac tgcgatgcac ggtctggatc
3961 acgcgcaaac actggctatc gtcctgcctg cactgtggaa tgaaaaacgc gagaccaagc
4021 gcgctaagct gctgcaatat gctgaacgcg tctggaacat cactgaaggt tccgatgatg
4081 agcgtattga cgccgcgatt gccgcaaccc gcaatttctt tgagcaatta ggcgtgccga
4141 cccacctctc cgactacggt ctggacggca gctccatccc ggctttgctg aaaaaactgg
4201 aagagcacgg catgacccaa ctgggcgaaa atcatgacat tacgttggat gtcagccgcc
4261 gtatatacga agccgcccgc taagcttttt acgcctcaaa ctttcgtttt cgggcatttc
4321 gtccagactt aagttcacaa cacctcaccg gagcctgctc cggtgagttc atataaagga
4381 ggaacgtatg gctaatccaa ccgttattaa gctacaggat ggcaatgtca tgccccagct
```

FIG. 29A (continued)

```
4441 gggactgggc gtctggcaag caagtaatga ggaagtaatc accgccattc aaaaagcgtt
4501 agaagtgggt tatcgctcga ttgataccgc cgcggcctac aagaacgaag aaggtgtcgg
4561 caaagccctg aaaaatgcct cagtcaacag agaagaactg ttcatcacca ctaagctgtg
4621 gaacgacgac cacaagcgcc ccgcgaagc cctgctcgac agcctgaaaa aactccagct
4681 tgattatatc gacctctact taatgcactg gcccgttccc gctatcgacc attatgtcga
4741 agcatggaaa ggcatgatcg aattgcaaaa agagggatta atcaaaagca tcggcgtgtg
4801 caacttccag atccatcacc tgcaacgcct gattgatgaa actggcgtga cgcctgtgat
4861 aaaccagatc gaacttcatc cgctgatgca acaacgccag ctacacgcct ggaacgcgac
4921 acacaaaatc cagaccgaat cctggagccc attagcgcaa ggagggaaag gcgttttcga
4981 tcagaaagtc attcgcgatc tggcagataa atacggcaaa accccggcgc agattgttat
5041 ccgctggcat ctggatagcg gcctggtggt gatcccgaaa tcggtcacac cttcacgtat
5101 tgccgaaaac tttgatgtct gggatttccg tctcgacaaa gacgaactcg gcgaaattgc
5161 aaaactcgat cagggcaagc gtctcggtcc cgatcctgac cagttcggcg gctaacatgc
5221 aaattctccc ggtggcggta atgttccgct accggacttt tcagaaatca tttattcccc
5281 tcgcgtcccg cccgttgtta ctcttccttg ttcaggaatg ccaaatataa ggacatcatc
5341 atgcagagcc ggaagctctt aaaagaacaa ctcatctata tccgggataa acgcaacgga
5401 gaggtgaaaa acagatgaaa ataatacttc tgttttagc agccctggca agttttaccg
5461 tacacgcaca gcccccctca ctgaccgtag aacaaacagt ccggcatatt tatcagaact
5521 ataaatcaga tgccactgcc ccttattttg gtgaaaccgg agagcgggcg ataacttctg
5581 cgcgtattca acaggcgctt accctgaacg acaatcttac gctgccgggc aatattggct
5641 ggctggatta tgatccggtt tgtgattgtc aggattttgg cgatctggtg ctagaaagcg
5701 tagcgataac tcaaactgac gccgatcatg ccgatgccgt tgtgcgcttt cgtatcttta
5761 aagatgataa agaaaagacc acgcagacac tgaaaatggt ggcggaaaat ggtcgttggg
5821 tcattgacga tattgtcagc aatcatggca gcgtcttaca agcagttaat agcgagaatg
5881 aaaaaacgct ggccgcttta gcttcgttgc aaaaagaaca gccggaagcc tttgttccg
5941 aactctttga acatattgct gattatagct ggccgtggac gtgggtggtt ccgactctt
6001 accgccaggc ggttaatgcc ttctataaaa ccaccttcaa gacggccaat aatcccgatg
6061 aagatatgca aatagaacgg caatttattt acgacaatcc gatctgtttt ggcgaagagt
6121 cgctattttc acgcgttgat gaaattcgag tcctggagaa aaccgccgat tccgcccgca
6181 ttcatgttcg ttttacgctg accaatggca acaacgaaga gcaagaactg gttttacagc
6241 ggcgcgaagg caagtgggaa atcgctgatt ttatccgccc gaacagcggc agcctactta
6301 agcagattga ggcaaaaacc gccgccagat taaagcaatg agctgaatta aataacaatt
6361 agccggaaca ataaataaaa gggaacacta tatgaaaacg attttcaccg tgggagttgt
6421 tgttctggca acctgcttgc tcagtggctg cgtcaatgag caaaaggtca atcagctggc
6481 gagcaatgtg caaacattaa atgccaaaat cgcccggctt gagcaggata tgaaagcact
6541 acgcccacaa atctatgctg ccaaatccga agctaacaga gccaatacgc gtcttgatgc
6601 tcaggactat tttgattgcc tgcgctgctg cgtatgtac gcagaatgat aaaaaaatcc
6661 ccggcagcat gtcagttgcc ggggattttt tttaacgtcc aaccgccgct tagggcgtt
6721 tcttcgcacc agcattcacc ggacgagatt gcgtagacga cgcttttttt gccgtagcag
```

FIG. 29A (continued)

```
6781 gcgtctgacg ctgagtcgcc atcggcgtat gtttcgtcaa cgccggacgg gtattgcggt
6841 tctggcgacg agcttcacgc atctcttcaa tggttggcgc aggcactaag caatcgcgac
6901 ggctgccaat cagatgcttt tgcccatcg cttccagcgc ctggcggatt aacggccagt
6961 ttgccggatc gtggtaacgc aacaacgctt tatgcaaacg acgctgtttg tcgcccttcg
7021 gtacgaagac gtcttcactc ttataaccaa tcttcgccag cgggttttc ccggtgtaat
7081 acatggtggt tgagttcgcc agcggcgatg ggtagaagtt ctgtacctgg tcgagacgga
7141 aacgatgctt tttcagccac agcgccagat tcaccatatc ttcatcacgc gtaccggggt
7201 gcgcggagat gaaatagggg atcagatact gctctttacc tgcctgtttt gagtaagtat
7261 cgaacagctc tttaaagcgg tcatagctgc ccatgcccgg cttcatcatc ttcgataacg
7321 gcccttcttc ggtatgttcc ggggcaatct tcagataacc gccgacgtga tgggtcgcca
7381 actctttgat atagcgcgga tcttccacgg cgatgtcata acgtacgcct gaggcgatga
7441 ggatttttt aatgcctttc agatcacgcg cacggcgata gaggttgatc gtcggttcgt
7501 ggttagtgtc catgtgcgga caaatatccg gataaacgca cgacaaacgg cgacaagttt
7561 gttcagcgcg tggcgatttg cagcgcaaca tatacatgtt ggcagttggc ccaccgagat
7621 cggaaatcac gcccgtaaaa cctggaacgg tgtcgcggat cgcttcgatc tcattaatga
7681 tcgaatcttc cgaacggctc tgaataatgc gcccttcgtg ctcggtaata aacagaaag
7741 aacagccgcc aaagcagccg cgcataatgt tgaccgaaaa acggatcatt tcgtaagccg
7801 gaatacgggc attgccatag gccggatgtg gcacgcgctt gtacggcagc gcaaaaacgc
7861 tgtccatctc ttcggtagaa agcgggatag caggcgggtt gatccacaca tagcggtcac
7921 cgtgttttg catcaatgcg cgggcgcagc ctgggttggt ttcgtggtgc agaatgcgcg
7981 aagcatgggc gtacagcact ttatcgccct tcactttctc gaaagaaggc agcaacacgt
8041 aggttttttc ccacggtttc gggcgcggtg gctgcacggt tacggctttg gcttcctgct
8101 ttttcggtgc caccggtttg ttatccgcgc acggcaaatc ttcaccatac ggatgcggga
8161 ttgggtcgat ttttccaggg gtatcaagac gggtggaatc cacgccgctc cagccaggca
8221 gcgcctcttc cacgataatc gcggtattac gcacatcgcg gatttcacta atcggctcgc
8281 ccatcgccag acgtgcgcc acctccacca gcggacgctc accgttacca aacatcagca
8341 tgtcggcttt cgaatccacc agcacggaac ggcgcacggt atcggaccag taatcataat
8401 gtgcggtacg gcgcagacta gcctcaatac cgccgaggat caccggtaca tctttccacg
8461 cctctttaca acgctgggta taaaccagtg tggcgcgatc cgggcgctta cccgcgacgt
8521 tatccggcgt gtaggcatcg tcatgacgta aacggcgatc ggcggtataa cggttgatca
8581 tcgaatccat gttgccagca gtaacaccga aaacagatt cggtttaccc agacgcatga
8641 aatcgtcttt gctgctccag tctggctggg cgatgatccc gacgcgaaag ccctgtgctt
8701 ccagcatacg accgcaaatc gccatcccga gcttgggtg atcgacatac gcgtcgccag
8761 taaccaaaat gatgtcgcag ctatcccagc caagttgatc catctcttca cgagacatcg
8821 gcaaaaacgg tgccggtcca aaacaggcgg cccagtactg cggccaggag aacaggtcgc
8881 gatccggttg gatcagggag atagagctca ttttgcttcc agaaatgata aaaaataat
8941 caaaggccgg ggattataag ccggaacgaa agagaaatcg aaaggtattc catactcgcc
9001 ctcctcgggc gagtatgaag attacggtac cggattgacc aaaagttg //
```

FIG. 29B

```
   1 aataccaaaa cggtgaaagg ctggctggca cagcttcctg ctaaatatca ccagcgcgcc
  61 acctgcatgt ttgaccgcca cggtctgctg gcgctgctgg ctggacgttt tcttgcattt
 121 gtccgtacgc tgctgccaac catggcggga atttccggtc tgccaaaccg ccgcttccag
 181 tttttcaact ggttaagtgg attgctgtgg gtcagcgtgg taaccagttt tggctatgcc
 241 ttaagtatga ttccgttcgt aaacgccat gaagatcagg taatgacgtt cctgatgatc
 301 ctgccaattg ccttgttaac cgctggcttg ttaggcacgc tgtttgtggt gattaaaaaa
 361 aaatactgta acgcctgacg attttccccg ttcccggctg ctgtaccggg aacgtattta
 421 attccctgc atcgcccgca ttcttgccgc atcttccccc ggcgtcacac cgaagtaacg
 481 tttaaactca cggctaaatt gcgatgcgct ttcatagccg acgcgcatcg ctgctgcgct
 541 agccttcatg ccgtcatgga tgatcatcat ccgcgcctta tgcagacggt aattcttcaa
 601 atactgcaac ggcgaggtgc tggtgacaga cttaaaatta tggtggaacg ccgatacgct
 661 catgttggct tctgccgcca gttgctcgac gctcaggttt tcggtgtatt tattctcaat
 721 ccgtttcagc acgcggctaa tcagactgaa gtgagtctgg cgactgacca cgccagtaa
 781 cgcgccgccg caaggtccgg tcagcacgta gtacagaatt tcgcggatga tctgtttgcc
 841 gagaatacgc gcatccagtg gtcgctccat cacgtcgagt aaccgctccg ccgcgcataa
 901 aatctcttct gataacgtgg cggagttaat cccgctggct gccatcgacg gctggaaatg
 961 ctcatcttcg ccaatgtcca tcaacagttc ctgtaactgc aaaatatcga cattgagacg
1021 caaccctgcc agcggcacct ctgacgtggc ataggtttcg cactcaaacg gcaacggcac
1081 cgtcagcagc aggtattcat ggcatcata acgaaacacg cgttcattga taaccgat
1141 tttatgcccg gaaaagagaa ttatgatgcc aggctctgat gaatcccta atgattttgg
1201 taaaaatcat taagttaagg tggatacaca tcttgtcata tgatcaaatg gtttcgcgaa
1261 aaatcaataa tcagacaaca agatgtgcga actcgatatt ttacacgact ctctttacca
1321 attctgcccc gaattacact taaaacgact caacagctta acgttggctt gccacgcatt
1381 acttgactgt aaaactctca ctcttaccga acttggccgt aacctgccaa ccaaagcgag
1441 aacaaaacat aacatcaaac gaatcgaccg attgttaggt aatcgtcacc tccacaaaga
1501 gcgactcgct gtataccgtt ggcatgctag ctttatctgt tcgggcaata cgatgcccat
1561 tgtacttgtt gactggtctg atattcgtga gcaaaaacga cttatggtat tgcgagcttc
1621 agtcgcacta cacggtcgtt ctgttactct ttatgagaaa gcgttcccgc tttcagagca
1681 atgttcaaag aaagctcatg accaattct agccgacctt gcgagcattc taccgagtaa
1741 caccacaccg ctcattgtca gtgatgctgg ctttaaagtg ccatggtata aatccgttga
1801 gaagctgggt tggtactggt taagtcgagt aagaggaaaa gtacaatatg cagacctagg
1861 agcggaaaac tggaaaccta tcagcaactt acatgatatg tcatctagtc actcaaagac
1921 tttaggctat aagaggctga ctaaaagcaa tccaatctca tgccaaattc tattgtataa
1981 atctcgctct aaaggccgaa aaaatcagcg ctcgacacgg actcattgtc accaccgtc
2041 acctaaaatc tactcagcgt cggcaaagga gccatgggtt ctagcaacta acttacctgt
2101 tgaaattcga acacccaaac aacttgttaa tatctattcg aagcgaatgc agattgaaga
2161 aaccttccga gacttgaaaa gtcctgccta cggactaggc ctacgccata gccgaacgag
2221 cagctcagag cgttttgata tcatgctgct aatcgccctg atgcttcaac taacatgttg
2281 gcttgcgggc gttcatgctc agaaacaagg ttgggacaag cacttccagg ctaacacagt
2341 cagaaatcga aacgtactct caacagttcg cttaggcatg gaagttttgc ggcattctgg
```

FIG. 29B (continued)

```
2401 ctacacaata acaagggaag acttactcgt ggctgcaacc ctactagctc aaaatttatt
2461 cacacatggt tacgctttgg ggaaattatg aggggatctc tcagtgccag gctcgtacat
2521 caccggtgta cgtgcgaaag gcgtctcgcc atacaacaaa cgcacatcgg gcaacagttc
2581 tgacaaacta ttttctttaa ttttcagttt attaacttta tccgccagca agcggcaaat
2641 ctcttcacgt tcatatcgc gtaatttctt aggaataatg cggcaatttg attgtgcgca
2701 attttgtagc atttctccag cactctggag gaataggcaa gacattggca gaaatgagca
2761 ttgagagcca gggcgctggc gatcacaatg aaaaacatca ggcagatcgt tctctgccct
2821 catattggcc cagcaaaggg agcaagtaat gaacaacttt aatctgcaca ccccaacccg
2881 cattctgttt ggtaaaggcg caatcgctgg tttacgcgaa caaattcctc acgatgctcg
2941 cgtattgatt acctacggtg gcggcagcgt gaaaaaaacc ggcgttctcg atcaagttct
3001 ggatgccctg aaagggcatg ga
```

ETHANOLOGENIC BACTERIA WITH INCREASED RESISTANCE TO FURFURAL

RELATED APPLICATION

This application is the U.S. national phase, pursuant to 35 U.S.C. §371, of PCT international application Ser. No. PCT/US2010/020051, filed Jan. 4, 2010, designating the United States and published in English on Sep. 10, 2010 as publication WO 2010/101665 A1, which claims priority to U.S. provisional application Ser. No. 61/209,334, filed Mar. 5, 2009. The entire disclosures of the aforementioned patent applications are incorporated herein by this reference.

GOVERNMENT SPONSORED RESEARCH

This invention was made with United States Government support under Contract Nos. DE-FG02-96ER20222, DE-FG36-08GO88142, and DE-FC36-GO17058, awarded by the U.S. Department of Energy. The Government has certain rights in this invention.

SEQUENCE LISTING

The instant application contains a Sequence Listing which has been submitted via EFS-Web and is hereby incorporated by reference in its entirety. Said ASCII copy, created on Jul. 16, 2012, is named 83150US4.txt, and is 45,028 bytes in size.

BACKGROUND OF THE INVENTION

A wide variety of fermentation products can be made using sugars from lignocellulosic biomass as a substrate (Hahn-Hägerdal et al. 2006. Trends Biotechnol. 24:549-556; Jarboe et al. 2007 Adv. Biochem. Engin/Biotechnol. 108:237-261, Katahira et al. 2006 Appl. Microbiol. Biotechnol. 72:1136-1143, Tokiwa et al. 2008. Can. J. Chem. 86:548-555). Prior to fermentation, however, the carbohydrate polymers cellulose and hemicellulose must be converted to soluble sugars using a combination of chemical and enzymatic processes (Um et al. 2003 Appl Biochem Biotechnol. 105-108:115-125; Wyman et al. 2005. 96:2026-2032). Chemical processes are accompanied by side reactions that produce a mixture of minor products such as alcohols, acids, and aldehydes that have a negative effect on the metabolism of microbial biocatalysts. Alcohols (catechol, syringol, etc.) have been shown to act by permeabilizing the cell membrane and toxicity correlated well with the hydrophobicity of the molecule (Zaldivar et al. 2000 Biotechnol. Bioeng. 68:524-530). Organic acids (acetate, formate, etc.) are thought to cross the membrane in neutral form and ionize within the cytoplasm, inhibiting growth by collapsing the proton motive force (Palmqvist et al. 2000. Bioresour. Technol. 74:25-33, Zaldivar et al. 1999. Biotechnol. Bioeng. 66: 203-210). The inhibitory mechanisms of aldehydes are more complex. Aldehydes can react to form products with many cellular constituents in addition to direct physical and metabolic effects (Modig et al. 2002 Biochem. J. 363:769-776, Singh et al. 1995 Mutat. Res 337:9-17). In aggregate, these minor products from chemical pretreatments can retard cell growth and slow the fermentation of biomass-derived sugars (Horvath et al. 2001. Biotechnol. Bioeng. 75:540-549, Palmqvist et al. 2000. Bioresour. Technol. 74:17-24).

Furfural (a dehydration product of pentose sugars) is of particular importance. Furfural is a natural product of lignocellulosic decomposition. Furfural is also formed by the dehydration of pentose sugars during the depolymerization of cellulosic biomass under acidic conditions (Martinez et al. 2001 Biotechnol. Prog. 17:287-293). This compound is an important contributor to toxicity of hemicellulose syrups, and increases the toxicity of other compounds (Zaldivar et al. 1999. Biotechnol. Bioeng. 65: 24-33.). Furfural content in dilute acid hydrolysates of hemicellulose has been correlated with toxicity (Martinez et al., 2000. Biotechnol. Bioengin. 69(5): 526-536). Removal of furfural by lime addition (pH 10) rendered hydrolysates readily fermentable while re-addition of furfural restored toxicity (Martinez et al. 2001. Biotechnol Prog 17: 287-293). Furfural has also been shown to potentiate the toxicity of other compounds known to be present in acid hydrolysates of hemicellulose (Zaldivar et al. 1999. Biotechnol. Bioeng. 65: 24-33; Zaldivar et al. 1999 Biotechnol. Bioeng. 66: 203-210; Zaldivar et al. 2000 Biotechnol. Bioeng. 68:524-530). Furfural has been reported to alter DNA structure and sequence (Barciszewski et al. 1997 FEBS letters. 414:457-460, Khan et al., 1995 Cancer Lett. 89:95-99), inhibit glycolytic enzymes (Gorsich et al. 2006 Appl. Microbiol. Biotechnol. 71:339-349), and slow sugar metabolism (Hristozova et al. 2006. Enzyme Microbiol. Technol. 39:1108-1112).

Lignocellulosic biomass represents a potential feedstock for microbial conversion to renewable fuels and chemicals. Prior to fermentation, carbohydrate components (cellulose and hemicellulose) must be converted to soluble sugars using acids, enzymes, or a combination (Cheng et al. 2008 Biochem. Eng J 38:105-109; Wyman et al. 2005 Bioresour Technol. 96:2026-2032; Um et al. 2003 Appl Biochem Biotechnol 105:115-125). During steam pretreatment with mineral acids, 5-hydroxymethyl furfural (5-HMF) and furfural are produced as minor but toxic side products from the dehydration of hexose and pentose sugars, respectively (Martinez et al. 2000a Biotechnol Bioeng 69:526-536; Palmqvist and Hahn-Hagerdal 2000b Bioresour Technol 74:25-33). 5-HMF has been shown to retard growth and fermentation of ethanologenic *E. coli* (Zaldivar et al. 1999 Biotechnol Bioeng) and *Saccharomyces cerevisiae* (Almeida et al. 2008 Appl Microbiol Biotechnol 78:939-945; Palmqvist and Hahn-Hagerdal 2000a Bioresour Technol 74: 17-24; Taherzadeh et al. 2000 Appl Microbiol Biotechnol 53:701-708).

Furans can be removed from hemicellulose hydrolysates by over-liming to pH 10 at elevated temperatures (Martinez et al. 2000a Biotechnol Bioeng 69:526-536). This process requires the efficient separation of hydrolysate syrups from cellulosic fibers, specialized equipment for lime mixing, separation of syrups from insoluble calcium salts, and creates a solid waste for disposal. The development of furan-resistant biocatalysts could eliminate much of this process complexity. Several enteric bacterial genera (*Klebsiella, Enterobacter, Escherichia, Citrobacter, Edwardsiella, Proteus*) as well as yeasts have been shown to convert 5-HMF into 5-hydroxymethyl furfuryl alcohol, a less toxic compound (Boopathy et al. 1993 J Indus Microbiol 11:147-150; Palmqvist and Hahn-Hagerdal 2000a Bioresour Technol 74:17-24; Zaldivar et al. 1999 Biotechnol Bioeng 65:24-33). *S. cerevisiae* has been shown to produce multiple oxidoreductases (YGL157W, ADH6, and a mutated ADH1) that can reduce both 5-HMF and furfural to less toxic products (Almeida et al. 2008 Appl Microbiol Biotechnol 78:939-945; Almeida et al. 2009 Appl Microbiol Biotechnol 82: 625-638; Heer et al. 2009 Appl Environ Microbiol doi:10.1128/AEM.01649-9; Liu et al. 2009 Gene 446: 1-10). Increased expression of these genes was shown to be beneficial for some aspects of 5-HMF tolerance although none have been shown to increase the minimum inhibitory concentration of furfural. Gorisch et al. (2006 Appl Microbiol Biotechnol 71: 339-349) identified many gene inactivations in *S. cerevisiae* that increased sensitivity to furfural and 5-HMF. Over-expression of one gene, ZWF1 (glucose 6-phosphate dehydrogenase), increased tolerance to furfural.

The ability of fermenting organisms to function in the presence of these inhibitors has been researched extensively. Encapsulation of *Saccharomyces cerevisiae* in alginate has been shown to be protective and improve fermentation in acid hydrolysates of hemicellulose (Talebnia et al. 2006 J Biotechnol. 125:377-384.). Strains of *S. cerevisiae* have been previously described with improved resistance to hydrolysate inhibitors (Almeida et al. 2007. J. Chem. Technol. Biotechnol. 82:340-349, Martin et al. 2007. Bioresour. Technol. 98:1767-1773, Nilsson et al. 2005. Appl. Environ. Microbiol 71:7866-7871). *Escherichia coli* (Gutiérrez et al. 2006 J. Bacteriol. 121:154-164), *S. cerevisiae* (Almeida et al. 2008 Appl. Microbiol. Biotechnol. 78:939-945) and other microorganisms (Boopathy et al. 1993 J. Indust. Microbiol. 11:147-150) have been shown to contain enzymes that catalyze the reduction of furfural to the less toxic product, furfuryl alcohol (Zaldivar et al., 2000 Biotechnol. Bioeng. 68:524-530). In *E. coli*, furfural reductase activity appears to be NADPH-dependent (Gutiérrez et al. 2006. J. Bacteriol. 121:154-164). An NADPH-dependent furfural reductase was purified from *E. coli* although others may also be present. An NADPH-dependent enzyme capable of reducing 5-hydroxymethyl furfural (a dehydration product of hexose sugars) has been characterized in *S. cerevisiae* and identified as the ADH6 gene (Petersson et al. 2006. YEAST. 23:455-464).

The yqhD gene has been previously shown to encode an NADPH-dependent aldehyde oxidoreductase (Sulzenbacher et al. 2004. J. Mol. Biol. 342:489-502) that can be used for the production of propanediol (Nakamura et al. 2003. Current Opinion in Biotechnology. 14:454-459, Zhang et al. 2006 World Journal of Microbiology & Biotechnology. 22:945-952). This gene has also been shown to confer resistance to damage by reactive species of oxygen (Pérez et al. 2008. J. Biol. Chem. 283:7346-7353.). The dkgA gene has been shown to catalyze the reduction of 2,5-diketo-D-gluconic acid, a key step in the production of ascorbic acid (Habrych et al. 2002. Biotechnol. Prog. 18:257-2, Yum et al. 1999 Appl. Environ. Microbiol. 65:3341-3346). This enzyme is also thought to function in the reduction of methylglyoxal (Jeudy er al. 2006. Proteins 62:302-307, Ko et al. 2005. J. Bacteriol 187:5782-5789). The function of the yqfA gene is unknown but is proposed to be a membrane subunit of an oxidoreductase (Karp et al. 2007 Nucleic Acids Res. 35:7577-7590) which may be involved in fatty acid metabolism (McCue et al. 2001. Nucleic Acids Res. 29:774-782).

The *Escherichia coli* yqhC gene (b3010) is a predicted transcriptional regulator belonging to the AraC/XylS family of DNA-binding proteins. Inferences to date concerning the likely function of yqhC have been based solely on the similarity between the deduced protein sequence and members of the AraC/XylS family. yqhC is adjacent in the *E. coli* genome to the yqhD and dkgA genes, which are transcribed in the opposite orientation to yqhC.

The methods of the invention allow for the identification of enzymes that regulate the growth and ethanol production of microorganisms in the presence of furfural and/or 5-HMF. Accordingly, the ability to produce microorganisms that can grow and produce ethanol in the presence of furfural is extremely important for production of alternative sources of energy.

SUMMARY OF THE INVENTION

The invention relates to an isolated bacterium, wherein the bacterium has increased resistance to furfural as compared to a reference bacterium.

In one embodiment, the isolated bacterium is ethanologenic.

In another embodiment, the bacterium has increased ethanol production as compared to a reference bacterium.

In another embodiment, the expression of the yqhD gene is reduced as compared to a reference bacterium.

In another embodiment, the expression of the yqhD gene and the dkgA gene are reduced as compared to expression in a reference bacterium.

In another embodiment, the expression of the yqhC gene is reduced as compared to expression in a reference bacterium.

In another embodiment, the yqhD gene is not expressed.

In another embodiment, the yqhD gene and the dkgA gene are not expressed.

In another embodiment, the yqhC gene is not expressed.

In another embodiment, the expression of the yqhC gene is reduced as compared to a reference bacterium.

In another embodiment, the yqhC gene is deleted.

In another embodiment, the activity of the YqhD protein is reduced as compared to a reference bacterium.

In another embodiment, the activity of the YqhD protein and the activity of the DkgA protein is reduced as compared to a reference bacterium.

In another embodiment, the activity of the YqhC protein is reduced as compared to a reference bacterium.

In another embodiment, the regulation of the expression of the yqhD gene is altered as compared to a reference bacterium.

In another embodiment, the expression of the yqhD gene and regulation of expression of the dkgA gene is altered as compared to expression in a reference bacterium.

In another embodiment, the regulation of expression of the yqhC gene is altered as compared to expression in a reference bacterium.

In another embodiment, the expression of the yqhC gene is reduced as compared to a reference bacterium.

In another embodiment, the yqhC gene is deleted.

In another embodiment there is a change in the activity of the yqhD gene promoter.

In another embodiment, there is a change in the activity of the dkgA gene promoter.

In another embodiment, the level of YqhD, DkgA and/or YqhC protein is reduced due to the addition of an antisense RNA.

In another embodiment, the level of YqhD, DkgA and/or YqhC protein is reduced due to the addition of an siRNA.

The invention also relates to an isolated bacterium having reduced expression of an NADPH-dependent furfural reductase activity wherein the bacterium is capable of producing ethanol and wherein the bacterium is prepared by a process comprising growing a candidate mutant strain of the bacterium in the presence of furfural; and selecting mutants that produce ethanol in the presence of furfural.

The invention also relates to an isolated bacterium having reduced expression of an NADPH-dependent furfural reductase activity wherein the bacterium is capable of producing ethanol and wherein the bacterium is prepared by a process comprising growing a candidate strain of the bacterium in the presence of increasing concentrations of furfural; and selecting a bacterium that produces ethanol in the presence of furfural.

In another embodiment, the NADPH-dependent furfural reductase is YqhD or DkgA.

In another embodiment, the NADPH-dependent furfural reductases are YqhD and DkgA.

The invention also relates to an isolated bacterium wherein expression of the yqhD gene is reduced as compared to a reference bacterium, wherein the bacterium is capable of producing ethanol, and wherein the bacterium is prepared by a process comprising growing a candidate strain of the bacterium in the presence of furfural; and selecting a bacterium that produces ethanol in the presence of furfural.

The invention also relates to an isolated bacterium wherein expression of the yqhD gene is reduced as compared to a reference bacterium, wherein the bacterium is capable of producing ethanol, and wherein the bacterium is prepared by a process comprising growing a candidate strain of the bacterium in the presence of increasing concentrations of furfural; and selecting a bacterium that produces ethanol in the presence of furfural.

The invention also relates to an isolated bacterium wherein expression of the yqhD gene and the dkgA gene are reduced as compared to a reference bacterium, wherein the bacterium is capable of producing ethanol, and wherein the bacterium is prepared by a process comprising growing a candidate strain of the bacterium in the presence of furfural; and selecting a bacterium that produces ethanol in the presence of furfural.

The invention also relates to an isolated bacterium wherein expression of the yqhD gene and the dkgA gene are reduced as compared to a reference bacterium, wherein the bacterium is capable of producing ethanol, and wherein the bacterium is prepared by a process comprising growing a candidate strain of the bacterium in the presence of increasing concentrations of furfural; and selecting a bacterium that produces ethanol in the presence of furfural.

In one embodiment, the expression of the yqhC gene is reduced.

In another embodiment, the yqhC gene is deleted.

The invention also relates to an isolated bacterium wherein expression of the yqhC gene is reduced as compared to a reference bacterium, wherein the bacterium is capable of producing ethanol, and wherein the bacterium is prepared by a process comprising growing a candidate strain of the bacterium in the presence of furfural; and selecting a bacterium that produces ethanol in the presence of furfural.

The invention also relates to an isolated bacterium wherein expression of the yqhC gene is reduced as compared to a reference bacterium, wherein the bacterium is capable of producing ethanol, and wherein the bacterium is prepared by a process comprising growing a candidate strain of the bacterium in the presence of increasing concentrations of furfural; and selecting a bacterium that produces ethanol in the presence of furfural.

The invention also relates to an isolated bacterium having reduced expression of an NADPH-dependent furfural reductase activity wherein the bacterium produces ethanol, wherein the bacterium is prepared by a process comprising reducing the expression of the yqhD gene; growing a candidate strain of the bacterium in the presence of furfural; and selecting a bacterium that produces ethanol in the presence of furfural.

The invention also relates to an isolated bacterium having reduced expression of an NADPH-dependent furfural reductase activity wherein the bacterium produces ethanol, wherein the bacterium is prepared by a process comprising reducing the expression of the yqhD gene and the dkgA gene; growing a candidate strain of the bacterium in the presence of furfural; and selecting a bacterium that produces ethanol in the presence of furfural.

In one embodiment, expression of the yqhC gene is reduced.

In another embodiment, the yqhC gene is deleted.

The invention also relates to an isolated bacterium having reduced expression of an NADPH-dependent furfural reductase activity wherein the bacterium produces ethanol, wherein the bacterium is prepared by a process comprising reducing the expression of the yqhC gene; growing a candidate strain of the bacterium in the presence of furfural; and selecting a bacterium that produces ethanol in the presence of furfural.

The invention also relates to an isolated bacterium having reduced expression of the yqhD gene, wherein the bacterium is capable of producing ethanol, and wherein the bacterium is prepared by reducing the expression of the yqhD gene, growing a candidate strain of the bacterium in the presence of furfural; and selecting a bacterium that produces ethanol in the presence of furfural.

The invention also relates to an isolated bacterium having reduced expression of the yqhD gene and the dkgA gene, wherein the bacterium is capable of producing ethanol, and wherein the bacterium is prepared by reducing the expression of the yqhD gene and the dkgA gene, growing a candidate strain of the bacterium in the presence of furfural; and selecting a bacterium that produces ethanol in the presence of furfural.

In one embodiment, the expression of the yqhC gene is reduced.

In another embodiment, the yqhC gene is deleted.

The invention also relates to an isolated bacterium having reduced expression of the yqhC gene, wherein the bacterium is capable of producing ethanol, and wherein the bacterium is prepared by reducing the expression of the yqhC gene, growing a candidate strain of the bacterium in the presence of furfural; and selecting a bacterium that produces ethanol in the presence of furfural.

The invention also relates to an isolated bacterium wherein the activity of the YqhD protein is reduced or eliminated as compared to a reference bacterium, wherein the bacterium is capable of producing ethanol, wherein the bacterium is prepared by growing a candidate strain of the bacterium in the presence of furfural; and selecting a bacterium that produces ethanol in the presence of furfural.

The invention also relates to an isolated bacterium wherein the activity of the YqhD protein is reduced as compared to a reference bacterium, wherein the bacterium is capable of producing ethanol, wherein the bacterium is prepared by growing a candidate strain of the bacterium in the presence of increasing concentrations of furfural; and selecting a bacterium that produces ethanol in the presence of furfural.

The invention also relates to an isolated bacterium wherein the activity of the YqhD protein and the DkgA protein is reduced or eliminated as compared to a reference bacterium, wherein the bacterium is capable of producing ethanol, wherein the bacterium is prepared by growing a candidate strain of the bacterium in the presence of a furfural; and selecting a bacterium that produces ethanol in the presence of furfural.

The invention also relates to an isolated bacterium wherein the activity of the YqhD protein and the DkgA protein is reduced as compared to a reference bacterium, wherein the bacterium is capable of producing ethanol, wherein the bacterium is prepared by growing a candidate strain of the bacterium in the presence of increasing concentrations of furfural; and selecting a bacterium that produces ethanol in the presence of furfural.

In one embodiment, the expression of the yqhC gene is reduced.

In another embodiment, the yqhC gene is deleted.

The invention also relates to an isolated bacterium wherein the activity of the YqhC protein is reduced or eliminated as compared to a reference bacterium, wherein the bacterium is capable of producing ethanol, wherein the bacterium is prepared by growing a candidate strain of the bacterium in the presence of furfural; and selecting a bacterium that produces ethanol in the presence of furfural.

The invention also relates to an isolated bacterium wherein the activity of the YqhC protein is reduced as compared to a reference bacterium, wherein the bacterium is capable of producing ethanol, wherein the bacterium is prepared by growing a candidate strain of the bacterium in the presence of increasing concentrations of furfural and selecting a bacterium that produces ethanol in the presence of furfural.

In one embodiment, the bacterium has increased ethanol production in the presence of furfural as compared to a reference bacterium.

In another embodiment, the bacterium has increased ethanol production in the presence of 5-hydroxymethylfurfural (5-HMF) as compared to a reference bacterium.

In another embodiment, the bacterium has increased ethanol production in the presence an aldehyde selected from the group consisting of: acetaldehyde, propionaldehyde, butyraldehyde, and cinnamaldehyde, as compared to a reference bacterium.

In another embodiment, the bacterium has increased ethanol production in the presence of methylglyoxal, as compared to a reference bacterium.

In another embodiment, the bacterium has increased ethanol production when the level of reductive removal of furfural is reduced as compared to a reference bacterium.

In another embodiment, the bacterium has reduced furfural metabolism as compared to a reference bacterium.

In another embodiment, the bacterium has no detectable furfural metabolism.

In another embodiment, the bacterium has increased growth as compared to a reference bacterium.

In another embodiment, the bacterium has increased growth in the presence of furfural as compared to a reference bacterium.

In another embodiment, the bacterium has increased growth and increased ethanol production in the presence of furfural as compared to a reference bacterium.

In another embodiment, the bacterium has increased growth in the presence of 5-HMF as compared to a reference bacterium.

In another embodiment, the bacterium has increased growth and increased ethanol production in the presence of 5-HMF as compared to a reference bacterium.

In another embodiment, the bacterium has reduced furfural reductase activity as compared to a reference bacterium.

In another embodiment, the bacterium has a reduced rate of 5-HMF dependent oxidation of NADPH.

In another embodiment, the expression of the yqhC gene is reduced due to the insertion of IS10 in the yqhC gene.

In another embodiment, the bacterium has increased growth in the presence of hydrolysate as compared to a reference bacterium.

In another embodiment, the hydrolysate is derived from a biomass, a hemicellulosic biomass, a lignocellulosic biomass or a cellulosic biomass.

In another embodiment, the bacterium produces ethanol as the primary fermentation product.

In another embodiment, the isolated bacterium of the invention produce ethanol under anaerobic conditions.

In another embodiment, ethanol is produced under microaerobic conditions.

In another embodiment, the bacterium is non-recombinant.
In another embodiment, the bacterium is recombinant.
In another embodiment, the bacterium is Gram-negative.
In another embodiment, the bacterium is Gram-positive.
In another embodiment, the Gram-negative bacterium is selected from the group consisting of *Acinetobacter, Gluconobacter, Zymomonas, Escherichia, Geobacter, Shewanella, Salmonella, Enterobacter* and *Klebsiella*.

In another embodiment, the Gram-positive bacterium is selected from the group consisting of *Bacillus, Clostridium, Corynebacterium, Lactobacillus, Lactococcus, Oenococcus, Streptococcus* and *Eubacterium*.

In another embodiment, the bacterium is *Escherichia coli*.
In another embodiment, the isolated bacterium of the invention is *Klebsiella oxytoca*.

In another embodiment, the bacterium is *E. coli* strain EMFR9.

The invention also relates to a method for producing ethanol from a biomass, a hemicellulosic biomass, a lignocellulosic biomass, a cellulosic biomass or an oligosaccharide source comprising contacting the biomass, hemicellulosic biomass, lignocellulosic biomass, cellulosic biomass or oligosaccharide with the isolated bacterium of the invention, thereby producing ethanol from a biomass, hemicellulosic biomass, lignocellulosic biomass, cellulosic biomass or an oligosaccharide source.

The invention also relates to a method for producing ethanol from a biomass, a hemicellulosic biomass, a lignocellulosic biomass, a cellulosic biomass or an oligosaccharide source in the presence of furfural comprising contacting the biomass, hemicellulosic biomass, lignocellulosic biomass, cellulosic biomass or oligosaccharide with the isolated bacterium of the invention, thereby producing ethanol from a biomass, hemicellulosic biomass, lignocellulosic biomass, cellulosic biomass or an oligosaccharide source.

The invention also relates to a kit comprising any of the isolated bacterium of any the invention.

The invention also relates to an *E. coli* strain LY180 represented by a deposit with the Agricultural Research Culture Collection designated as deposit number NRRL B-50239.

The invention also relates to ethanol produced by the methods of ethanol production of the invention.

The invention also relates to a microarray comprising genes that exhibit an increase or decrease in expression in the absence of the yqhC gene.

The invention also relates to an isolated yqhD promoter comprising the sequence presented in FIG. 28 and fragments and mutants or variants thereof.

The invention also relates to the use of the yqhD promoter to regulate expression of a gene in the presence of at least one of furfural, 5-HMF, acetaldehyde, propionaldehyde, butyraldehyde, cinnamaldehyde, and methylglyoxal, as compared to a reference bacterium.

An isolated bacterium, wherein the bacterium has increased resistance to furfural as compared to a reference bacterium and wherein expression and/or activity of an NADPH-dependent oxidoreductase is reduced as compared to a reference bacterium.

In one embodiment, the isolated bacterium wherein the NADPH-dependent oxidoreductase has a Km that is less than or equal to the Km of YqhD and/or the Km of DkgA.

The invention also provides a method of increasing the resistance or tolerance of a bacterium to furfural or 5-HMF by reducing the expression and/or activity of an NADPH-dependent oxidoreductase.

The invention also provides a method of identifying an NADPH-dependent oxidoreductase that increases the resistance or tolerance of a bacterium to furfural or 5-HMF by reducing the expression and/activity of an NADPH-dependent oxidoreductase.

The invention also relates to increasing the growth of a bacterium in the presence of furfural or 5-HMF by reducing the expression and/or activity of an NADPH-dependent oxidoreductase.

The invention also relates to increasing the production of ethanol by a bacterium in the presence of furfural or 5-HMF by reducing the expression and/or activity of an NADPH-dependent oxidoreductase.

According to the methods, the NADPH-dependent oxidoreductase has a Km that is less than or equal to the Km of YqhD or DkgA.

In one embodiment, the preferred substrate for the NADPH-dependent oxidoreductase is NADPH and not NADH.

In another embodiment, the substrate for the NADPH-dependent oxidoreductase is NADPH and not NADH.

The invention also relates to an *E. coli* strain EMFR9 represented by a deposit with the Agricultural Research Culture Collection designated as deposit number NRRL B-50240.

The invention also relates to an *E. coli* strain EMFR17 represented by a deposit with the Agricultural Research Culture Collection designated as deposit number NRRL B-50241.

The invention also relates to an *E. coli* strain EMFR26 represented by a deposit with the Agricultural Research Culture Collection designated as deposit number NRRL B-50242.

The invention also relates to an *E. coli* strain EMFR35 represented by a deposit with the Agricultural Research Culture Collection designated as deposit number NRRL B-50243.

BRIEF DESCRIPTION OF THE DRAWINGS

FIGS. 7A-B. Effect of hemicellulose hydrolysate on growth (A) and ethanol production (B). Symbols for all: ■, LY180 (dashed line); and ▲, EMFR9 (solid line) after incubation for 48 hours.

FIGS. 10A-D. Growth of LY180 and LY180ΔyqhC in the presence of furfural. Plots of cell density (optical density) versus time of incubation in hours are shown. A. Growth of LY180 in AM1-5% xylose medium with 0, 0.5, 1, 1.5, and 2 g/L furfural. B. LY180ΔyqhC. C. LY180ΔyqhC carrying a single copy plasmid pYqhC with the wild type yqhC gene under its natural promoter. D. LY180ΔyqhC carrying an empty vector pCC1.

FIGS. 16A-B. Presents the YqhD amino acid (A) (SEQ ID NO: 65) and nucleic acid (B) (SEQ ID NO: 66) sequences.

FIGS. 17A-B. Presents the DkgA amino acid (A) (SEQ ID NO: 67) and nucleic acid (B) (SEQ ID NO: 68) sequences.

FIG. 18A-B. Presents the YqhC amino acid (A) (SEQ ID NO: 69) and nucleic acid (B) (SEQ ID NO: 70) sequences.

FIG. 19. Arrangement of the yqhC-yqhD-dkgA genes and surrounding regions in LY180 and EMFR9. The locations and directions of the coding regions for yqhC, yqhD and dkgA are shown in the ethanologenic strain LY180 (top line) and in the furfural resistant derivative EMFR9 (lower line). The flanking genes to the left of yqhC (metC and yghB) and to the right of dkgA (yqhG, yqhH and ygiQ) are shown for LY180. IS10 is present within the yqhC gene of EMFR9. Known promoters are shown by arrows (solid lines) based on information available at EcoCyc (Keseler et al. 2009 Nucleic Acids Res. 37: D464-D470). The promoter upstream from yqhD is shown by an arrow with a dotted line.

FIG. 23. Arrangement of yqhC orthologs in the genomes of selected bacteria. The arrangement of genes surrounding yqhC is shown for *Escherichia coli* K12 (bottom line), and for a selection of genera containing a yqhC ortholog. The yqhC ortholog in each genome has a bold outline and cross-hatching. YqhD orthologs where present are indicated by "yqhD" in parentheses above the gene, and dkgA orthologs by (dkgA). The numbers below the genes represent the coordinates in the genomes. The alignment of the genomes and detection of orthologs was created using the EcoCyc multigenome browser.

FIG. 24A-F. Effect of 5-HMF on anaerobic growth and fermentation. Cells were grown in AM1 mineral salts media with xylose (100 g l$^{-1}$ xylose). A. Cell mass during growth with 1.0 g l$^{-1}$ 5-HMF; B. Ethanol production during fermentation with 1.0 g l$^{-1}$ 5-HMF; C. Reduction of 5-HMF (1.0 g l$^{-1}$) during fermentation; D. Cell mass during growth with 2.5 g l$^{-1}$ 5-HMF; E. Ethanol production during fermentation with 2.5 g l$^{-1}$ 5-HMF; F. Reduction of 5-HMF (2.5 g l$^{-1}$ 5-HMF) during fermentation. Parallel fermentations without 5-HMF are included (dashed lines) in panels A and B for comparison. All data are plotted as a mean with standard deviation (n=3). Symbols for all: □, LY180; and ●, EMFR9.

FIG. 29. Presents the yqhC-yqhD-dkgA region from LY180 (A) (SEQ ID NO: 73) and EMFR9 (B) (SEQ ID NO: 74).

DETAILED DESCRIPTION OF THE INVENTION

I. Definitions

Figure 1A:
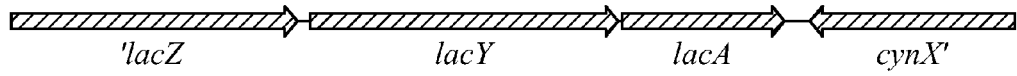
FIG. 1. Linear DNA fragments used in construction of LY180.
Figure 1B:
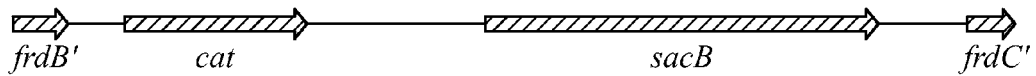
Figure 1C:
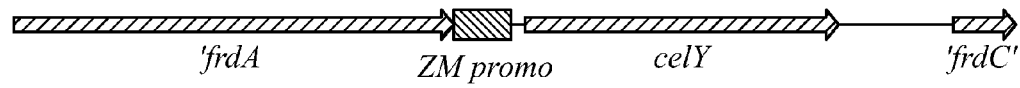
Figure 1D:
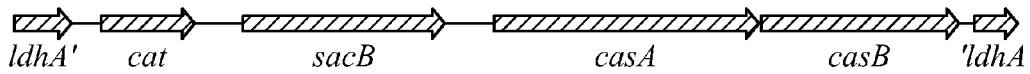
Figure 1E:
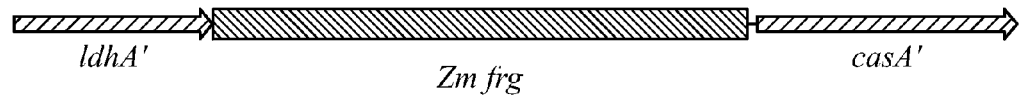

As used herein, "isolated" means partially or completely free from contamination by other bacteria. An isolated bacterium can exist in the presence of a small fraction of other bacteria which do not interfere with the properties and function of the isolated bacterium. An isolated bacterium will generally be at least 30%, 40%, 50%, 60%, 70%, 80%, 85%, 90%, 95%, 98%, or 99% pure. Preferably, an isolated bacterium according to the invention will be at least 98% or at least 99% pure.

As used herein, "bacterium" may include "non-recombinant bacterium" "recombinant bacterium" and "mutant bacterium".

As used herein, "non-recombinant bacterium" includes a bacterial cell that does not contain heterologous polynucleotide sequences, and is suitable for further modification using the compositions and methods of the invention, e.g. suitable for genetic manipulation, e.g., which can incorporate heterologous polynucleotide sequences, e.g., which can be transfected. The term is intended to include progeny of the cell originally transfected. In particular embodiments, the cell is a Gram-negative bacterial cell or a Gram-positive cell.

As used herein, "recombinant" as it refers to bacterium, means a bacterial cell that contains a heterologous polynucleotide sequence, or that has been treated such that a native polynucleotide sequence has been mutated or deleted.

As used herein, "mutant" as it refers to bacterium, means a bacterial cell that is not identical to a reference bacterium, as defined herein below.

A "mutant" bacterium includes a "recombinant" bacterium.

As used herein, "ethanologenic" means the ability of a bacterium to produce ethanol from a carbohydrate as a primary fermentation product. The term is intended to include naturally occurring ethanologenic organisms and ethanologenic organisms with naturally occurring or induced mutations or ethanologenic organisms with genetic alterations.

The term "non-ethanologenic" means the inability of a bacterium to produce ethanol from a carbohydrate as a primary fermentation product. The term is intended to include microorganisms that produce ethanol as the minor fermentation product comprising less than about 40% of total non-gaseous fermentation products.

As used herein, "ethanol production" means the production of ethanol from a carbohydrate as a primary fermentation product.

As used herein, "capable of producing ethanol" means capable of "ethanol production" as defined herein.

The terms "fermenting" and "fermentation" mean the degradation or depolymerization of a complex sugar and bioconversion of that sugar residue into ethanol, acetate and succinate. The terms are intended to include the enzymatic process (e.g. cellular or acellular, e.g. a lysate or purified polypeptide mixture) by which ethanol is produced from a carbohydrate, in particular, as a primary product of fermentation.

The terms "primary fermentation product" and "major fermentation product" are used herein interchangeably and are intended to include non-gaseous products of fermentation that comprise greater than about 50% of total non-gaseous product. The primary fermentation product is the most abundant non-gaseous product. In certain embodiments of the invention, the primary fermentation product is ethanol.

The term "minor fermentation product" as used herein is intended to include non-gaseous products of fermentation that comprise less than 40% of total non-gaseous product. In certain embodiments of the invention, the minor fermentation product is ethanol.

The term "sugar" is intended to include any carbohydrate source comprising a sugar molecule(s). Such sugars are potential sources of sugars for depolymerization (if required) and subsequent bioconversion to acetaldehyde and subsequently to ethanol by fermentation according to the products and methods of the present invention. Sources of sugar include starch, the chief form of fuel storage in most plants, hemicellulose, and cellulose, the main extracellular structural component of the rigid cell walls and the fibrous and woody tissues of plants. The term is intended to include monosaccharides, also called simple sugars, oligosaccharides and polysaccharides. In certain embodiments, sugars include, e.g., glucose, xylose, arabinose, mannose, galactose, sucrose, and lactose. In other embodiments, the sugar is glucose.

As used herein, "YqhD" means an NADPH-dependent aldehyde oxidoreductase. yqhD refers to an NADPH-dependent aldehyde oxidoreductase gene whereas the term YqhD refers to a yqhD gene product. The nucleic and amino acid sequence of the yqhD gene and the YqhD polypeptide are presented in FIG. 16.

As used herein, "DkgA" means an enzyme that catalyzes the reduction of 2,5-diketo-D-gluconic acid. DkgA also means an enzyme that functions in the reduction of methylglyoxal. dkgA refers to the gene corresponding to an enzyme that catalyzes the reduction of 2,5-diketo-D-gluconic acid whereas the term DkgA refers to a dkgA gene product. The nucleic acid and the amino acid sequence of the dkgA gene and the DkgA polypeptide are presented in FIG. 17.

As used herein, "YqhC" means a transcriptional regulator, transcriptional regulator protein, or the gene product expressed from the transcriptional regulator gene. yqhC refers to the gene corresponding to a transcriptional regulator whereas the term YqhC refers to a yqhC gene product. The nucleic acid and amino acid sequence of the yqhC gene and the YqhC polypeptide are presented in FIG. 18.

As used herein, "mutant nucleic acid molecule" or "mutant gene" is intended to include a nucleic acid molecule or gene having a nucleotide sequence which includes at least one alteration (e.g., substitution, insertion, deletion) such that the polypeptide or polypeptide that can be encoded by the mutant exhibits an activity or property that differs from the polypeptide encoded by the wild-type nucleic acid molecule or gene, or wherein a polypeptide is not produced from the mutant gene.

As used herein, "mutation" as it refers to a nucleic acid molecule or gene means deletion of a nucleic acid or a gene, or a decrease in the level of expression of a nucleic acid or a gene, wherein the deletion or decrease in expression results in a deletion or decrease in the expression of the polypeptide that can be encoded by the nucleic acid molecule or gene. A mutation also means a nucleic acid molecule or gene having a nucleotide sequence which includes at least one alteration (e.g., substitution, insertion, deletion) such that the polypeptide that can be encoded by the mutant exhibits an activity or property that differs from the polypeptide encoded by the wild-type nucleic acid molecule or gene.

As used herein, "mutant protein" or "mutant protein or amino acid sequence" is intended to include an amino acid sequence which includes at least one alteration (e.g., substitution, insertion, deletion) such that the polypeptide or polypeptide that can be encoded by the mutant amino acid sequence exhibits an activity or property that differs from the polypeptide encoded by the wild-type amino acid sequence.

As used herein, "mutation" as it refers to a protein or amino acid sequence means deletion of an amino acid of an amino acid sequence, or a decrease in the level of expression of an amino acid sequence, wherein the deletion or decrease in expression results in a deletion or decrease in the expression of the polypeptide that can be encoded by an amino acid sequence. A mutation also means a protein or amino acid sequence having an amino acid sequence which includes at least one alteration (e.g., substitution, insertion, deletion) such that the polypeptide or polypeptide that can be encoded by the mutant exhibits an activity or property that differs from the polypeptide or polypeptide encoded by the wild-type amino acid sequence.

As used herein, "fragment" or "subsequence" is intended to include a portion of parental or reference nucleic acid sequence or amino acid sequence, or a portion of polypeptide or gene which encodes or retains a biological function or property of the parental or reference sequence, polypeptide or gene.

As used herein, "a portion" means exhibits at least 50% of the reference nucleic acid, amino acid sequence, polypeptide or gene (for example, 50, 55, 60, 65, 70, 75, 80, 85, 90, 91, 92, 93, 94, 95, 96, 97, 98, 99 or 100%) of the function or property of a parental or reference nucleic acid sequence, amino acid sequence, polypeptide or gene.

As used herein, "retains" (for example retains a biological function or property) means exhibits at least 50% (for example, 50, 55, 60, 65, 70, 75, 80, 85, 90, 91, 92, 93, 94, 95, 96, 97, 98, 99 or 100%) of the function or property of a parental or reference sequence, polypeptide or gene.

A "mutant" bacterium includes a bacterium comprising a "mutation" as defined hereinabove.

As used herein, "reference" or "reference bacterium" includes, at least, a wild-type bacterium or a parental bacterium.

As used herein, "wild-type" means the typical form of an organism or strain, for example a bacterium, gene, or characteristic as it occurs in nature, in the absence of mutations. "Wild type" refers to the most common phenotype in the natural population. Wild type is the standard of reference for the genotype and phenotype.

As used herein, "parental" or "parental bacterium" refers to the bacterium that gives rise to a bacterium of interest.

A "gene," as used herein, is a nucleic acid that can direct synthesis of an enzyme or other polypeptide molecule, e.g., can comprise coding sequences, for example, a contiguous open reading frame (ORF) that encodes a polypeptide, a subsequence or fragment thereof, or can itself be functional in the organism. A gene in an organism can be clustered in an operon, as defined herein, wherein the operon is separated from other genes and/or operons by intergenic DNA. Individual genes contained within an operon can overlap without intergenic DNA between the individual genes. In addition, the term "gene" is intended to include a specific gene for a selected purpose. A gene can be endogenous to the host cell or can be recombinantly introduced into the host cell, e.g., as a plasmid maintained episomally or a plasmid (or fragment thereof) that is stably integrated into the genome. A heterologous gene is a gene that is introduced into a cell and is not native to the cell.

The term "nucleic acid" is intended to include nucleic acid molecules, e.g., polynucleotides which include an open reading frame encoding a polypeptide, a subsequence or fragment thereof, and can further include non-coding regulatory sequences, and introns. In addition, the terms are intended to include one or more genes that map to a functional locus. In addition, the terms are intended to include a specific gene for a selected purpose. In one embodiment, the term gene includes any gene encoding a furfural reductase, for example an NADPH-dependent furfural reductase, including but not limited to yqhD and dkgA. In one embodiment, the gene or polynucleotide fragment is involved in at least one step in the bioconversion of a carbohydrate to ethanol. A gene in an organism can be clustered in an operon, as defined herein, wherein the operon is separated from other genes and/or operons by intergenic DNA.

As used herein, "increasing" or "increases" or "increased" refers to increasing by at least 5%, for example, 5, 6, 7, 8, 9, 10, 15, 20, 25, 30, 35, 40, 45, 50, 55, 60, 65, 70, 75, 80, 85, 90, 95, 99, 100% or more, for example, as compared to the level of expression of the yqhD, dkgA and/or yqhC gene(s) in a furfural resistant bacterium, as compared to a reference bacterium.

As used herein, "increasing" or "increases" or "increased" also means increases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of expression of the yqhD, dkgA and/or yqhC gene(s) in a furfural resistant bacterium, as compared to a reference bacterium.

As used herein, "decreasing" or "decreases" or "decreased" or "reduced" or "reducing" refers to decreasing or reducing by at least 5%, for example, 5, 6, 7, 8, 9, 10, 15, 20, 25, 30, 35, 40, 45, 50, 55, 60, 65, 70, 75, 80, 85, 90, 95, 99 or 100%, for example, as compared to the level of expression of the yqhD, dkgA and/or yqhC gene(s) in a furfural resistant bacterium, as compared to a reference bacterium.

As used herein, "decreasing" or "decreases" or "decreased" or "reduced" or "reducing" also means decreases or reduces by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of expression of the yqhD, dkgA and/or yqhC gene(s) in a furfural resistant bacterium, as compared to a reference bacterium.

"Decreased" or "reduced" also means eliminated such that there is no detectable level of activity, expression, etc., for example no detectable level of expression of the yqhD, dkgA and/or yqhC gene[s] or no detectable activity of the YqhD, DkgA and/or YqhC protein[s].

As used herein, "activity" refers to the activity of a gene, for example the level of transcription of a gene. "Activity" also refers to the activity of an mRNA, for example, the level of translation of an mRNA. "Activity" also refers to the activity of a protein, for example YqhD or DkgA or YqhC.

An "increase in activity" includes an increase in the rate and/or the level of activity.

As used herein, "expression" as in "expression of yqhD" or "expression of dkgA" or "expression of yqhC" refers to the expression of the protein product of the yqhD gene, the dkgA gene, and the yqhC gene, respectively.

As used herein, "expression" as in "expression of yqhD" or "expression of dkgA" or "expression of yqhC" also refers to the expression of detectable levels of the mRNA transcript corresponding to the yqhD gene, the dkgA gene, and the yqhC gene, respectively.

"Altering", as it refers to expression levels, means decreasing or increasing expression of a gene, mRNA or protein of interest, for example yqhD, dkgA or yqhC.

"Altering", as it refers to activity, means decreasing or increasing activity of a protein of interest, for example YqhD, DdkgA or YqhC.

As used herein, "not expressed" means there are no detectable levels of the product of a gene or mRNA of interest, for example, yqhD, dkgA or yqhC.

As used herein "eliminate" means decrease to a level that is undetectable.

As used herein, "resistance to furfural" means the ability of a mutant ethanologenic bacterium to grow or produce ethanol in the presence of furfural, for example furfural at a concentration of 0.1 g liter$^{-1}$ or more (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4, 4.5, 5, 5.5, 6, 6.5, 7, 7.5, 8, 8.5, 9, 9.5, 10 g liter$^{-1}$ or more). Resistance to furfural also means the ability of an ethanologenic bacterium to grow or produce ethanol in the presence of furfural at a level that is increased as compared to the level of growth or ethanol production by a wild-type bacterium or a parental bacterium.

As used herein, "in the presence of" as it applies to the presence of furfural, means maintenance of a bacterium in the presence of at least 0.1 g liter$^{-1}$ or more (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4, 4.5, 5, 5.5, 6, 6.5, 7, 7.5, 8, 8.5, 9, 9.5, 10 g liter$^{-1}$ or more) of furfural.

As used herein, "in the absence of" as it applies to the absence of furfural means maintenance of a bacterium in media that contains 0.1 g liter$^{-1}$ or less, including no detectable level, of furfural.

As used herein, "reductive removal of furfural" means the removal of furfural by the action of a furfural reductase, for example an NADPH-dependent furfural reductase, including but not limited to YqhD and DkgA. This can also be accomplished by addition of a nucleic acid encoding YqhD or DkgA.

As used herein, "furfural metabolism" means the breakdown of furfural to any one of furfural alcohol, furoic acid, 2-ketoglutaric acid, and acetic acid.

As used herein, "5-HMF" means 5-hydroxymethyl furfural.

As used herein, "resistance to 5-HMF" means the ability of a mutant ethanologenic bacterium to grow or produce ethanol in the presence of 5-HMF, for example 5-HMF at a concentration of 0.1 g liter$^{-1}$ or more (e.g. 0.1, 0.5, 1.0, 1.5, 2.0, 2.5, 3.0, 3.5, 4, 4.5, 5, 5.5, 6, 6.5, 7, 7.5, 8, 8.5, 9, 9.5, 10 g liter$^{-1}$ or more). Resistance to 5-HMF also means the ability of an ethanologenic bacterium to grow or produce ethanol in the presence of 5-HMF at a level that is increased as compared to the level of growth or ethanol production by a wild-type bacterium or a parental bacterium.

As used herein, "in the presence of" as it applies to the presence of 5-HMF, means maintenance of a bacterium in the presence of at least 0.1 g liter$^{-1}$ or more (e.g. 0.1, 0.5, 1.0, 1.5, 2.0, 2.5, 3.0, 3.5, 4, 4.5, 5, 5.5, 6, 6.5, 7, 7.5, 8, 8.5, 9, 9.5, 10 g liter$^{-1}$ or more) of 5-HMF.

As used herein, "in the absence of" as it applies to the absence of 5-HMF means maintenance of a bacterium in media that contains 0.1 g liter$^{-1}$ or less (e.g., 0.1, 0.09, 0.08. 0.07, 0.06, 0.05, 0.01, 0.005, 0.001 g liter$^{-1}$ or less) including no detectable level, of 5-HMF.

As used herein, "growth" means an increase, as defined herein, in the number or mass of a bacterium over time.

As used herein, "furfural reductase" means an enzyme that converts toxic furfural to less toxic furfural alcohol, for example an NADPH-dependent furfural reductase, including but not limited to YqhD and DkgA.

As used herein, "hemicellulose hydrolysate" includes but is not limited to hydrolysate derived from a biomass, a hemicellulosic biomass, a lignocellulosic biomass or a cellulosic biomass.

As used herein, "derived from" means originates from.

The term "Gram-negative bacterium" is intended to include the art-recognized definition of this term. Exemplary Gram-negative bacteria include *Acinetobacter, Gluconobacter, Zymomonas, Escherichia, Geobacter, Shewanella, Salmonella, Enterobacter* and *Klebsiella*.

The term "Gram-positive bacterium" is intended to include the art-recognized definition of this term. Exemplary Gram-positive bacteria include *Bacillus, Clostridium, Corynebacterium, Lactobacillus, Lactococcus, Oenococcus, Streptococcus* and *Eubacterium*.

The term "amino acid" is intended to include the 20 alpha-amino acids that regularly occur in proteins. Basic charged amino acids include arginine, asparagine, glutamine, histidine and lysine. Neutral charged amino acids include alanine, cysteine, glycine, isoleucine, leucine, methionine, phenylalanine, proline, serine, threonine, tryptophan, tyrosine, and valine. Acidic amino acids include aspartic acid and glutamic acid.

As used herein, "selecting" refers to the process of determining that an identified bacterium produces ethanol in the presence of furfural.

As used herein, "identifying" refers to the process of assessing a bacterium and determining that the bacterium produces ethanol in the presence of furfural.

As used herein, "increasing concentrations of furfural" means increments from 0 to 5 g/L, for example 1 μg/Liter increments, 1 mg per liter increments or 1 g/L increments.

As used herein, "selecting" refers to the process of determining that an identified bacterium produces ethanol in the presence of 5-HMF.

As used herein, "identifying" refers to the process of assessing a bacterium and determining that the bacterium produces ethanol in the presence of 5-HMF.

As used herein, "increasing concentrations of 5-HMF" means increments from 0 to 5 g/L, for example 1 μg/Liter increments, 1 mg per liter increments or 1 g/L increments.

As used herein, "regulation of a promoter" refers to increasing or decreasing, as defined herein, the activity of a promoter.

As used herein, "deleting" or "knocking out" or "inactivating" means reducing to a level that is non-detectable. "Deleting" or "knocking out" or "inactivating" as it refers to a gene means removing a gene such that the gene is no longer detectable by assays known in the art, for example, PCR or Southern blot analysis, or such that the mRNA corresponding to the gene is no longer detectable by assays known in the art, for example, PCR or Northern blot analysis, or that the encoded protein is no longer detectable or functional by assays known in the art, for example, Western blot analysis, SDS-PAGE or enzymatic assays.

As used herein, a gene that is "deleted" or "knocked out" or "inactive" means a gene that has no detectable level of expression according to methods know in the art.

Methods of gene inactivation include RNA interference using siRNA or antisense methods.

As used herein, the term "siRNA" refers to a double stranded nucleic acid in which each strand comprises RNA, RNA analog(s) or RNA and DNA. Typically, the antisense strand of the siRNA is sufficiently complementary with a target sequence of the gene/RNA of interest to decrease or inactivate the expression of the gene.

By "antisense" is meant a nucleotide sequence having complementarity to a target nucleic acid sequence.

RNAs are the direct products of genes, and these small RNAs can bind to specific target RNAs and either increase or decrease their activity. Particularly, the antisense strand binds to the complementary mRNA, thereby preventing protein production.

In this disclosure, "comprises," "comprising," "containing" and "having" and the like have the open-ended meaning ascribed to them in U.S. Patent law and mean "includes," "including," and the like.

II. Bacteria

The invention relates to bacteria that are resistant to furfural and/or 5-HMF. The invention provides for both non-recombinant, and recombinant bacteria.

The invention provides isolated bacterium that have an increased resistance to furfural and/or 5-HMF as compared to a reference bacterium. The bacteria of the invention includes bacterium that are ethanologenic and/or exhibit increased ethanol production as compared to a reference bacterium.

In one aspect, expression of yqhD, yqhC and/or dkgA are decreased or eliminated in the bacterium of the invention, as compared to expression in a reference bacterium.

Expression is decreased by methods known in the art, including but not limited to altering a promoter that regulates yqhD, yqhC and/or dkgA expression as compared to a reference bacterium. For example, the promoter is altered by art-accepted methods including but not limited to deletion of the promoter, replacement of the promoter by a different promoter, modification of the promoter (e.g. by inserting, substituting or removing nucleic acids or by inserting or removing regulatory elements or motifs in the promoter).

In one embodiment, expression is decreased or eliminated by altering or deleting the yqhC gene.

In another aspect the activity of YqhD, YqhC and/or DkgA protein is decreased or altered in the bacterium of the invention, as compared to the activity of YqhD, YqhC and/or DkgA protein in a reference bacterium. Activity is decreased or altered by methods known in the art, including but not limited to modification of the yqhD, yqhC and/or dkgA gene(s) (e.g. by inserting, substituting or removing nucleic acids or amino acids in the sequences encoding the genes).

The invention also provides for a bacterium wherein expression of the yqhD, yqhC and/or dkgA gene is/are decreased as compared to the expression of the yqhD, yqhC and/or dkgA gene in a reference bacterium, and regulation of the yqhD, yqhC and/or dkgA gene is altered as compared to the regulation of the yqhD or yqhD and dkgA gene in a reference bacterium. Expression is decreased or altered by methods known in the art, including but not limited to modification of the yqhD, yqhC and/or dkgA gene(s) (e.g. by inserting, substituting or removing nucleic acids or amino acids in the sequences encoding the genes).

The invention provides for a bacterium wherein the yqhD, yqhC and/or dkgA gene(s) is/are inactivated or knocked out as compared to a reference bacterium.

Gene expression can be altered by any mechanism known in the art including but not limited to mechanisms of anti-sense inhibition or anti-sense transcription.

The invention provides for methods of altering regulation of the yqhD, yqhC and/or dkgA gene(s), by methods known in the art, including but not limited to placing the yqhD, yqhC and/or dkgA gene(s) under the control of a different promoter or under the control of an additional promoter as compared to the reference bacterium.

The invention provides for methods of altering regulation of the yqhD, yqhC and/or dkgA gene(s), by methods known in the art, including but not limited to placing the yqhD, yqhC and/or dkgA gene(s) under the control of a different regulatory protein or under the control of an additional regulatory protein as compared to the reference bacterium. In one embodiment, the regulatory protein is a repressor. In an alternative embodiment, the regulatory protein is an inducer.

The invention also provides for methods of regulating or altering regulation of the yqhD or yqhD and dkgA gene(s) by altering or deleting the yqhC gene as compared to a reference bacterium.

The invention also provides a bacterium that have an increased resistance to furfural and/or 5-HMF as compared to a reference bacterium and wherein said bacterium has increased ethanol production as compared to a reference bacterium in the presence of furfural and/or 5-HMF.

In one aspect, a bacterium of the invention have increased ethanol production as compared to a reference bacterium, in the decrease or absence of reductive removal of furfural as compared to a reference bacterium.

In another aspect, the bacterium of the invention has a decreased or eliminated furfural metabolism as compared to a reference bacterium.

The invention provides for a bacterium that has an increased resistance to furfural and further exhibit at least one of: 1) increased growth in the presence or absence of furfural as compared to a reference bacterium; 2) increased growth and increased ethanol production as compared to a reference bacterium; 3) increased growth and increased ethanol production, in the presence of furfural, as compared to a reference bacterium; 4) decreased furfural reductase activity as compared to a reference bacterium; and 5) increased growth in the presence of a hydrolysate as compared to a reference bacterium; and 6) increased ethanol production as compared to a reference bacterium.

The invention provides for a bacterium that has an increased resistance to 5-HMF and further exhibit at least one of: 1) increased growth in the presence or absence of 5-HMF as compared to a reference bacterium; 2) increased growth and increased ethanol production as compared to a reference bacterium; 3) increased growth and increased ethanol production, in the presence of 5-HMF, as compared to a reference bacterium; 4) decreased 5-HMF reductase activity as compared to a reference bacterium; and 5) increased growth in the presence of a hydrolysate as compared to a reference bacterium; and 6) increased ethanol production as compared to a reference bacterium.

The invention provides for a variety of hydrolysates including but not limited to hydrolysate derived from a biomass, a hemicellulosic biomass, a lignocellulosic biomass or a cellulosic biomass.

The invention also provides for a bacterium with increased resistance to furfural, wherein the bacterium is capable of producing ethanol as a primary fermentation product, wherein optionally, the primary fermentation product is produced under anaerobic or microaerobic conditions.

The invention also provides for a bacterium, wherein expression of the yqhD, yqhC and/or dkgA gene is/are decreased as compared to the expression in a reference bacterium and wherein the bacterium is capable of producing ethanol in the presence or absence of furfural.

Expression of the yqhD or yqhD and dkgA gene is/are decreased by methods know in the art including but not limited to altering a promoter that regulates the gene expression as compared to said reference bacterium, or by altering or deleting the yqhC gene as compared to a reference bacterium.

The invention also provides for a bacterium, wherein expression of the yqhC gene is decreased as compared to the expression in a reference bacterium and wherein the bacterium is capable of producing ethanol in the presence or absence of furfural.

In one aspect, the invention provides for an isolated bacterium, wherein yqhD, yqhC and/or dkgA gene expression is/are decreased or are not expressed, and wherein the bacterium produces ethanol in the presence or absence of furfural. A bacterium of the invention may also exhibit at least one of: 1) increased ethanol production and increased growth, in the presence of furfural, as compared to a reference bacterium; 2) increased ethanol production and increased growth, in the presence of furfural, as compared to a reference bacterium; 3) production of ethanol as a primary fermentation product, wherein optionally, the primary fermentation product is produced under anaerobic or microaerobic conditions; and 4) production of ethanol as a primary fermentation product, wherein optionally, said primary fermentation product is produced under anaerobic or microaerobic conditions In one aspect, the invention provides for an isolated bacterium, wherein yqhC gene expression is decreased or eliminated.

The invention also provides for a bacterium wherein the activity of YqhD or YqhD and DkgA protein is decreased or eliminated as compared to the activity in a reference bacterium, and wherein the bacterium is capable of producing ethanol in the presence of furfural.

The invention also provides for a bacterium wherein the activity of YqhC is decreased or eliminated as compared to the activity in a reference bacterium, and wherein the bacterium is capable of producing ethanol in the presence of furfural.

In another aspect, the invention provides for a bacterium wherein the expression of the yqhD or yqhD and dkgA gene is/are decreased as compared to the expression of the yqhD or yqhD and dkgA gene in a reference bacterium, and wherein the bacterium is capable of producing ethanol in the presence of furfural.

The invention also provides for an isolated bacterium wherein regulation of the yqhD or yqhD and dkgA gene is altered as compared to the regulation in a reference bacterium, and wherein the bacterium is capable of producing ethanol in the presence of furfural.

The invention also provides for an isolated bacterium wherein the yqhD, yqhC and/or dkgA gene is/are inactivated or knocked out as compared to a reference bacterium, and wherein the bacterium can produce ethanol in the presence or absence of furfural.

The invention also provides for an isolated bacterium wherein the yqhC gene is inactivated or knocked out as compared to a reference bacterium, and wherein the bacterium can produce ethanol in the presence or absence of furfural.

The invention also provides for an isolated bacterium wherein regulation of the yqhD or yqhD and dkgA gene(s) is/are altered as compared to a reference bacterium, and wherein the bacterium is capable of producing ethanol, wherein optionally the production of ethanol is in the presence of furfural.

The invention also provides for an isolated bacterium wherein regulation of the yqhC gene is altered as compared to a reference bacterium, and wherein the bacterium is capable of producing ethanol, wherein optionally the production of ethanol is in the presence of furfural.

In one embodiment, the regulation of the yqhD or yqhD and dkgA gene(s) is/are altered by placing the yqhD or yqhD and dkgA gene(s) under the control of a different promoter or under the control of an additional promoter as compared to the reference bacterium or by altering or deleting the yqhC gene.

In one embodiment, the regulation of the yqhD or yqhD and dkgA gene(s) is/are altered by placing the yqhD or yqhD and dkgA gene(s) under the control of a different regulatory protein or under the control of an additional regulatory protein as compared to the reference bacterium or by altering or deleting the yqhC gene. In one embodiment, the regulatory protein is a repressor. In an alternative embodiment, the regulatory protein is an inducer.

Expression is also decreased by the method of anti-sense inhibition or anti-sense transcription.

The bacteria of the invention are produced by a variety of methods.

An isolated bacterium having reduced expression of an NADPH-dependent furfural reductase activity wherein said bacterium is capable of producing ethanol in the presence of furfural, is prepared by a process comprising the steps of: growing a candidate mutant strain of the bacterium in the presence or absence of furfural; and selecting mutants that produce ethanol in the presence of furfural.

Alternatively, an isolated bacterium having reduced expression of an NADPH dependent furfural reductase activity wherein the bacterium is capable of producing ethanol in the presence or absence of furfural is prepared by: growing a candidate strain of the bacterium in the presence of increasing concentrations of furfural; and selecting a bacterium that produce ethanol in the presence of furfural.

The NADPH-dependent furfural reductase can be any NADPH-dependent furfural reductase including but not limited to YqhD or YqhD and DkgA.

An isolated bacterium wherein expression of the yqhD or yqhD and dkgA gene is decreased as compared to a reference bacterium, wherein the bacterium is capable of producing ethanol in the presence or absence of furfural is prepared by a process comprising the steps of: growing a candidate mutant strain of the bacterium in the presence of furfural; and selecting mutants that produce ethanol in the presence of furfural; or, alternatively, growing a candidate strain of the bacterium in the presence of increasing concentrations of furfural; and selecting a bacterium that produce ethanol in the presence of furfural.

The invention also provides for methods of producing a bacterium that include a step wherein expression of the yqhC gene is decreased or wherein the yqhC gene is altered or deleted.

An isolated bacterium having reduced expression of an NADPH-dependent furfural reductase activity wherein the bacterium is capable of producing ethanol in the presence or absence of furfural, is prepared by a process comprising the steps of: decreasing the expression of yqhD or yqhD and dkgA; growing a candidate strain of the bacterium in the presence of furfural; and selecting a bacterium that produce ethanol in the presence of furfural.

An isolated bacterium having reduced expression of the yqhD gene or reduced expression of the yqhD and dkgA genes, wherein said bacterium is capable of producing ethanol in the presence of furfural, prepared by a process comprising the steps of: decreasing the expression of the yqhD or yqhD and dkgA genes; growing a candidate strain of the bacterium in the presence of furfural; and selecting a bacterium that produce ethanol in the presence of furfural.

An isolated bacterium wherein the activity of YqhD or YqhD and DkgA protein is decreased or eliminated as compared to the activity in a reference bacterium, wherein said bacterium is capable of producing ethanol in the presence or absence of furfural, is prepared by a process comprising the steps of: growing a candidate mutant strain of the bacterium in the presence of furfural; and selecting mutants that produce ethanol in the presence of furfural; or growing a candidate strain of the bacterium in the presence of increasing concentrations of furfural; and selecting a bacterium that produce ethanol in the presence of furfural.

The expression of a gene is decreased by methods known in the art including but not limited to gene knock out or gene silencing.

An isolated bacterium wherein the yqhD or yqhD and dkgA gene(s) is/are inactivated or knocked out as compared to a reference bacterium, wherein said bacterium is capable of producing ethanol in the presence or absence of furfural, is prepared by a process comprising the steps of: growing a candidate mutant strain of the bacterium in the presence of furfural; and selecting mutants that produce ethanol in the presence of furfural; or growing a candidate strain of the bacterium in the presence of increasing concentrations of furfural; and selecting a bacterium that produce ethanol in the presence of furfural.

An isolated bacterium wherein regulation of the yqhD or yqhD and dkgA gene is altered as compared to a reference bacterium, wherein the bacterium is capable of producing ethanol in the presence or absence of furfural, is prepared by a process comprising the steps of: growing a candidate mutant strain of the bacterium in the presence of furfural; and selecting mutants that produce ethanol in the presence of furfural; or growing a candidate strain of the bacterium in the presence of increasing concentrations of furfural; and selecting a bacterium that produce ethanol in the presence of furfural.

According to the methods of the invention regulation is altered by a variety of methods known in the art, included but not limited to placing the yqhD or yqhD and dkgA gene under the control of a different promoter or under the control of an additional promoter as compared to the reference bacterium. According to the methods of the invention, regulation is altered by a variety of methods known in the art, including but not limited to placing the yqhD or yqhD and dkgA gene(s) under the control of a different regulatory protein or under the control of an additional regulatory protein as compared to the reference bacterium. In one embodiment, the regulatory protein is a repressor. In an alternative embodiment, the regulatory protein is an inducer. The invention also provides for regulation of the yqhD or yqhD and dkgA gene(s) by altering or deleting the yqhC gene as compared to a reference bacterium.

The invention also provides for methods of preparing the bacterium of the invention wherein the yqhD or yqhD and dkgA gene is silenced by use of any method known in the art, including but not limited to anti-sense transcription.

The bacterium of the invention are non-recombinant or recombinant.

In one embodiment, the bacterium is capable of producing ethanol as a primary fermentation product, wherein optionally the primary fermentation product is produced under anaerobic or microaerobic conditions.

The bacterium of the invention are selected from the group consisting of Gram-negative bacteria and Gram-positive bacteria, wherein the Gram-negative bacterium is selected from the group consisting of *Acinetobacter, Gluconobacter, Zymomonas, Escherichia, Geobacter, Shewanella, Salmonella, Enterobacter* and *Klebsiella* and the Gram-positive bacterium is selected from the group consisting of *Bacillus, Clostridium, Corynebacterium, Lactobacillus, Lactococcus, Oenococcus, Streptococcus* and *Eubacterium*.

In one aspect, the bacterium of the invention is *Escherichia coli*.

In another aspect, the bacterium of the invention is *Klebsiella oxytoca*.

In another aspect, the bacterium of the invention is *E. coli* strain EMFR9.

In another aspect, the bacterium of the invention is *E. coli* strain EMFR9 represented by a deposit with the Agricultural Research Culture Collection designated as deposit number NRRL B-50240.

In another aspect, the bacterium of the invention is *E. coli* strain LY180 represented by a deposit with the Agricultural Research Culture Collection designated as deposit number NRRL B-50239.

In another aspect, the bacterium of the invention is *E. coli* strain EMFR17 represented by a deposit with the Agricultural Research Culture Collection designated as deposit number NRRL B-50241.

In another aspect, the bacterium of the invention is *E. coli* strain EMFR26 represented by a deposit with the Agricultural Research Culture Collection designated as deposit number NRRL B-50242 or EMFR35 represented by a deposit with the Agricultural Research Culture Collection designated as deposit number NRRL B-50243.

III. Methods for Producing Ethanol

In another aspect, the invention provides a method for producing ethanol from an oligosaccharide source. The method comprises contacting the oligosaccharide with a non-recombinant bacterium or host cell of the invention as described above, to thereby produce ethanol from an oligosaccharide source. In a particular embodiment of the method, the oligosaccharide is selected from the group consisting of lignocelluloses, hemicellulose, cellulose, pectin and any combination thereof.

In another aspect, the invention provides a method for producing ethanol from a biomass, a hemicellulosic biomass, a lignocellulosic biomass, a cellulosic biomass or an oligosaccharide source comprising contacting the biomass, hemicellulosic biomass, lignocellulosic biomass, cellulosic biomass or oligosaccharide with the isolated bacterium of the invention, thereby producing ethanol from a biomass, hemicellulosic biomass, lignocellulosic biomass, cellulosic biomass or an oligosaccharide source.

In another aspect, the invention provides a method for producing ethanol from a biomass, a hemicellulosic biomass, a lignocellulosic biomass, a cellulosic biomass or an oligosaccharide source in the presence of furfural comprising contacting the biomass, hemicellulosic biomass, lignocellulosic biomass, cellulosic biomass or oligosaccharide with the isolated bacterium of the invention, thereby producing ethanol from a biomass, hemicellulosic biomass, lignocellulosic biomass, cellulosic biomass or an oligosaccharide source.

The invention also provides for ethanol produced by the methods of the invention.

The host cell of the invention is characterized by a low level of ethanol production under anaerobic conditions. Wild type *E. coli* produces ethanol and acetate at a ratio of 1:1 during anaerobic growth. During stationary phase of growth, wild type *E. coli* produces lactate as the main product, and the fraction of ethanol in the total fermentation products is about 20%. The products in all these fermentations comprise various acids, thus leading to the term, mixed acid fermentation.

Typically, fermentation conditions are selected that provide an optimal pH and temperature for promoting the best growth kinetics of the producer host cell strain and catalytic conditions for the enzymes produced by the culture (Doran et al., (1993) *Biotechnol. Progress.* 9:533-538). For example, for *Klebsiella*, e.g., the P2 strain, optimal conditions were determined to be between 35-37° C. and pH 5.0-pH 5.4. Under these conditions, even exogenously added fungal endoglucanases and exoglucanases are quite stable and continue to function for long periods of time. Other conditions are discussed in the Examples. Moreover, it will be appreciated by the skilled artisan, that only routine experimentation is needed, using techniques known in the art, for optimizing a given fermentation reaction of the invention. See, for example, U.S. Pat. Nos. 5,424,202 and 5,916,787, which are specifically incorporated herein by this reference.

In yet another aspect, the invention provides a kit comprising a non-recombinant bacterium or host cell of the invention as described above, and instructions for producing ethanol in accordance with the methods and processes described herein. In one embodiment, the kit comprises a sugar source.

The invention also provides a method of increasing the resistance or tolerance of a bacterium to furfural or 5-HMF by reducing the expression and/or activity of an NADPH-dependent oxidoreductase.

The invention also provides a method of identifying an NADPH-dependent oxidoreductase that increases the resistance or tolerance of a bacterium to furfural or 5-HMF by reducing the expression and/activity of an NADPH-dependent oxidoreductase.

The invention also relates to increasing the growth of a bacterium in the presence of furfural or 5-HMF by reducing the expression and/or activity of an NADPH-dependent oxidoreductase.

The invention also relates to increasing the production of ethanol by a bacterium in the presence of furfural or 5-HMF by reducing the expression and/or activity of an NADPH-dependent oxidoreductase.

According to the methods, the NADPH-dependent oxidoreductase has a Km that is less than or equal to the Km of YqhD or DkgA.

In one embodiment, the preferred substrate for the NADPH-dependent oxidoreductase is NADPH and not NADH.

In another embodiment, the substrate for the NADPH-dependent oxidoreductase is NADPH and not NADH.

The Km of YqhD is approximately 2-34 µM, for example 2, 3, 4, 5, 6, 7, 8, 9, 10, 15, 20, 25, 30, 31 or 32 µM. In one embodiment, the Km of YqhD is approximately 4-24. In another embodiment, the Km of YqhD is approximately 6-16 µM. In another embodiment the Km of YqhD is 8 µM.

The Km of DkgA is approximately 6-92 µM, for example 6, 7, 8, 9, 10, 15, 20, 25, 30, 35 40, 45, 50, 55, 60, 65, 70, 75, 80, 85, 90, 91 or 92 µM. In one embodiment, the Km of DkgA is approximately 12-70. In another embodiment, the Km of dkgA is approximately 18-50 μM. In another embodiment the Km of YqhD is 23 μM.

IV. Methods of Use

The invention provides for a bacterium with increased resistance to furfural and/or 5-HMF. The bacterium can be used for producing ethanol, and particularly for producing ethanol from an oligosaccharide source, in the presence or absence of furfural, by contacting the oligosaccharide with the bacterium of the invention, thereby producing ethanol from an oligosaccharide source The invention also provides for kits for producing ethanol from an oligosaccharide source, in the presence or absence of furfural, wherein the kit comprises instructions for use and, optionally, packaging means.

V. Exemplification

The invention is further illustrated by the following examples, which should not be construed as limiting.

Throughout the examples, the following materials and methods are used unless otherwise stated.

Materials and Methods

Strains, Media, and Growth Conditions

Strains and plasmids used in this study are listed in Table 1. Plasmid and strain constructions were made using Luria broth (Miller 1992 A short course in bacterial genetics. CSHL Press. Plainview, N.Y.). Antibiotics were included as appropriate. Temperature-conditional plasmids were grown at 30° C.; all others were grown at 37° C. Ethanologenic strains were maintained in AM1 mineral salts medium (Martinez et al. 2007 Biotechnol. Lett. 29:397-404) supplemented with 20 g liter$^{-1}$ xylose for solid medium and 50 g liter$^{-1}$ xylose or higher for liquid medium used in fermentation experiments. Strain *E. coli* strain LY168 (Jarboe et al. 2007. Adv. Biochem. Engin/Biotechnol. 108:237-261) is a derivative of KO11 and served as the starting point for this investigation. Note that *E. coli* W (ATCC 9637) is the parent for strain KO11, initially reported to be a derivative of *E. coli* B (Ohta et al. 1991. Appl. Environ. Microbiol. 57:893-900).

TABLE 1

Bacterial strains, plasmids, and primers

| Strain, plasmid, or primer | Relevant characteristics | Reference of source |
|---|---|---|
| STRAINS | | |
| LY168 | frdA:: (Zm frg celY$_{Ec}$FRT) ΔldhA:: FRT ΔadhE:: (Zm frg estZ$_{Pp}$ FRT) ΔackA:: FRT rrlE:: (pdc adhA adhB FRT) lacY:: FRT ΔmgsA:: FRT, | Jarboe et al 2007; Yomano et al. 2008 |
| LY180 | ΔfrdBC:: (Zm frg celY$_{Ec}$) ΔldhA:: (Zm frg casAB$_{Ko}$) adhE:: (Zm frg estZ$_{Pp}$ FRT) ΔackA:: FRT rrlE:: (pdc adhA adhB FRT) ΔmgsA:: FRT | This study |
| EMFR9 | LY180 improved for furfural tolerance | This study |
| EMFR9 ΔyqhD | EMFR9 ΔyqhD: kan | This study |
| EMFR9 ΔdkgA | EMFR9 ΔdkgA: cat sacB | This study |
| EMFR9 ΔyqhD ΔdkgA | EMFR9 ΔyqhD:: kan, ΔdkgA:: cat sacB | This study |
| BL21 (λDE3) | F$^-$ ompT gal dcm lon hsdS$_B$(r$_B^-$ m$_B^-$)λ(DE3 [lacI lacUV5-T7 gene 1 ind1 sam7 nin5]) | Promega (Madison, WI) |
| *E. coli* TOP10F' | F'{lacIq Tn10 (TetR)} mcrA Δ(mrr-hsdRMS-mcrBC) φ80lacZΔM15 ΔlacX74 recA1 araD139 Δ(ara-leu)7697 galU galK rpsL endA1 nupG | Invitrogen (Carlsbad, CA) |
| PLASMIDS[1] | | |
| PCR 2.1 TOPO | bla kan lacZ Ply P$_{lac}$ | Invitrogen (Carlsbad, CA) |
| pLOI4301 | yqhD gene in pCR 2.1 TOPO | This study |
| pLOI4302 | yjjN gene in pCR 2.1 TOPO | This study |
| pLOI4303 | dkgA gene in pCR 2.1 TOPO | This study |
| pLOI4304 | yqfA gene in pCR 2.1 TOPO | This study |
| pLOI4305 | yajO gene in pCR 2.1 TOPO | This study |
| pLOI4306 | ydhU gene in pCR 2.1 TOPO | This study |
| pLOI4307 | ydhV gene in pCR 2.1 TOPO | This study |
| pLOI4308 | ygcW gene in pCR 2.1 TOPO | This study |

TABLE 1-continued

Bacterial strains, plasmids, and primers

| Strain, plasmid, or primer | Relevant characteristics | Reference of source |
|---|---|---|
| pLOI4309 | nemA gene in pCR 2.1 TOPO | This study |
| pLOI4310 | yjgB gene in pCR 2.1 TOPO | This study |
| pLOI4311 | ydhS gene in pCR 2.1 TOPO | This study |
| pLOI4312 | ydhY gene in pCR 2.1 TOPO | This study |
| pLOI4313 | His-tagged yqhD in pET15b | This study |
| PLOI4314 | His-tagged dkgA in pET15b | This study |
| pET 15b | T7 promoter, bla, His-tag vector | Novagen (Madison, WI) |
| pKD4 | FRT kan FRT | Datsenko 2000 |
| PKD46 | $P_{ara}$ bla, red recombinase (γ, β, exo) | Datsenko 2000 |
| PRIMERS[2] | (5' to 3') | |
| yqhD cloning | For-ACATCAGGCAGATCGTTCTC (SEQ ID NO: 1)<br>Rev-CCACAGCTTAGTGGTGATGA (SEQ ID NO: 2) | This study |
| yjjN cloning | For-GGAGAGCCGAATCATGTCTA (SEQ ID NO: 3)<br>Rev-CCGGAACCTGTCTCAACCAA (SEQ ID NO: 4) | This study |
| dkgA cloning | For-GCCTGCTCCGGTGAGTTCAT (SEQ ID NO: 5)<br>Rev-CCGGCTCTGCATGATGATGT (SEQ ID NO: 6) | This study |
| yqfA cloning | For-GCTGGAGAGGTATACATGTG (SEQ ID NO: 7)<br>Rev-GCCGTATTCGCTCGAAGAGT (SEQ ID NO: 8) | This study |
| yajO cloning | For-CCGCAGCACATGCAACTTGA (SEQ ID NO: 9)<br>Rev-ATGGCGCTGCCGACCAATGA (SEQ ID NO: 10) | This study |
| ydhU cloning | For-CCGCATCTGTATCGCCGGTT (SEQ ID NO: 11)<br>Rev-GCCGATGCGAGCATGATTCGT (SEQ ID NO: 12) | This study |
| ydhV cloning | For-ATTATCGAGTGGAAAGATAT (SEQ ID NO: 13)<br>Rev-CGTAGTCTCCGTTCTGCTTA (SEQ ID NO: 14) | This study |
| ygcW cloning | For-ACCTTTCTTTTTTTTGCCT (SEQ ID NO: 15)<br>Rev-TTACGACCGCTGCCGGAATC (SEQ ID NO: 16) | This study |
| nemA cloning | For-TTATTGCGACGCCTGCCGTT (SEQ ID NO: 17)<br>Rev-GTTCAATCACCGCTTCTTCG (SEQ ID NO: 18) | This study |
| yjgB cloning | For-CCTGCCATGCTCTACACTTC (SEQ ID NO: 19)<br>Rev-CTGGTTAGATGGCGACTATG (SEQ ID NO: 20) | This study |

TABLE 1-continued

Bacterial strains, plasmids, and primers

| Strain, plasmid, or primer | Relevant characteristics | Reference of source |
|---|---|---|
| ydhS cloning | For-AACTTATCTGATAACACTAA (SEQ ID NO: 21)<br>Rev-CCAACAGCGGCGACAATGTA (SEQ ID NO: 22) | This study |
| ydhY cloning | For-TCAGGCTGCTGAATTGTCAG (SEQ ID NO: 23)<br>Rev-GGCACCAGATCCAGTTAATG (SEQ ID NO: 24) | This study |
| Deletion of yqhD | For-GTTCTCTGCCCTCATATTGGCCCAGCAAAGGGAGCAAGTAGTGTAGGCTGGAGCTGCTTC (SEQ ID NO: 25)<br>Rev-GACGAAATGCCCGAAAACGAAAGTTTGAGGCGTAAAAAGCCATATGAATATCCTCCTTA (SEQ ID NO: 26) | This study |
| Deletion of dkgA | Outward 1-ACGGTTGGATTAGCCATACG (SEQ ID NO: 27)<br>Outward 2-GACCAGTTCGGCGGCTAACA (SEQ ID NO: 28)<br>For-GCCTGCTCCGGTGAGTTCAT (SEQ ID NO: 29)<br>Rev-CCGGCTCTGCATGATGATGT (SEQ ID NO: 30) | This study |
| yqhD cloning into pET15b | For-TGACTCTCGAGATGAACAACTTTAATCTGCA (SEQ ID NO: 31)<br>Rev-AGTCAGGATCCTTAGCGGGCGGCTTCGTATA (SEQ ID NO: 32) | This study |
| dkgA cloning into pET15b | For-ATATGCCTCGAGATGGCTAATCCAACCGTTAT (SEQ ID NO: 33)<br>Rev-CCGATAGGATCCTTAGCCGCCGAACTGGTCAGG (SEQ ID NO: 34) | This study |
| Sequencing yqhD | yqhD_for1 CGGCGAGGTACTGGTGAC (SEQ ID NO: 35)<br>yqhD_rev1 CATGTTAGCCGCCGAACT (SEQ ID NO: 36)<br>yqhD_seq1 TCATGTTGGCTTCTGCCG (SEQ ID NO: 37)<br>yqhD_seq2 GCGCAATCGCTGGTTTAC (SEQ ID NO: 38)<br>yqhD_seq3 GTTCCGATGATGAGCGTATTG (SEQ ID NO: 39)<br>yqhD_seq4 AGGCGTTTTCGATCAGAAAG (SEQ ID NO: 40) | This study |
| Sequencing dkgA | dkgA_for1 CCAGCAACCGGTTCAGAAT (SEQ ID NO: 41)<br>dkgA_rev1 AACGCGTGAAAATAGCGACT (SEQ ID NO: 42)<br>dkgA_seq1 GCGGTAAAGAGATTAAAAGCGC (SEQ ID NO: 43)<br>dkgA_seq2 TATGGCTAATCCAACCGTTATTAAG (SEQ ID NO: 44)<br>dkgA_seq3 CCCGCCCGTTGTTACTCT (SEQ ID NO: 45) | This study |
| Sequencing of yqfA | per_for: CCATCCGCGACGAGTCTGAA (SEQ ID NO: 46)<br>per_rev: GGTGAAGCGGAACTGAACAA (SEQ ID NO: 47)<br>seq1: CCATCCGCGACGAGTCTGAA (SEQ ID NO: 48)<br>seq2: CGACGCTCTATCACGCCATT (SEQ ID NO: 49) | This study |

TABLE 1-continued

Bacterial strains, plasmids, and primers

| Strain, plasmid, or primer | Relevant characteristics | Reference of source |
|---|---|---|
| Sequencing of yjjN | per_for: TGCGCTGTTTAAGATCGCT (SEQ ID NO: 50) per_rev CATGATTGCCTTCTCGGG (SEQ ID NO: 51) seq1 ACTGAGATGATCTCAAGCGATTG (SEQ ID NO: 52) seq2 GGAAACAACGCGAGATACCT (SEQ ID NO: 53) seq3 CCACGCTGGCAGAAACCTA (SEQ ID NO: 54) | This study |

[1] The genes inserted into pCR 2.1 TOPO include a native ribosomal binding site and transcriptional terminator. Expression is from the plasmid promoter ($P_{lac}$).
[2] Orientation of genes cloned into pCR 2.1 TOPO was verified by PCR analysis Strains and plasmids used in this study have been previously described (Miller et al. 2009a Appl Environ Microbiol 75: 6132-6141; Miller et al. 2009b Appl Environ Microbiol 75: 4315-4323). These include LY180 (an ethanologenic derivative of E. coli), EMFR9 (furfural-tolerant derivative of LY180), LY180ΔyqhD, LY180ΔdkgA, LY180ΔyqhD ΔdkgA, pLOI4301 containing yqhD. Plasmids pLOI4303 containing dkgA (Miller et al. 2009b Appl Environ Microbiol 75: 4315-4323), and pLOI4316 containing pntAB (Miller et al. 2009a Appl Environ Microbiol 75: 6132-6141) were also used. Cultures were grown at 37° C. in AM1 minimal media (Martinez et al. 2007 Biotechnol Lett 29:397-404) containing 20 g l$^{-1}$ xylose (solid medium), 50 g l$^{-1}$ xylose (Bioscreen C growth analyzer and tube cultures), or 100 g l$^{-1}$ (pH-controlled fermentations).

Tolerance to 5-HMF was tested using 13×100 mm closed tubes containing 4 ml AM1 and 5-HMF as indicated. When appropriate, antibiotics were included for plasmid maintenance. Tubes were inoculated to an initial density of 0.05 OD$_{550 nm}$. Growth was measured after incubation (60 rpm) for 48 h using a Spectronic 20D+ spectrophotometer (Thermo, Waltham, Mass.). To examine the effects of pntAB on furan tolerance, a multiwall plate containing 400 µl of AM1 (and 5-HMF or furfural) per well was inoculated as above. OD$_{(420-580 nm\ bandwidth)}$ was measured for 72 h using a Bioscreen C growth analyzer (Oy Growth Curves, Helsinki, Finland).

For fermentation experiments, seed cultures of LY180 and EMFR9 were grown overnight in small fermentors (37° C., 200 rpm) containing 350 ml of AM1 medium. Broth was maintained at pH 6.5 by the automatic addition of 2 N KOH. Upon reaching mid-log phase, experimental fermenters were inoculated to an initial cell density of 0.1 OD$_{550 nm}$. (33 mg dry cell weight l$^{-1}$). Cell mass (OD$_{550 nm}$) and furan levels were monitored at 12-h intervals as described previously (Martinez et al. 2000b Biotechnol Prog 16: 637-641).

Furan reduction in vivo was measured using pH-controlled fermenters. Furans were added when the cultures reached approximately 1 OD$_{550 nm}$ using a 10% w/v stock solution. Cell mass and 5-HMF were measured after 0, 15, 30, and 60 minutes.

Construction of Strain LY180

Strain LY168 has been previously described for the fermentation of sugars in hemicellulose hydrolysates (Jarboe et al., 2007 Adv. Biochem. Engin/Biotechnol. 108:237-261). Several modifications were made to improve substrate range (restoration of lactose utilization, integration of an endoglucanase, and integration of cellobiose utilization) resulting in LY180. Linear DNA fragments used for integration are shown in FIG. 1 and have been deposited in GenBank. The FRT region in lacY was replaced with the native E. coli ATCC 9637 sequence by double homologous recombination using Fragment A containing lacZ lacY lacA cynX' (Datsenko et al. 2000 PNAS 97:6640-6645, Jantama et al. 2008 Biotech. Bioeng. 30:881-893). Integrated strains were selected directly for lactose fermentation. The frdBC region downstream from frdA::Zm frg celY$_{Ec}$ (Erwinia chrysanthemi) was deleted by double homologous recombination using a two step process (Jantama et al. 2008 Biotech. Bioeng. 30:881-893). Fragment B (frdB', a cat-sacB cassette, and frdC') was integrated first with selection for chloramphenicol resistance. The cat-sacB cassette was then replaced with Fragment C consisting of frdA', Zymomonas mobilis promoter fragment, E. chrysanthemi celY, and frdC' by selecting for resistance to sucrose. This replacement also deleted an FRT site. The Klebsiella oxytoca genes encoding cellobiose utilization (casAB) were inserted into ldhA by double homologous recombination also using a two step process (Jantama et al. 2008 Biotech. Bioeng. 30:881-893). Fragment D (ldhA', a cat-sacB cassette, casAB, and 'ldhA) was used to replace the FRT site in ldhA with selection for resistance to chloramphenicol. The cat-sacB cassette was then replaced with Fragment E consisting of ldhA', a promoter fragment from Z. mobilis, and K. oxytoca casA'. Integrated strains were isolated by selecting directly for cellobiose fermentation. All constructs were verified by analyses of phenotypes and PCR products.

Growth-Based Selection for a Furfural Resistant Strain

LY180 was inoculated into a 500-ml vessel (initial inoculum of 50 mg dcw liter$^{-1}$) containing 350 ml of AM1 supplemented with 100 g liter$^{-1}$ xylose and 0.5 g liter$^{-1}$ furfural (37° C., 150 rpm, pH 6.5). Cultures were serially diluted into new fermenters at 24-h intervals, or when cell mass exceeded 330 mg dcw liter$^{-1}$. Furfural was gradually increased to 1.3 g liter$^{-1}$ as growth permitted. After 54 serial transfers, a resistant strain was isolated and designated EMFR9.

Furfural Resistance and Metabolism During Fermentation

Furfural resistance was compared in small fermenters (37° C., 150 rpm, pH 6.5, 350-ml working volume) using AM1 medium (Martinez et al. 2007 Biotechnol. Lett. 29:397-404) containing 100 g liter$^{-1}$ xylose. Seed cultures were inoculated to approximately 33 mg dcw liter$^{-1}$. Samples were removed periodically to measure cell mass, ethanol, and furfural.

Furfural toxicity (MIC) was also examined using tube cultures (13×100 mm) containing 4 ml of AM1 broth with 50 g liter$^{-1}$ (wt/vol) filtered-sterilized sugar, furfural, and other supplements. Cultures were inoculated to an initial density of 17 mg dcw liter$^{-1}$. Cell mass was measured after incubation at 37° C. for 24 h and 48 h.

Comparison of Hydrolysate Toxicity

A hemicellulose hydrolysate of sugar cane bagasse was produced using dilute sulfuric acid at elevated temperature and pressure and supplied by Verenium Corporation (Boston, Mass.). This hydrolysate contained 82 g liter$^{-1}$ total sugar (primarily xylose), 1.4 g liter$^{-1}$ furfural, and other constituents. Hydrolysate was supplemented with the mineral components of AM1 medium, adjusted to pH 6.5 using 45% KOH, and diluted with complete AM1 (80 g liter$^{-1}$ xylose). Diluted samples of hydrolysate were distributed into 13 mm×100 mm culture tubes (4 mL each), inoculated to an initial cell density of 17 g dcw liter$^{-1}$, and incubated at 37° C. Cell mass (after centrifugation and resuspending in broth) and ethanol concentration were measured after 48 h.

Microarray Analysis

Cultures were grown in small fermenters to a density of 670 mg dcw liter$^{-1}$. Furfural (0.5 g liter$^{-1}$) was added and incubation continued for 15 min prior to harvesting. All samples were immediately cooled in an ethanol-dry ice bath, harvested by centrifugation, resuspended in Qiagen RNA Later (Valencia, Calif.) and stored at −80° C. until purification. RNA was purified using a Qiagen RNeasy Mini Kit and sent to NimbleGen (Madison, Wis.) for microarray comparisons. Data was analyzed with ArrayStar software (DNA Star, Madison, Wis.).

Cloning and Deletion of Oxidoreductases

Oxidoreductase genes for expression studies (ribosomal-binding sites, coding regions, and 200 bp terminator regions) were amplified from strain LY180 genomic DNA using a Bio-Rad iCycler (Hercules, Calif.), ligated into pCR 2.1-TOPO vector, and cloned into E. coli TOP10F' using an Invitrogen TOPO TA Cloning Kit (Carlsbad, Calif.). Plasmids were purified using a QiaPrep Spin Mini Prep Kit. Gene orientation was established by PCR.

A yqhD deletion was constructed in LY180 as described by Datsenko and Wanner (Datsenko, et al. 2000 PNAS. 97:6640-6645) using the plasmids pKD4 and pKD46. A dkgA deletion in LY180 was constructed as described by Jantama et al. (Jantama et al. 2008 Biotech. Bioeng. 30:881-893). A double mutant with deletions in both yqhD and dkgA was also constructed. Repeated attempts to delete the yqfA gene were not successful.

Purification and Kinetic Analysis of YqhD and DkgA

Both the yqhD and dkgA genes were cloned into a Novagen pET-15b vector and expressed as a His-tagged protein in E. coli BL21 (DE3). Cells were grown with IPTG to approximately 1.3 g dcw liter$^{-1}$, washed with 100 mM phosphate buffer, and lysed using MP Fast Prep-24 (MP Biomedical, Solon Ohio) and Lysing Matrix B. Crude extracts were passed through a 0.22 µm PVDF filter and further purified using a 1 mL HiTrap nickel column. Purified enzymes were dialyzed in 100 mM phosphate buffer using a Thermo Slide-A-Lyser and quantified using a Thermo BCA Protein Assay Kit. Purity of YqhD and DkgA were estimated to be greater than 90% by SDS-PAGE. A single band was observed for each in an SDS-PAGE gel. Estimated sizes of the purified proteins were in agreement with predicted values of 43 kD and 31 kD, respectively. Apparent Kcat and apparent Km values were determined for both purified enzymes using NADPH and furfural.

Whole-Cell Assays of Furfural Metabolism In Vivo During Fermentation

Whole-cell furfural metabolism was measured using fermenters in which cultures were grown to a density of 670 mg dcw liter$^{-1}$ (mid log phase). Furfural was added to an initial concentration of 0.5 g liter$^{-1}$. Samples were removed at zero time and after 15, 30, and 60 min of incubation for the measurement of furfural and cell mass. The specific rate of furfural metabolism was calculated using the average cell mass during each assay interval. Results are expressed as µmoles min$^{-1}$ mg dcw$^{-1}$.

In Vitro Assay of Furfural Reduction

Anaerobic tube cultures were grown in AM1 medium containing 50 g liter$^{-1}$ xylose and harvested in mid log phase (0.7-1.0 g dcw liter$^{-1}$). Cells were washed once with 20 mL 100 mM potassium phosphate buffer (pH 7.0), resuspended in phosphate buffer to approximately 6.5 g dcw liter$^{-1}$, chilled on ice, and lysed for 20 sec using an MP FastPrep-24 cell disruptor and Lysing Matrix B. Debris was removed by centrifugation (13,000×g; 10 min) and the supernatant used to measure furfural-dependent oxidation of NADH and NADPH. Assays contained 100 mM phosphate buffer (pH 7.0), 20 mM furfural, and 0.2 mM reductant (NADPH or NADH). Furfural-dependent activity (µmoles min$^{-1}$ mg protein$^{-1}$) was measured as the change in absorbance at 340 nm. Greater than 80% of activity was NADPH-dependent.

Analyses

Ethanol was measured using an Agilent 6890N gas chromatograph (Palo Alto, Calif.) equipped with flame ionization detectors and a 15-meter HP-PlotQ megabore column. Dry cell weight was estimated by measuring optical density at 550 nm using a Bausch & Lomb Spectronic 70 spectrophotometer. An OD$_{550\,nm}$ of 1.0 is equivalent to approximately 333.3 mg dcw liter$^{-1}$.

Furfural levels in AM1 medium were measured by absorbance at OD$_{284\,nm}$ and OD$_{320\,nm}$ (Martinez et al. 2000 Biotechnol Prog. 16:637-641). The accuracy of this method was confirmed by HPLC analysis. Furfural content of bagasse hemicellulose hydrolysate was measured using an Agilent LC1100 liquid chromatograph (refractive index monitor and UV detector) and an Aminex HPX-87P ion exclusion column (BioRad, Hercules, Calif.) with water as the mobile phase Generation and Sequencing of PCR Products Genomic DNAs were prepared from bacterial cultures grown in AM1 minimal medium using the Qiagen DNeasy Blood and Tissue kit. Regions of interest were PCR amplified with Qiagen Taq PCR master mix, and the resulting PCR products purified with the QIAquick PCR purification kit. After quantitation of the DNAs relative to bands in the 2-log DNA ladder (NEB), DNAs were submitted to the University of Florida Sanger sequencing core for analysis on ABI 3130 DNA sequencers. The resulting sequencing data were assembled and compared using Vector NTI software (Invitrogen).

Furfural Consumption Assay

Cultures grown to a cell density of 0.66 dcw/L in fleakers containing 350 mL AM1-10% xylose medium were sampled immediately before and 15, 30, and 60 minutes after addition of furfural to 0.5 g/L. The residual furfural concentration in the culture was determined after removal of bacterial cells by centrifugation. A spectrophotometric method was used, as described previously.

Measurement of Luciferase Reporter Activity in Bacterial Cells

Cultures of E. coli carrying appropriate reporter plasmids were grown in AM1-5% xylose to OD 0.2-0.4. After addition of furfural, cells were pelleted, resuspended in Qiagen Qproteome bacterial lysis buffer, and stored at −80° C. The lysates were thawed at 37° C. for 2 minutes, and transferred to a white 96-well plate. An equal volume (50 uL) of PerkinElmer BriteLite reagent was added to each well, and the luminescence measured in a Promega Glomax 96-well luminometer.

BioScreen C growth Curves

Resistance to furfural was assessed by growth in AM1-5% xylose medium containing defined concentrations of furfural using a BioScreen C growth curve machine. Cultures were grown in tubes in a shaking 37° C. water bath until the OD reached 0.4-0.6, diluted to OD=0.3, and then 50 uL inoculated into each well of a 100-well honeycomb plates containing 350 uL medium. Optical density was measured at 30 minute intervals over a 65 h period of incubation at 37° C., with 10 s shaking immediately before each read. 10 replicates were used for each combination of strain and furfural concentration.

Plasmid Constructions

Plasmid pLOI4900 was constructed by transferring the firefly luciferase gene into pBAD24 (Guzman et al. 1995 J. Bacteriol. 177: 4121-4130), and then replacing the araC gene and pBAD promoter regions with a 150-bp region upstream from the yqhD gene in LY180. This putative yqhD promoter region was PCR amplified using primers PCT6 and PCT7 (Table 2).

The yqhC gene was amplified from LY180 genomic DNA with primers PCT50 and PCT51, generating a PCR product containing the entire yqhC gene plus the 354-bp region upstream (native promoter). This fragment was cloned into pCC1 using the CopyControl PCR cloning kit (Epicentre) to produce pLOI4901. The pCC1 vector is a single-copy plasmid based on the E. coli F factor.

TABLE 2

Primers

| Primer name | Sequence |
| --- | --- |
| PCT6 | GCGTATGCATGCAATTTTGTAGCATTTCTCCAGC (SEQ ID NO: 55) |
| PCT7 | GCGGAATTCTACTTGCTCCCTTTGCTGGG (SEQ ID NO: 56) |
| PCT46 | ATGGTCCATATGAATATCCTCCTTAG (SEQ ID NO: 57) |
| PCT47 | GAGCTCGAGTAGGCTGGAGCTGCTTC (SEQ ID NO: 58) |
| PCT48 | GAGCTCGAGATGCGGCAATTTGATTGTGCGC (SEQ ID NO: 59) |
| PCT49 | GTTTCACGGCGTTCATCAGCG (SEQ ID NO: 60) |
| PCT50 | GTCTGGGCTGCTGGCTAAG (SEQ ID NO: 61) |
| PCT51 | TTTCATAAGCCGGGTTTGGCTC (SEQ ID NO: 62) |
| YqhC_ko_rev | GACGATTTTCCCCGTTCCCGGCTGCTGTACCGGG AACGTAT (SEQ ID NO: 63) |
| | CATATGAATATCCTCCTTA (SEQ ID NO: 64) |

Strain Constructions

The yqhC gene in LY180 was deleted by homologous recombination. First the kanamycin resistance (kan) cassette from pKD4 (Datsenko et al. 2000 Proc. Natl. Acad. Sci. USA 97:6640-6645) was flanked with regions that are to either side of the yqhC coding region. The sequence of the primer yqhC_ko_rev was specific for the region that matches the flank to the downstream side of yqhC. YqhC_ko_rev contains a 41-bp tail homologous to a sequence at the 3' end of the yqhC gene, and also matches 19 bp at the end of the kan cassette. At the upstream end of yqhC, the flanking region was generated by PCR amplification of a 418-bp fragment extending from the 5' end of yqhC into the yqhD gene, using primers PCT48 and PCT49. The kan cassette was amplified from pKD4 with primers PCT46 and PCT47, then joined to the PCT48 plus PCT49 PCR product (upstream yqhC flank) by ligation via XhoI sites in PCT 47 and in PCT48. Finally this kan-upstream flank construct was PCR amplified with the outermost primers yqhC_ko_rev and PCT49 to create a linear DNA consisting of the kan cassette in between a 41-bp downstream flank and a 418-bp upstream flank. Red recombinase-mediated recombination was used to replace the yqhC gene in LY180 with the kan cassette, thus generating LY180ΔyqhC. The resulting strain was verified by PCR analysis and sequencing.

Furfural Reduction In Vivo

Cultures were grown to a cell density of 0.66 g dcw liter$^{-1}$ in fleakers containing 350 mL AM1-100 g liter$^{-1}$ xylose medium and sampled immediately before and 15, 30, and 60 minutes after addition of furfural (to 0.5 g liter$^{-1}$) as previously described (Miller et al. 2009 Appl. Environ. Microbiol. 75:4315-4323). Residual furfural was measured in the culture broth after centrifugation using a spectrophotometric method (Martinez et al. 2000 Biotechnol. Prog. 16: 637-641).

Measurement of Luciferase Reporter Activity in Bacterial Cells

Cultures of E. coli carrying appropriate reporter plasmids were grown in AM1-50 g liter$^{-1}$ xylose to OD 0.4. After sampling the cultures, furfural was added, and incubation continued for 5, 15 or 30 min before sampling again. Untreated and furfural-treated cells were pelleted, resuspended in Qiagen Qproteome bacterial lysis buffer, and stored at −80° C. The lysates were thawed at 37° C. for 2 minutes, and transferred to a 96-well plate (white). An equal volume (50 µL) of PerkinElmer BriteLite reagent was added to each well. Luminescence was measured using a Promega Glomax 96-well luminometer.

Microarray Analysis

For each strain, 4 replicate 350 ml cultures were grown to OD=1.5 (0.66 g dcw liter$^{-1}$) and sampled. Furfural (0.5 g liter$^{-1}$) was added and samples were removed after 15 minutes of incubation. Culture samples were cooled in a dry ice/ethanol bath. Cells were pelleted at 4° C., resuspended in RNA Later (Qiagen), and stored at −80° C. Cell pellets from the 4 fermentors were pooled and used for RNA isolation (Qiagen RNeasy Mini Kit). RNA was treated with DNase, re-purified, and assessed for quality using an Agilent Bioanalyzer. RNA samples were submitted to Nimblegen for conversion to cDNA, labeling with Cy3, and hybridization to the E. coli K12 TI8333 microarray chip. This chip contains 385,000 60-mer probes derived from E. coli K12 strain MG1655, and has 5 replicates of each probe with an average of 18 probes per gene. Normalized expression data from Nimblegen was imported into ArrayStar (DNA Star) for analysis.

Accession Numbers for Nucleotide Sequences and Microarray Data

The DNA sequences for the yqhC-yqhD-dkgA regions of both LY180 and EMFR9 have been deposited with GenBank (accession numbers GQ478251 and GQ478252 respectively). Microarray data was deposited with the Gene Expression Omnibus (GEO) with accession number GSE17786.

Culture tubes (13×100 mm) containing AM1 and 0.1 mM IPTG were inoculated to 0.05 OD$_{550\,nm}$ and incubated at 37° C. These were harvested at a density of 1-2 OD$_{550\,nm}$. Cell pellets were washed once with 100 mM potassium phosphate buffer (pH 7.0), and resuspended in buffer at a density of 10 OD$_{550\,nm}$. Samples (1 ml) were added to 2-ml tubes containing Lysing Matrix B and disrupted (20 s) using a FastPrep-24 (MP Biomedicals, Solon, Ohio). Furan-dependent oxidation of NADPH was measured at 340 nm using a DU 800 spectrophotometer (Beckman Coulter, Fullerton, Calif.). Reactions (200 µl total volume; 37° C.) contained 50 µL crude extract, 0.2 mM NADPH, and 20 mM 5-HMF. Protein was measured using the BCA assay (Thermo Scientific, Rockford, Ill.).

Statistical Analysis

Data are presented as an average ±SD (n≥3). Statistical comparisons (2-tailed student-t test) were made using Graphpad Prism software (La Jolla, Calif.).

EXEMPLIFICATION

Example 1

Isolation and Initial Characterization of a Furfural-Resistant Mutant

A furfural-resistant derivative of LY180 was isolated after 54 serial transfers in pH-controlled fermenters containing AM1 mineral salts medium with 100 g liter$^{-1}$ xylose and increasing concentrations of furfural (0.5 liter$^{-1}$ initially to final concentration of 1.3 g liter$^{-1}$). Attempts to directly isolate mutants resistant to 1.0 g liter$^{-1}$ furfural in a single step (solid medium and broth) were not successful. Step-wise improvement in furfural tolerance was observed during serial transfers, consistent with multiple changes. The resulting strain, EMFR9, grew and fermented xylose in the presence of 1.0 g liter$^{-1}$ furfural at a rate equivalent to the parent LY180 in the absence of furfural (FIG. 2). Growth and ethanol production by EMFR9 also exceeded that of the parent LY180 in the absence of furfural.

Figure 2A:
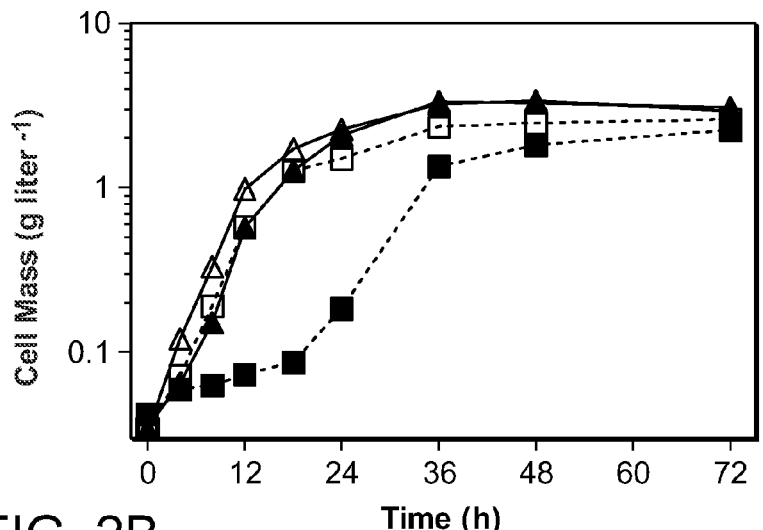
FIGS. 2A-F. Effect of furfural on the pH-controlled fermentation of 100 g liter$^{-1}$ xylose. Fermentation with 0.4 g liter$^{-1}$ furfural (A, B, and C). Fermentations with 1.0 g liter$^{-1}$ furfural (D, E, and F). For clarity, data for EMFR9 and LY180 are connected by solid and broken lines, respectively. Symbols for all: ■, LY180 with furfural; ▲, EMFR9 with furfural; □, LY180 without furfural; and △, EMFR9 without furfural.
Figure 2B:
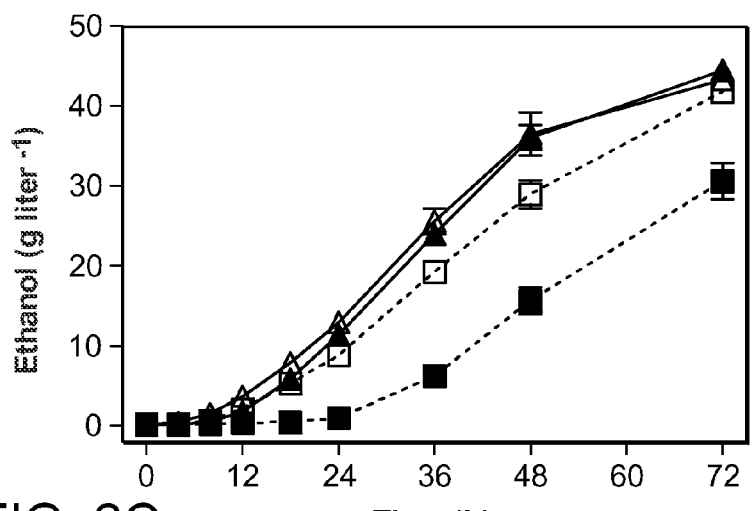
Figure 2C:
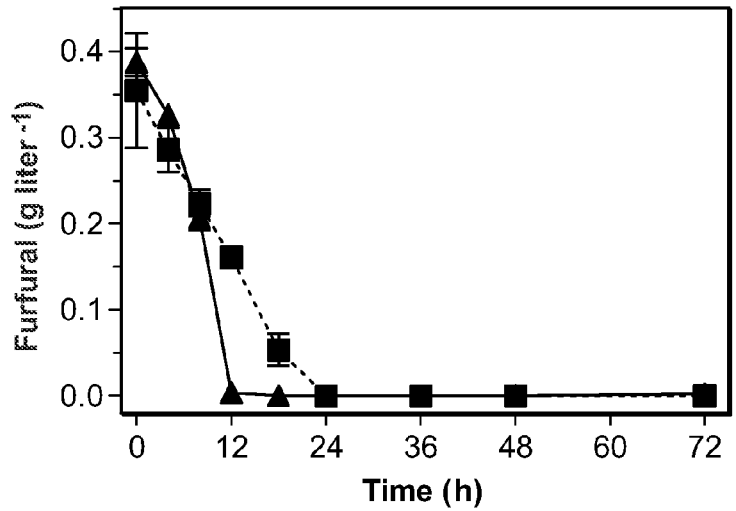
Figure 2D:
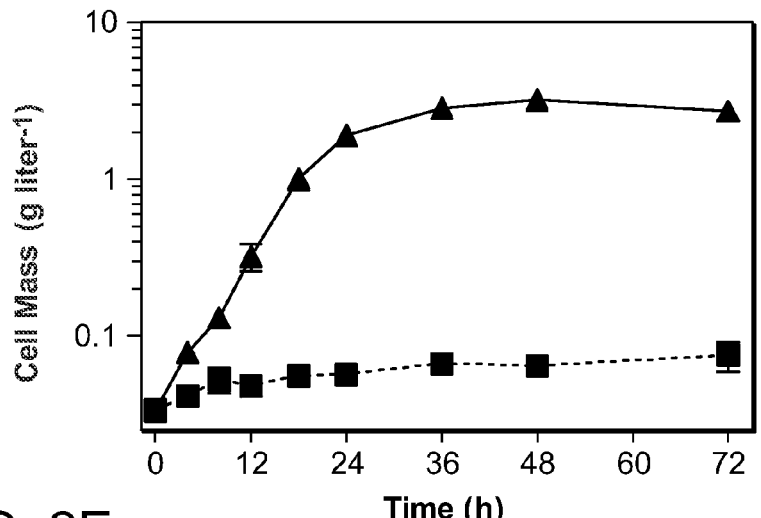
Figure 2E:
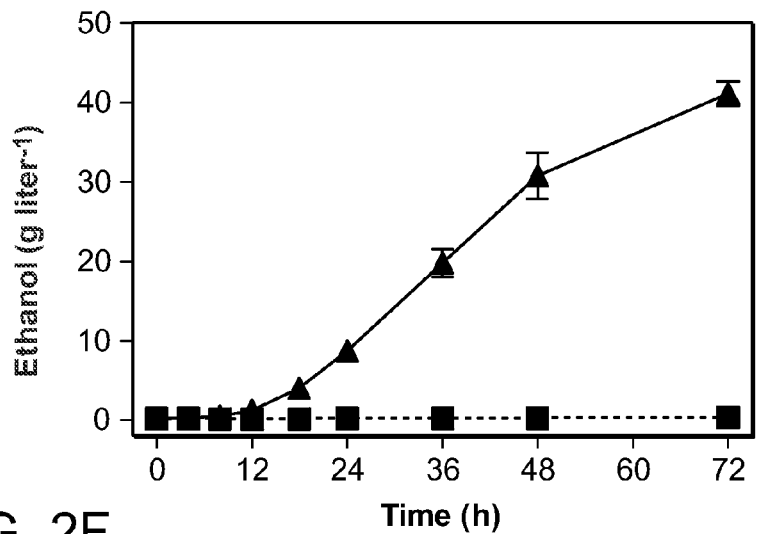
Figure 2F:
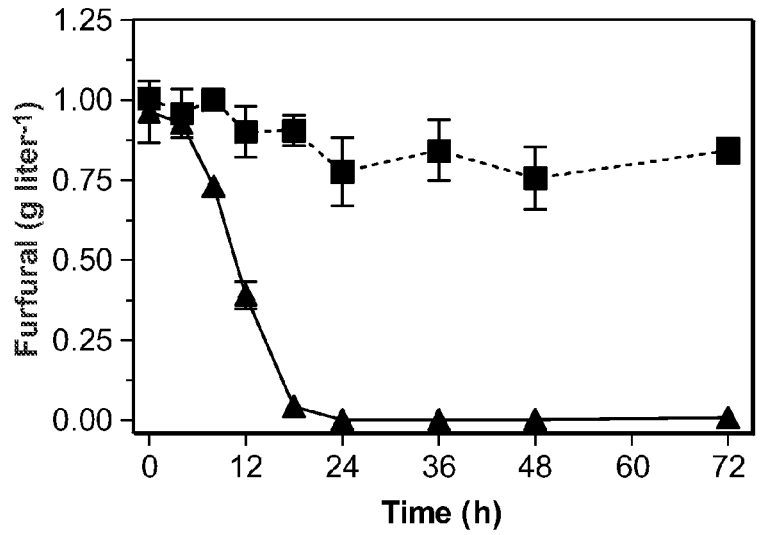

Addition of a low furfural concentration (0.4 g liter$^{-1}$) to the parent LY180 caused an initial lag in growth and ethanol production (FIGS. 2A and 2B). During this lag, furfural was chemically reduced to the less toxic furfuryl alcohol (Zaldivar et al. 1999. Biotechnol. Bioeng. 65: 24-33; Zaldivar et al. 2000 Biotechnol. Bioeng. 68:524-530) (FIG. 2C). Growth and fermentation increased by more than 3-fold immediately following the complete removal of furfural. Growth and ethanol production by LY180 were strongly inhibited by 1.0 liter$^{-1}$ furfural throughout the 72-h incubation (FIGS. 2D and 2E). During this time, approximately 20% of the furfural was reduced indicating that LY180 remained metabolically active (FIG. 2F). In contrast to LY180, EMFR9 was virtually unaffected by the presence of furfural (0.4 g liter$^{-1}$ or 1.0 g liter$^{-1}$) (FIG. 2). The volumetric rate of furfural reduction was higher for EMFR9 than LY180 at both furfural concentrations (FIGS. 2C and 2F), primarily due to the larger amount of cell mass (FIG. 2A). This was confirmed by further experiments in which the in vivo rate of NADPH-dependent furfural reduction by EMFR9 (per mg dcw) was found to be about half that of the parent LY180 (FIG. 3). In contrast to LY180, growth and fermentation of EMFR9 did not require prior reductive removal of furfural. With EMFR9, both 0.4 g liter$^{-1}$ and 1.0 g liter$^{-1}$ furfural were reduced to furfuryl alcohol concurrently with growth. Reduction by EMFR9 was complete after 12 h and 18 h, respectively (FIGS. 2C and 2F).

Example 2

Effect of Media Composition on Furfural Resistance (MIC)

Figure 4A:
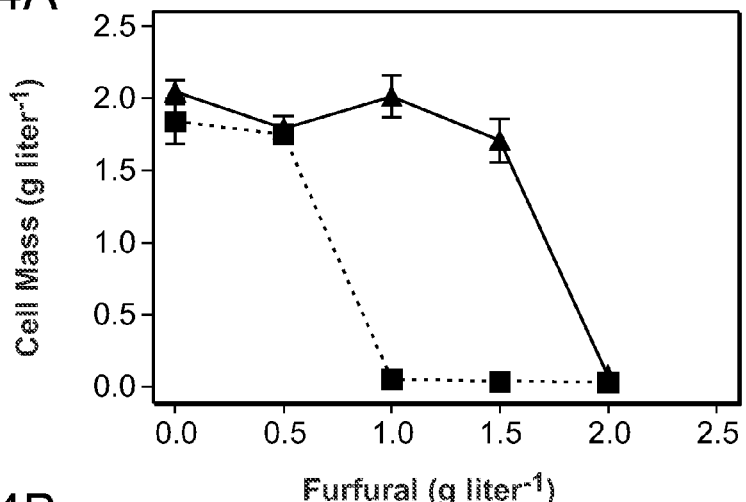
FIGS. 4A-C. Effect of media composition on furfural tolerance (MIC). A. AM1 medium containing xylose (50 g liter$^{-1}$); B. AM1 medium containing glucose; C. AM1 medium containing xylose and yeast extract (1.0 g liter$^{-1}$); Symbols for all: ■, LY180 (dashed line); and ▲, EMFR9 (solid line) after incubation for 48 hours.
Figure 4B:
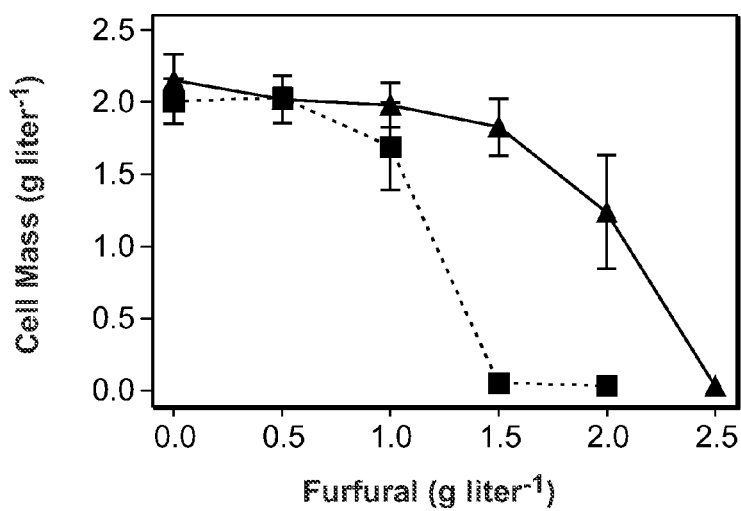
Figure 4C:
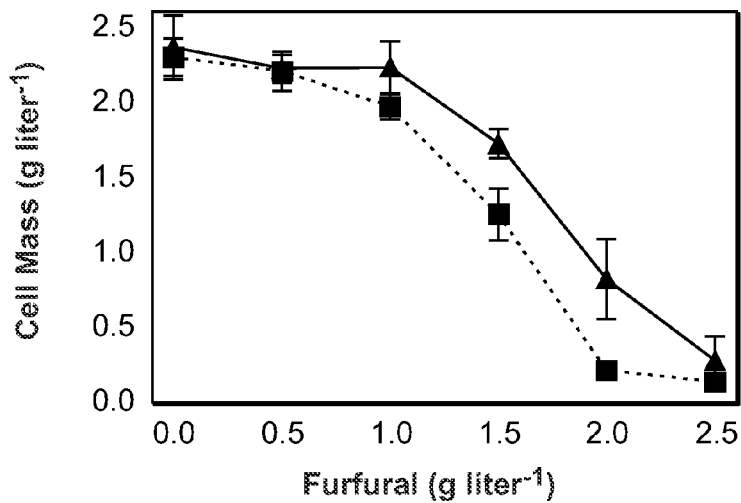
Figure 5A:
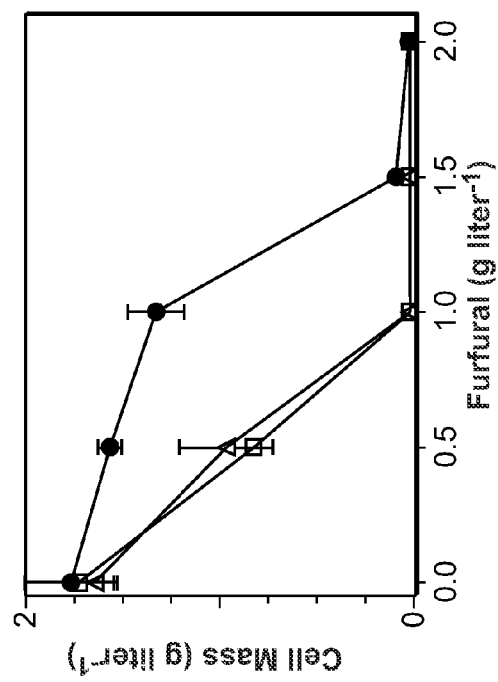
FIGS. 5A-D. Effect of gene expression in EMFR9 on furfural tolerance. A. Expression of dkgA; B. Expression of yqhD; C. Expression of yqfA; D. Expression of yjjN. Symbols for all: ●, pCR2.1 control without insert; □, uninduced expression; △, expression induced with 0.1 mM IPTG.
Figure 5B:
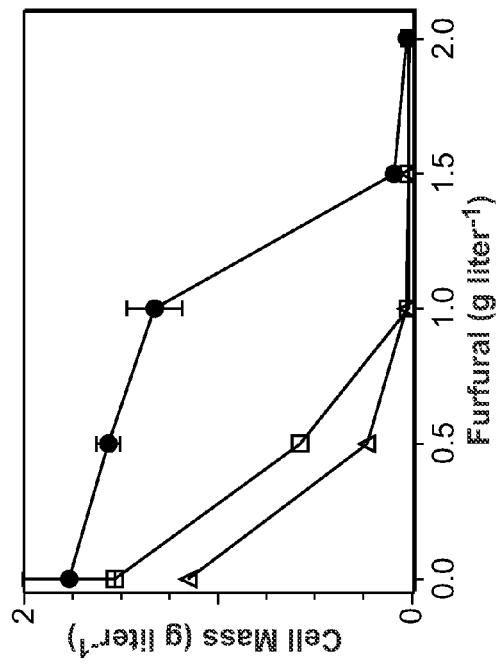
Figure 5C:
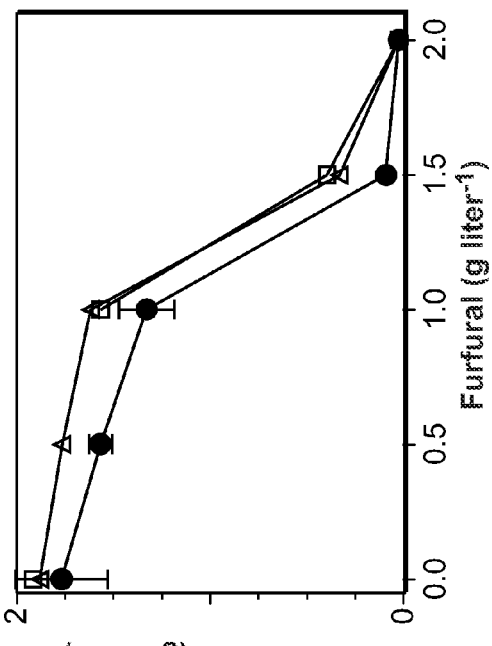
Figure 5D:
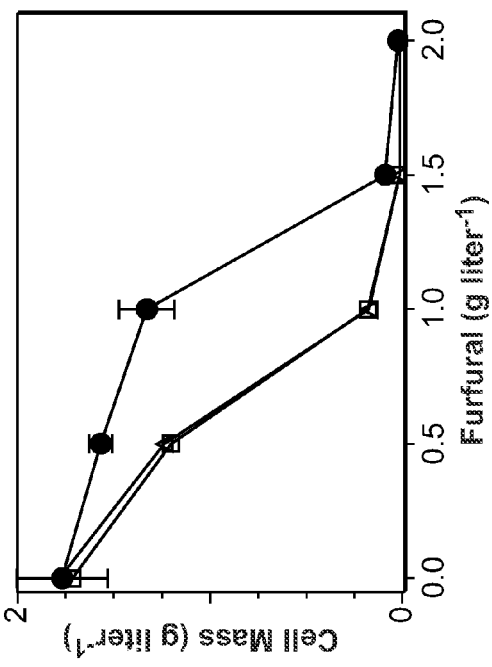

Unlike glucose, the production of NADPH is problematic during xylose fermentation (White, D. 2000. The Physiology and Biochemistry of Prokaryotes. 2$^{nd}$ edition. Oxford University Press. New York, N.Y.) and offers an approach to test the NADPH-competition hypothesis by measuring the MIC for furfural in different media. In mineral salts media with 50 g liter$^{-1}$ xylose (FIG. 4A), the minimal inhibitory concentration (MIC) of furfural was approximately 1.0 g liter$^{-1}$ for LY180 (parent) and 2.0 g liter$^{-1}$ for the mutant EMFR9. Replacement of xylose with glucose would be expected to increase the pool of NADPH. This change (FIG. 4B) increased the furfural MIC by 50% for LY180 (1.5 g liter$^{-1}$) and by 25% for EMFR9 (2.5 g liter$^{-1}$). Addition of a small amount of yeast extract (1.0 g liter$^{-1}$) to xylose-mineral salts medium would be expected to decrease biosynthetic demands for NADPH. This supplement (FIG. 4C) doubled the furfural MIC for the parent LY180 (2.0 g liter$^{-1}$) and increased the MIC for EMFR9 (2.5 g liter$^{-1}$) by 25%. With all media, EMFR9 was more resistant to furfural than the parent LY180. Both glucose (increased NADPH production) and yeast extract (decreased need for biosynthesis) increased furfural tolerance. However, this benefit was more pronounced for the parent, strain LY180, than for the mutant EMFR9, consistent with the lower level of furfural reductase activity in EMFR9.

The MIC for three other compounds known to be present in hemicellulose hydrolysates were also examined: 2-hydroxymethyl furfural (analogue, dehydration product of hexose sugars), furfuryl alcohol (reduced product of furfural), and syringaldehyde (degradation product of lignin). EMFR9 was slightly more tolerant to 2-hydroxymethyl furfural (MIC of 3.0 g liter$^{-1}$) than LY180 (MIC of 2.5 g liter$^{-1}$). Both strains were equally sensitive to syringaldehyde (MIC 2.0 g liter$^{-1}$) and furfuryl alcohol (15 g liter$^{-1}$) (data not shown). The absence of an increase in tolerance to other compounds in EMFR9 is consistent with a specific site or target for furfural toxicity.

Example 3

Comparison of Oxidoreductase Expression by mRNA Microarray Analysis

Previous studies have demonstrated that *E. coli* contains NADPH-dependent enzyme(s) capable of reducing furfural to a less toxic compound (furfuryl alcohol) but no gene was identified (Gutiérrez et al. 2006. J. Bacteriol. 121:154-164). The dependence of the parent LY180 on the complete reduction of furfural prior to growth and the loss of this dependence by EMFR9 further implicates oxidoreductases as being of primary importance for furfural sensitivity.

Microarray analysis of mRNA was used to identify candidate oxidoreductase genes for furfural reduction. Cultures of LY180 and EMFR9 were grown to mid-log phase in pH-controlled fermentations with 100 g liter$^{-1}$ (wt/vol) xylose. For this comparison, RNA was isolated 15 min after the addition of 0.5 g liter$^{-1}$ furfural. A total of 12 known and putative oxidoreductases were found that differed by approximately 2-fold or higher (Table 3).

TABLE 3

Oxidoreductases that were differentially expressed during growth in the presence of furfural (0.5 g l$^{-1}$)

| Gene | Transcripts that were approximately 2-fold or greater in EMFR9 relative to LY180 | | Effect of over expression of cloned genes on MIC for furfural Expression in LY180 |
|---|---|---|---|
| | Accession number | Fold increase | |
| yajO | b0419 | 1.9 | No increase |
| ydhU | b1670 | 1.8 | No increase |
| ydhV | b1673 | 2.0 | No increase |

TABLE 3-continued

Oxidoreductases that were differentially expressed during growth in the presence of furfural (0.5 g l$^{-1}$)

| ygcW | b2774 | 2.1 | No increase |
| nemA | b1650 | 4.5 | No increase |
| yjgB | b4269 | 2.0 | No increase |
| ydhS | b1668 | 1.9 | No increase |
| ydhY | b1674 | 1.9 | No increase |

Transcripts that were approximately 2-fold or more lower in EMFR9 relative to LY180

| Gene | Accession number | Fold decrease | Expression in EMFR9 |
|---|---|---|---|
| yqhD | b3011 | −48 | Reduced MIC |
| dkgA | b3012 | −12 | Reduced MIC |
| yjjN | b4358 | −4.4 | No effect on MIC |
| yqfA | b2899 | −2.5 | Reduced MIC |

Figure 3A:
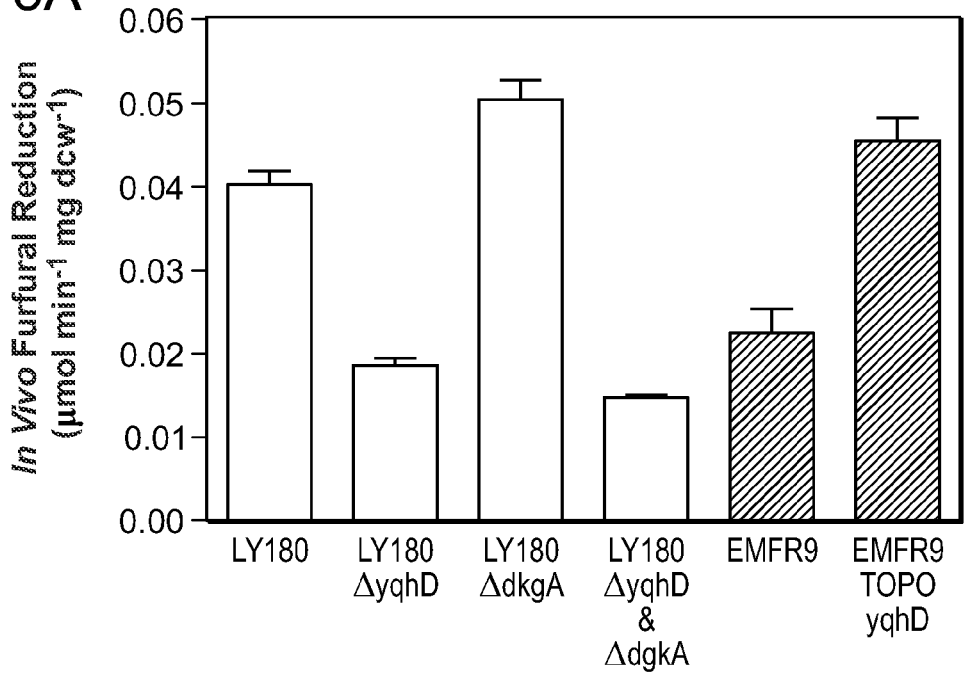
FIGS. 3A-B. Comparison of furfural-reducing activities. A. In vivo activity of whole cells during fermentation. LY180 and deleted derivatives are shown as open bars. The furfural-resistant mutant, EMFR9 and EMFR9 (pLOI4301) expressing yqhD are shown as shaded bars. B. Comparison of in vitro furfural-reducing activities in cell-free extracts of EMFR9 harboring plasmids expressing cloned genes (forward direction, induced with 0.1 mM IPTG).
Figure 3B:
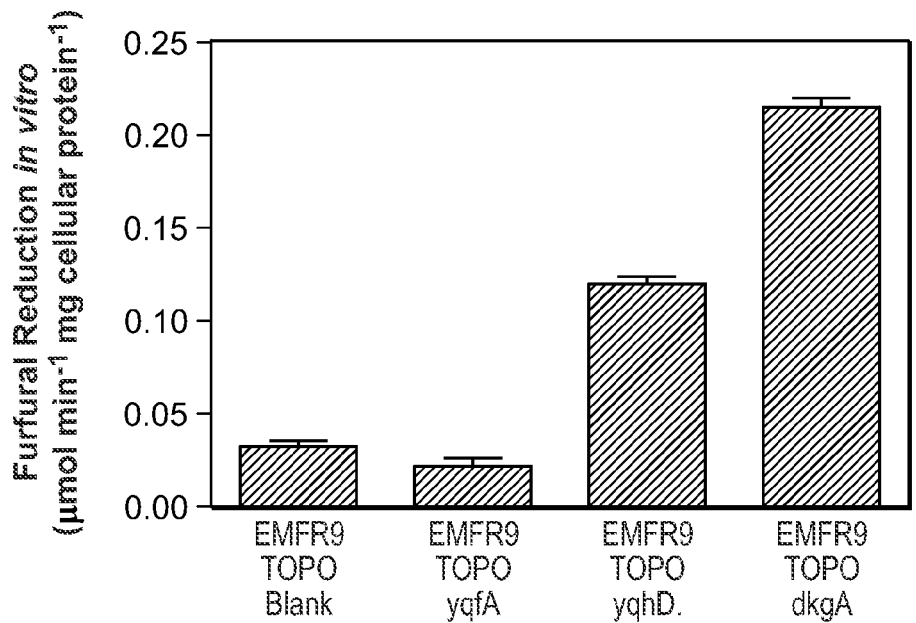

Four oxidoreductases were identified that were expressed at lower levels in EMFR9 (Table 3). Each of these four genes was cloned into plasmids and transformed into EMFR9. When expressed from plasmids, three of these genes (dkgA, yqhD, and yqfA) were found to decrease furfural tolerance (FIG. 5). Expression of yqhD and dkgA were most detrimental and both were shown to increase furfural reductase activity in EMFR9 (FIG. 3B). Expression of yqfA did not restore furfural reductase activity of EMFR9 and its effect on growth inhibition may be related to other functions. No detrimental effect on growth was observed for yjjN. Thus the decrease in expression of yqhD, dkgA, and yqfA in EMFR9 can be inferred to be beneficial for furfural tolerance. Silencing of yqhD and dkgA in EMFR9 would decrease the competition with biosynthesis for NADPH during furfural reduction.

The other eight genes were cloned from LY180 into pCR2.1-TOPO for expression. Eight of these oxidoreductases had increased expression in EMFR9 (1.8-fold to 4.5 fold) relative to the parent LY180. Plasmids containing each of these genes were transformed into LY180. However, none of these 8 caused an increase in furfural tolerance (data not shown).

Figure 6:
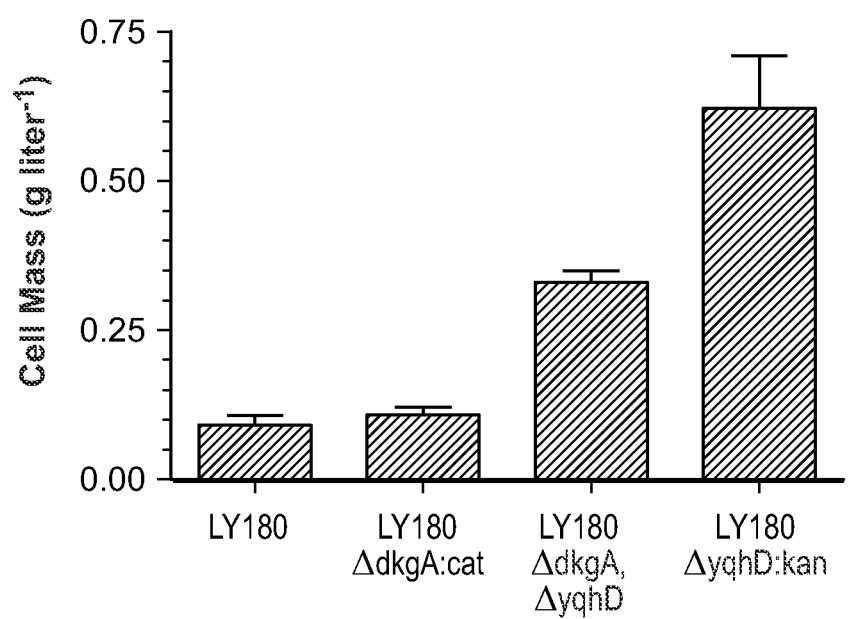
FIG. 6. Effect of gene deletions in LY180 on growth in the presence of 1.0 g liter$^{-1}$ furfural tolerance (48 h incubation).

To further examine the potential importance of yqhD, dkgA, and yqfA silencing, attempts were made to delete each of these genes from LY180. Although deletions of both yqhD and dkgA were readily recovered, similar methods were not successful with yqfA. In LY180, deletion of yqhD alone or in combination with dkgA caused an increase in furfural tolerance (FIG. 6) and a decrease in furfural reductase activity in vivo similar to that of EMFR9 (FIG. 3A). Since deletion of dkgA alone in LY180 did not lower the in vivo reductase activity or increase furfural tolerance, YqhD is presumed to be the more important activity for growth inhibition by low concentrations of furfural. The lowest furfural reductase activity was found after deletion of both genes.

Example 4

Characterization of YqhD and DkgA

The largest changes in gene expression among oxidoreductases were the silencing of yqhD and dkgA. Both YqhD and DkgA were expressed as his-tagged proteins in BL21 (λDE3) and purified to discernable homogeneity. Both enzymes catalyzed the NADPH-dependent reduction of furfural to furfuryl alcohol. The apparent Km values for furfural were relatively high for YqhD (9.0 mM) and DkgA (>130 mM). With such values, it is unlikely that furfural is the native substrate of either enzyme. Reasonably assuming that cells are permeable to furfural, the intracellular activities of YqhD and DkgA would be expected to vary over the range of furfural concentrations used for selection (5-14 mM; 0.5-1.3 g l$^{-1}$). The apparent Km values for NADPH were quite low for both YqhD (8 μM) and DkgA (23 μM). In the presence of furfural, the high affinity of both enzymes for NADPH would compete effectively with biosynthetic reactions for NADPH. Partitioning of NADPH among pathways would be determined by the Km for NADPH, steady state pool size of NADPH, and the relative abundance of competing oxidoreductase activities.

Example 5

Tolerance to Acid Hydrolysate of Hemicellulose

Hemicellulose hydrolysates contain a mixture of compounds that act in combination to inhibit microbial growth and fermentation (Martinez et al. 2001 Biotechnol. Prog. 17:287-293; Martinez et al. 2000 Biotechnol. Bioengin. 69(5): 526-536; Zaldivar et al. 1999 Biotechnol. Bioeng. 65: 24-33; Zaldivar et al. 1999 Biotechnol. Bioeng. 66: 203-210; Zaldivar et al. 2000. Biotechnol. Bioeng. 68:524-530). Growth and fermentation were examined in dilutions of a neutralized hydrolysate that contained 1.4 g liter$^{-1}$ furfural (FIG. 7). Although the MIC values for growth and ethanol production were similar (30% hydrolysate), EMFR9 grew to a 3-fold higher density and produced over 10-fold more ethanol in 20% hydrolysate than the parent LY180. Selection of EMFR9 for increased resistance to furfural was accompanied by an increase in resistance to hemicellulose hydrolysate, confirming the importance of furfural as a component of hydrolysate toxicity.

Example 6

Naturally Occurring Furfural Resistant Mutants

Figure 8:
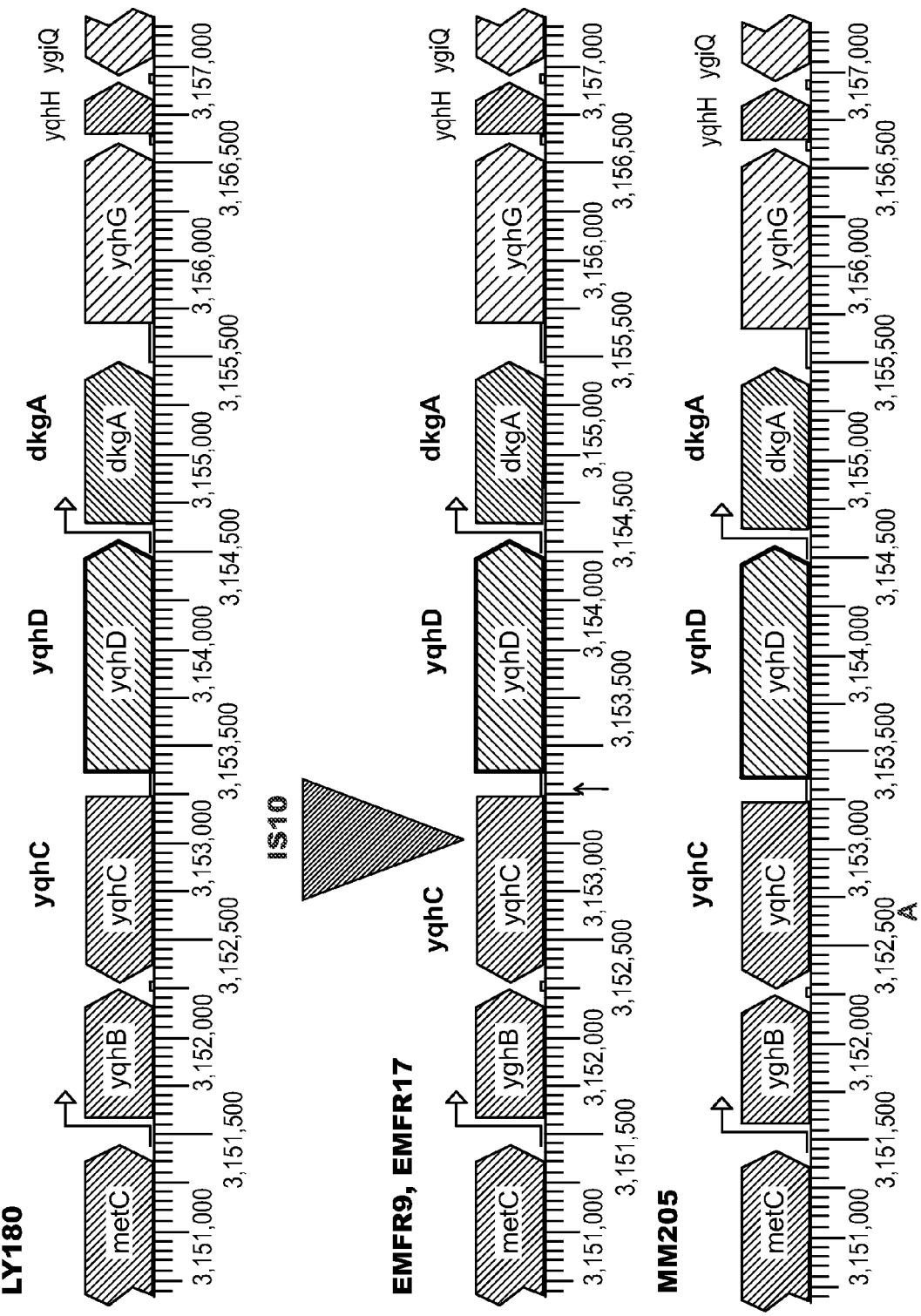
FIG. 8. Arrangement of the yqhC, yqhD and dkgA genes in the *E. coli* genome and locations of naturally occurring mutations in yqhC.
LY180 (furfural-sensitive, wild type). EMFR9 and EMFR17 (furfural-resistant). MM205 (furfural-resistant, selected as hydrolysate-resistant).
A, LY180 (furfural-sensitive, wild type). B, EMFR9 and EMFR17 (furfural-resistant). C, MM205 (furfural-resistant, selected as hydrolysate-resistant).

YqhC is adjacent in the *E. coli* genome to the yqhD and dkgA genes, which are transcribed in the opposite orientation to YqhC (FIG. 8).

Figure 9:
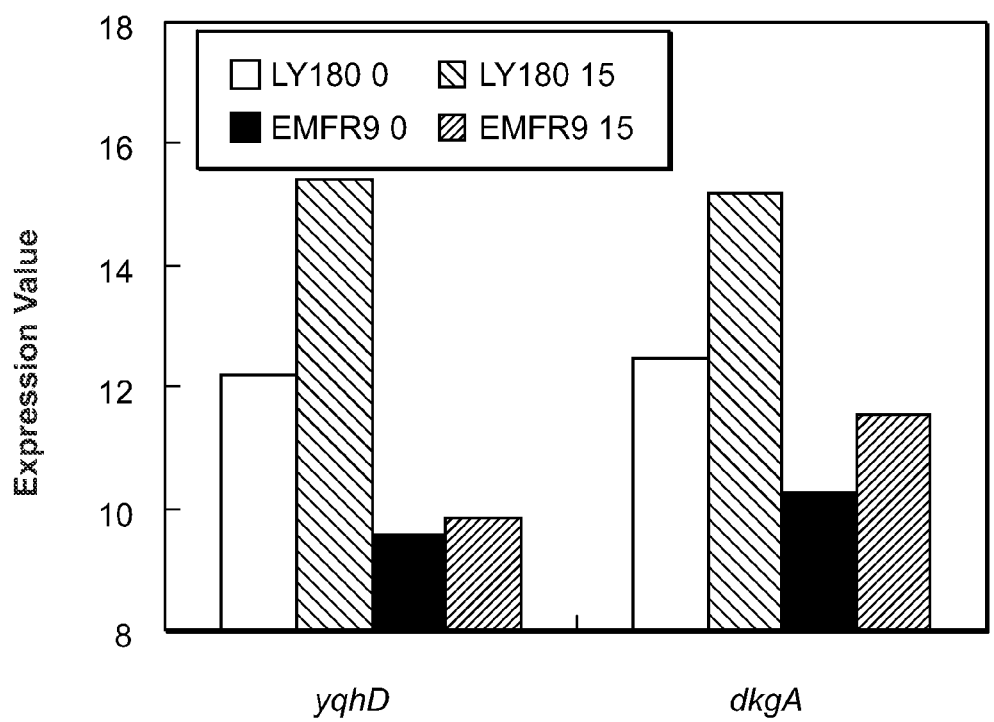
FIG. 9. Expression levels of yqhD and dkgA determined by microarray analysis of RNA. The expression level on the y-axis is on a log$_2$ scale. LY180 0 and EMFR9 0, expression levels prior to addition of furfural. LY180 15 and EMFR9 15, expression levels 15 minutes after addition of furfural.

Analysis of the yqhC region of the furfural resistant strain EMFR9 by a combination of PCR and DNA sequencing revealed that EMFR9 contains a natural insertion of the insertion sequence IS10 within the yqhC gene (FIG. 8). Inactivation of yqhC down regulates yqhD and dkgA, based on both microarray analysis of RNA (FIG. 9) and quantitative real-time reverse-transcription of RNA (not shown).

The ethanologenic strain MM205 was selected on the basis of growth in the presence of cellulose hydrolysate, and is resistant to furfural when compared with the parent strain LY180 (not shown). Sequence analysis of the yqhC gene and surrounding region of MM205 revealed the presence of a naturally occurring single A insertion in the yqhC gene, resulting in a frameshift such that instead of the wild type 199 amino acid yqhC protein, the predicted mutant protein is 215 amino acids. The residues from positions 1 to 188 are normal in the MM205 yqhC protein, but the next 27 amino acids result from the frameshift and are dissimilar to the wild type residues at the C-terminus of the protein.

Example 7

Deletion of the yqhC Gene Results in Increased Resistance to Furfural

A deletion of the entire yqhC gene was engineered into LY180. In this construct the yqhC open reading frame was replaced with a selectable kanamycin resistance cassette. The direction of kan-res transcription is in the same direction of the original yqhC gene, away from the neighboring yqhD and dkgA genes.

Comparison of growth of LY180 and LY180ΔyqhC at different furfural concentrations in the BioScreen C growth curve machine revealed that LY180ΔyqhC was substantially more furfural resistant than the parent LY180 (FIG. 10AB). Reintroduction of a plasmid-borne copy of the wild type yqhC gene under control of its natural promoter into LY180ΔyqhC restored furfural sensitivity to levels similar to the parent LY180 (FIG. 10C). Introduction of an empty vector pCC1 into LY180ΔyqhC had no effect on furfural resistance (FIG. 10D). These results are consistent with the absence of the yqhC protein conferring increased resistance to furfural.

Example 8

The yqhC Deletion Mutant has a Decreased Rate of Furfural Reduction

The naturally occurring furfural resistant mutant EMFR9 has decreased expression of both yqhD and dkgA. Reduced levels of these oxidoreductases diminishes depletion of the NADPH pool when furfural is present. EMFR9, as previously stated, has an IS10 insertion sequence present in the yqhC coding sequence, in addition to other characterized and uncharacterized mutations.

Figure 11:
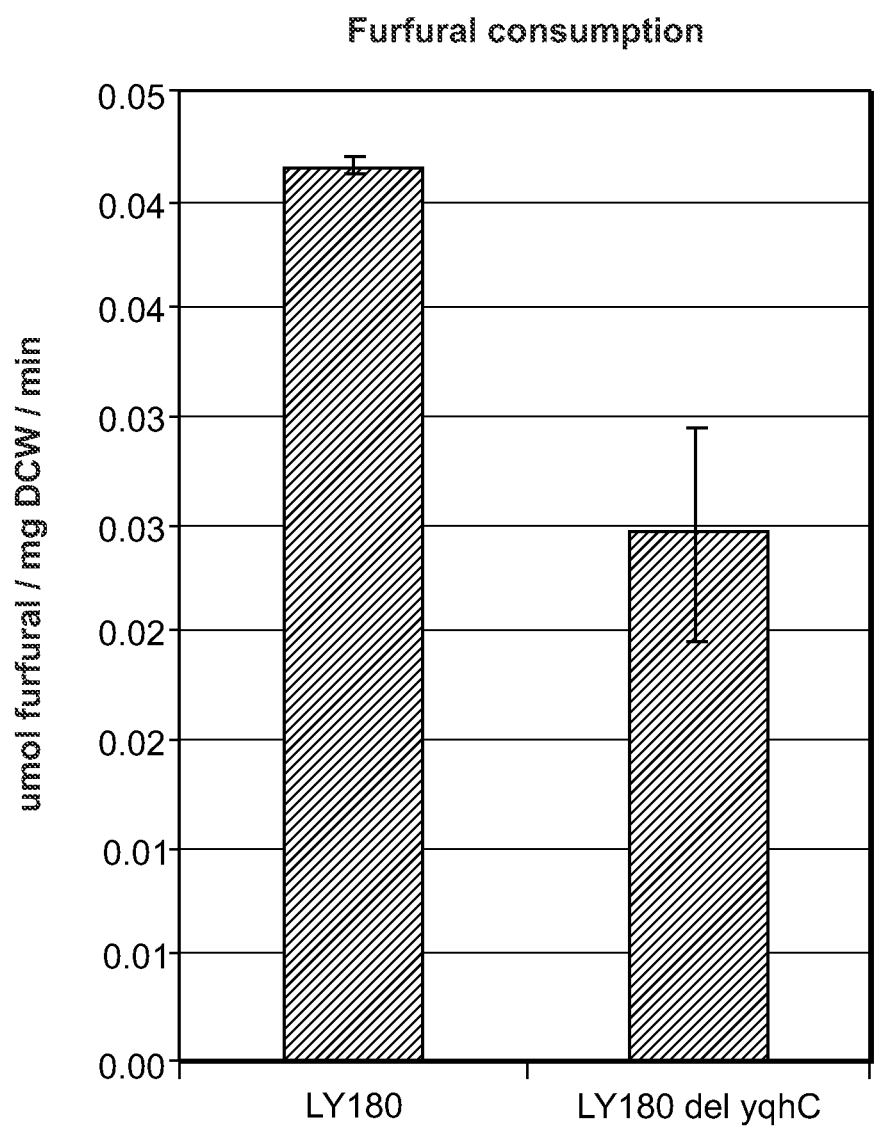
FIG. 11. Rates of furfural consumption by LY180 and LY180ΔyqhC.

The rates of furfural reduction by LY180 and LY180ΔyqhC were compared directly by growing the two strains in AM1-10% xylose medium in fleakers to a defined OD, adding furfural to 0.5 g/L, taking samples at intervals, and measuring the remaining furfural concentration spectrophotometrically. The results (derived from 4 identical fleakers per strain) showed that the rate of furfural reduction is reduced in LY180ΔyqhC compared with LY180 (FIG. 11), and are consistent with deletion of yqhC resulting in down-regulation of oxidoreductases that normally reduce furfural to furfuryl alcohol, with concomitant oxidation of NADPH.

Example 9

Figure 12:
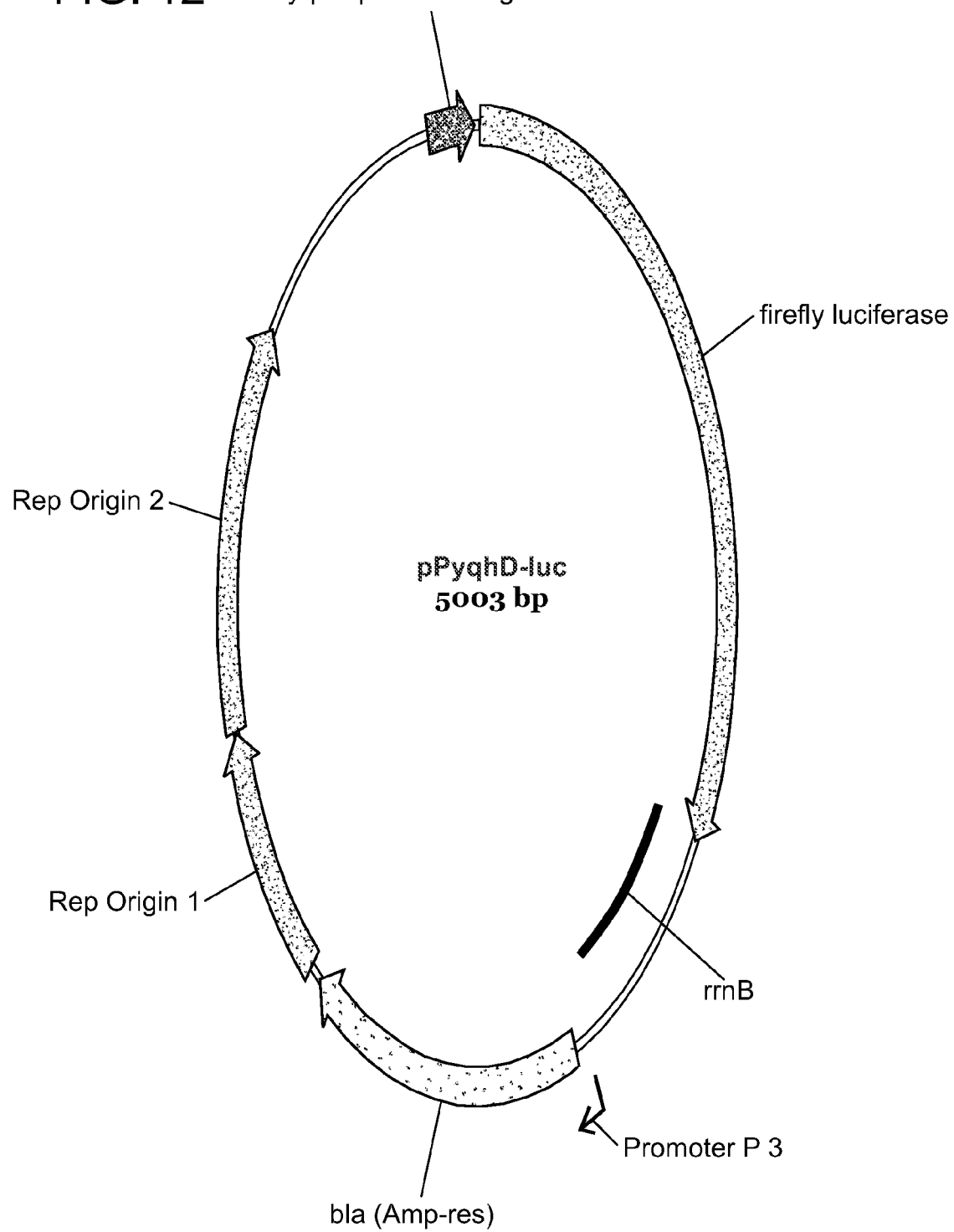
FIG. 12. Structure of plasmid pPyqhD-luc, with the promoter of the yqhD gene cloned upstream from the firefly luciferase reporter gene.
Figure 13:
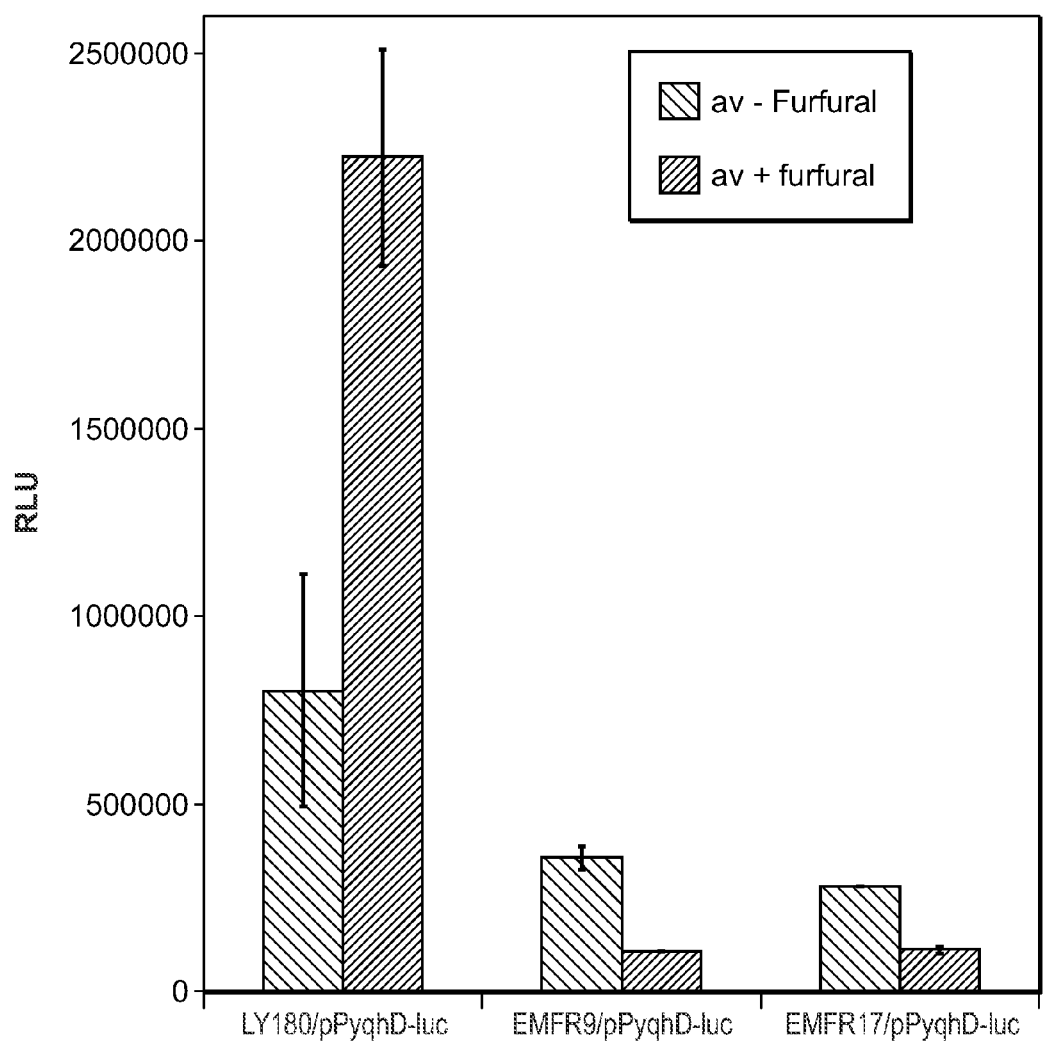
FIG. 13. Expression of luciferase before and after addition of furfural. The luciferase reporter plasmid pPyqhD-luc was transferred into LY180, EMFR9, and EMFR17. Luciferase levels were determined immediately before and 15 minutes after furfural addition. The values on the y-axis are relative luminescence units (RLU).

Deletion of yqhC Interferes with Induction of the yqhD Promoter by Exposure to Furfural The plasmid pPyqhD-luc (FIG. 12) was constructed with the firefly luciferase reporter downstream from the yqhD promoter in order to assess the effect of furfural on transcription from the yqhD promoter. Measurement of luciferase activity in LY180 carrying pPyqhD-luc showed that activity was increased at 15 minutes after the addition of furfural (FIG. 13). However, when the reporter plasmid pPyqhD-luc was transferred into EMFR9 and a further furfural resistant derivative EMFR17, luciferase expression was not increased by furfural addition (FIG. 13), suggesting that these strains have evolved to suppress activation from the yqhD promoter that normally occurs when furfural is present.

Figure 14:
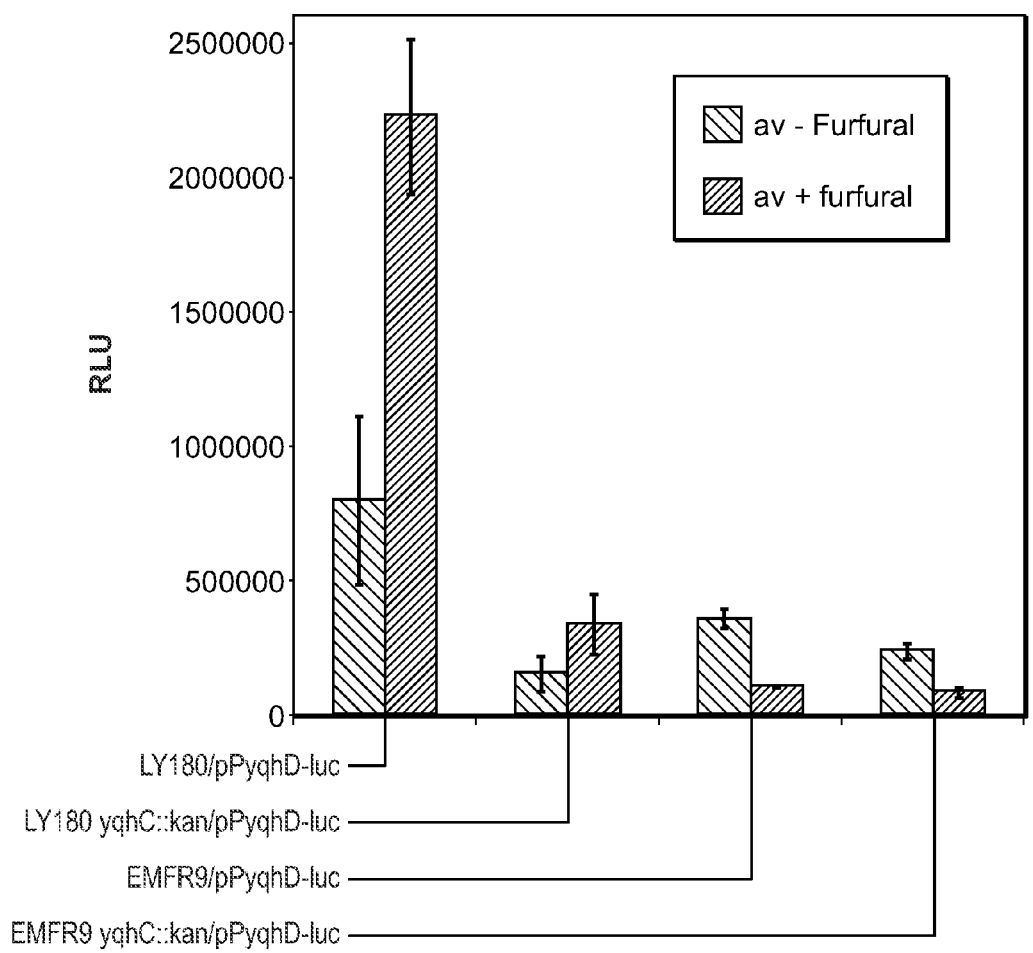
FIG. 14. Expression of luciferase from the yqhD promoter in LY180 and LY180ΔyqhC.

The effect of yqhC deletion on yqhD promoter activity was tested by transferring pPyqhD-luc into LY180ΔyqhC. The results obtained (FIG. 14) show that induction of luciferase from the pPyqhD-luc reporter plasmid was greatly reduced by deletion of yqhC.

Figure 15:
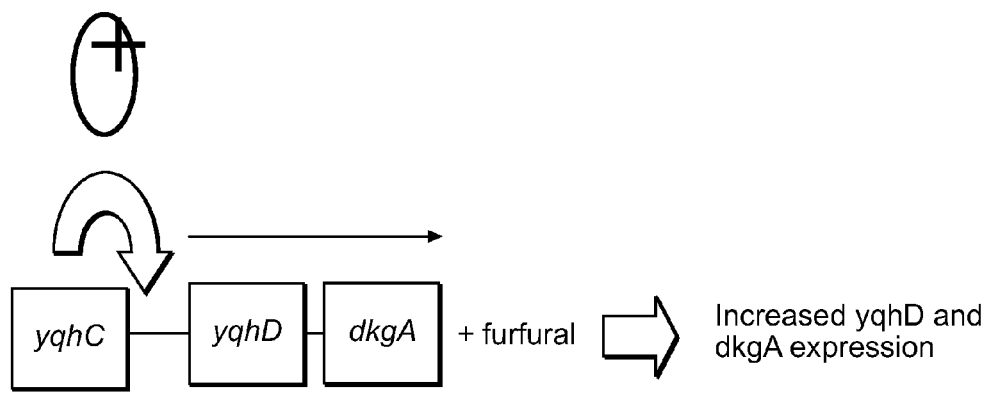
FIG. 15. Model showing proposed regulatory role of YqhC in transcription from the promoter for YqhD.

The available data demonstrate that yqhC regulates yqhD transcription in a positive manner upon addition of substrates for yqhD, including furfural (FIG. 15). Although the dkgA gene may have its own promoter (Gama-Castro et al., 2008 Nucleic Acids Res 36:D120-D124), according to the data presented herein, yqhD and dkgA are coordinately regulated.

Example 10

The Furfural Tolerant Strain EMFR9 Contains an IS10 Insertion in yqhC

Figure 20A:
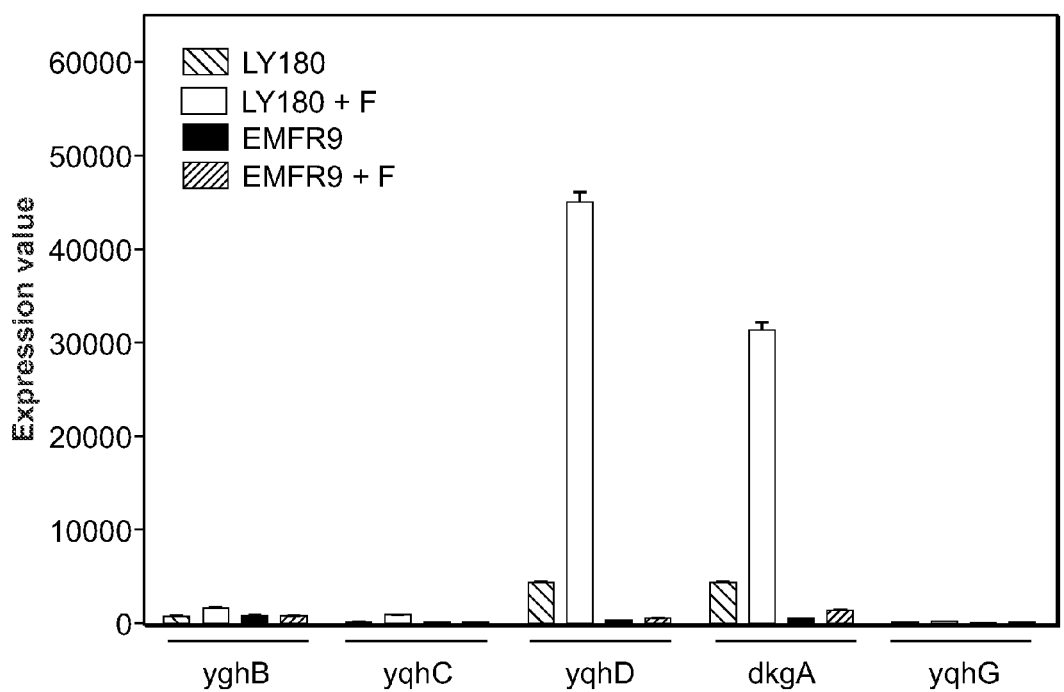
FIGS. 20A-B. Expression of transcripts in the yqhC-yqhD-dkgA region from LY180, EMFR9 and LY180ΔyqhC after addition of furfural. Transcript levels were determined by expression hybridization of total RNA against *E. coli* K12 microarrays. Cells were harvested either immediately before furfural addition, or 15 min after addition of 0.5 g liter$^{-1}$ furfural. The normalized expression values for selected genes are shown, with SEM error bars calculated from the 5 replicates of each probe present on the chip. (A). Expression levels for genes yqhC, yqhD, and dkgA with the flanking genes yghB and yqhG for strains LY180 and EMFR9 either untreated or treated for 15 min with 0.5 g liter$^{-1}$ furfural. (B). Expression levels for yqhC, yqhD, and dkgA plus flanking genes for strains LY180 and LY180ΔyqhC before and after treatment with furfural.

Silencing of two NADPH-dependent oxidoreductases (yqhD and dkgA) in a furfural-resistant mutant (EMFR9) of E. coli LY180 was previously shown to confer increased furfural tolerance (Miller et al. 2009 Appl. Environ Microbiol 75:4315-4323). No mutations were found in the coding regions of these genes or in the regions immediately upstream and downstream. A third adjacent gene, yqhC, (FIG. 19) was also silenced in EMFR9. In microarray analysis, all three genes were strongly up-regulated (>6-fold) by the addition of furfural in the parent LY180 (FIG. 20A).

Sequencing was extended to the upstream (yqhC) and downstream (yqhG) genes. PCR amplification of the yqhC gene gave an unexpectedly large PCR product containing a 1.3 kb IS10, flanked by copies of a nine-base sequence TGC-CAGGCT derived from yqhC. No mutations were found in the downstream yqhG region. The E. coli yqhC gene is transcribed opposite to the direction of yqhD (FIG. 19) and encodes a predicted transcriptional regulator belonging to the AraC/XylS family of DNA-binding proteins (Gallegos et al. 1997 Microbiol Mol. Biol. Rev. 61: 393-410). Many of these are transcriptional activators, although some act as both activator and repressor.

Example 11

Deletion of yqhC in LY180 Increased Furfural Tolerance

Figure 21A:
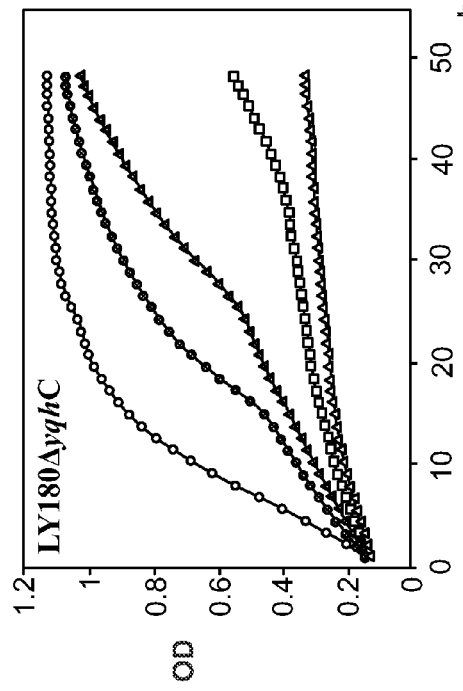
FIGS. 21A-D. The effect of yqhC deletion on growth in the presence of furfural. Strains were grown in AM1 medium with 50 g liter$^{-1}$ xylose, and containing 0, 0.5, 1, 1.5, or 2 g liter$^{-1}$ furfural. The optical density was monitored at 30 minute intervals over a 48 h period. The strains tested were LY180 (A), LY180ΔyqhC (B), LY180ΔyqhC containing the single copy plasmid pLOI4901 carrying yqhC$^+$ (C), and LY180ΔyqhC containing the empty vector pCC1 (D).
Figure 21B:
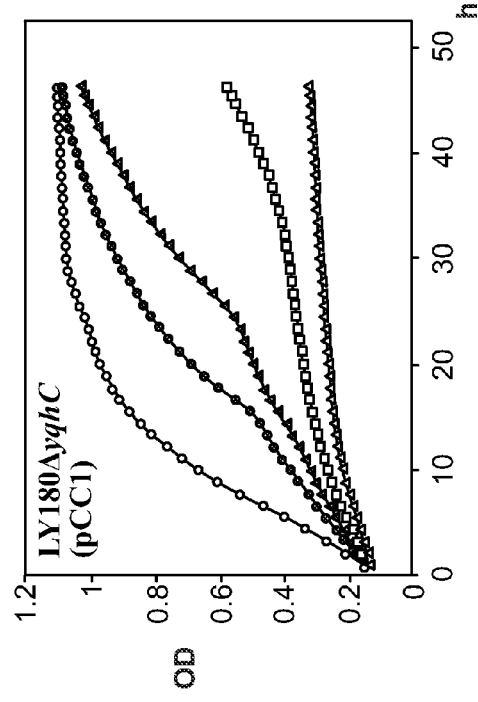
Figure 21C:
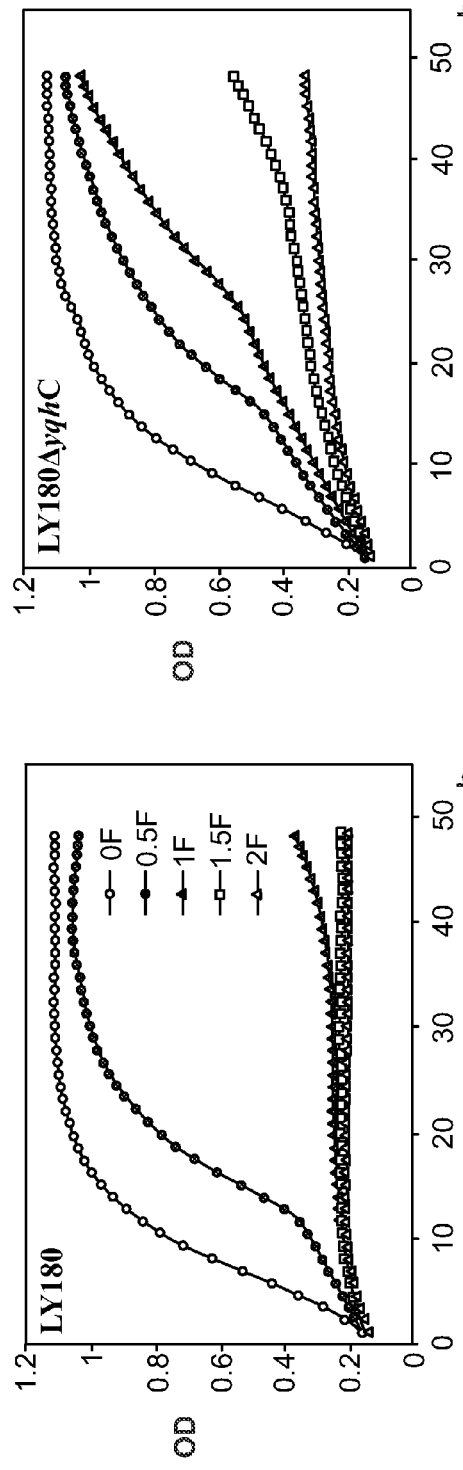
Figure 21D:
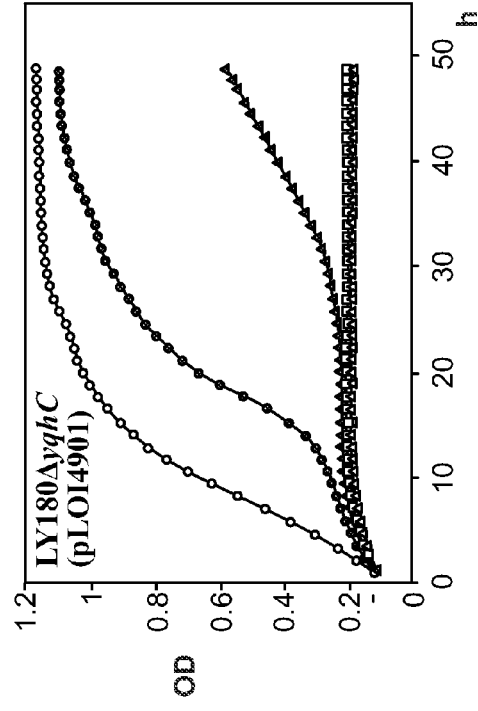

The yqhC gene in LY180 was replaced with a kanamycin-resistance cassette to create LY180ΔyqhC. Furfural tolerance of the LY180 and the deleted strain were compared using the BioScreen C growth curve analyzer. The resulting plots (FIGS. 21A and B) clearly demonstrated that LY180ΔyqhC is more resistant than the parent at 1.0, 1.5 and 2 g liter$^{-1}$ furfuralIt was also confirmed that the change in furfural resistance was caused by the mutation in yqhC by introducing a plasmid-borne copy (pLOI4901) of the wild type yqhC gene with its native promoter, fully restoring furfural sensitivity (FIG. 21C). The presence of empty vector (pCC1) in LY180ΔyqhC had no effect on furfural sensitivity (FIG. 21D). Mutation of yqhC either by insertion of IS10 (in EMFR9) or by complete deletion (in LY180ΔyqhC) resulted in increased furfural tolerance.

The in vivo rates of furfural reduction were examined during fermentation. The rate of furfural reduction by strain LY180 (0.042±0.001 μmol min$^{-1}$ mg dcw$^{-1}$) was significantly higher (68%; p<0.05) than by strain LY180ΔyqhC (0.025±0.005 μmol min$^{-1}$ mg dcw$^{-1}$), consistent with induction of YqhD and DkgA in only the parental strain.

Example 12

Transcriptional Regulation of the yqhD Promoter (Luciferase Reporter)

Figure 22A:
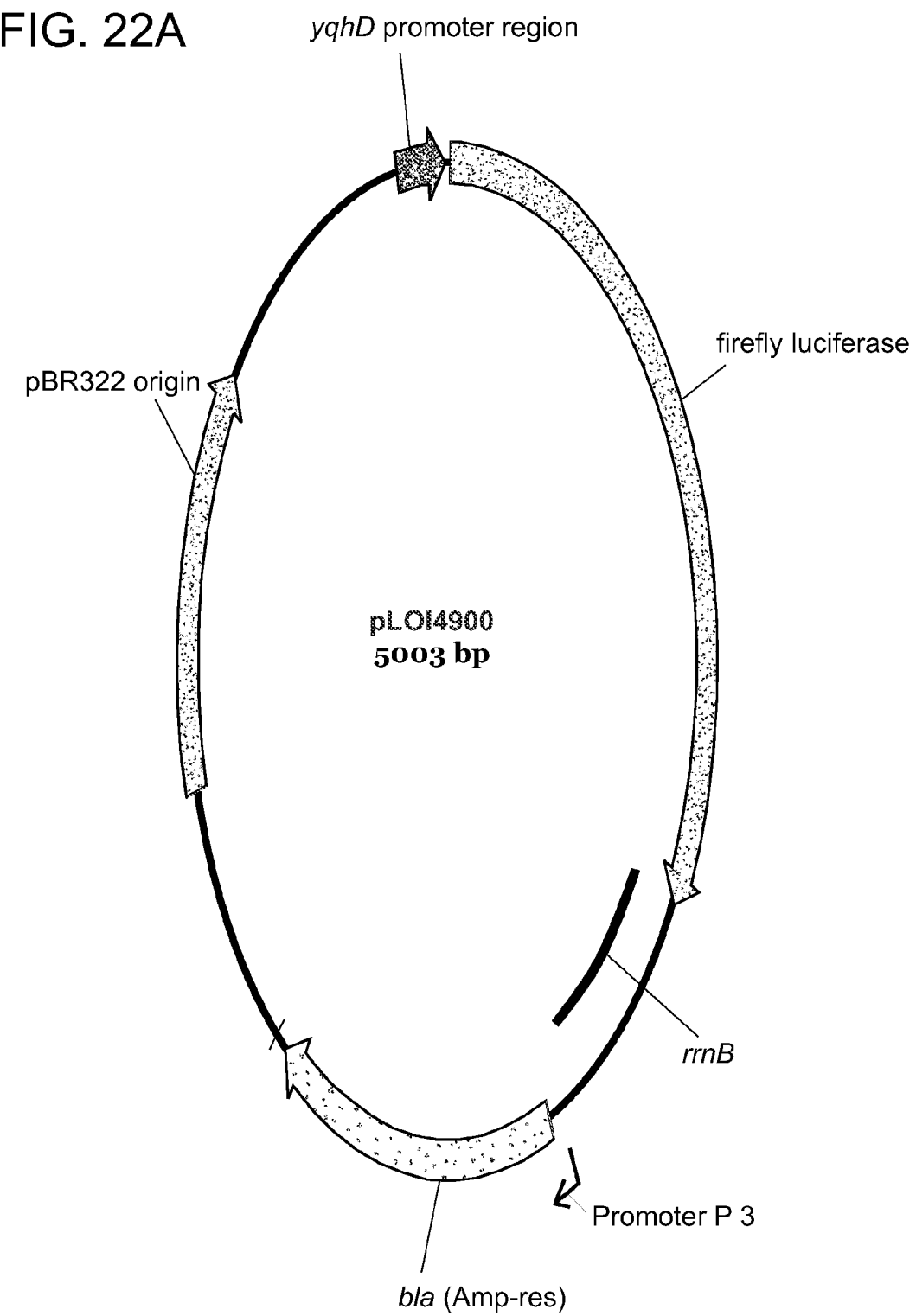
FIGS. 22A-C. Measurement of yqhD promoter activity using the firefly luciferase reporter. (A) The structure of the plasmid pLOI4900 carrying the firefly luciferase gene fused to the promoter region upstream from yqhD. (B) Effect of furfural addition on firefly luciferase expression from the yqhD promoter in LY180. Cultures of LY180 carrying pLOI4900 were grown in AM1-50 g liter$^{-1}$ xylose to OD$_{550}$=0.4, and samples taken immediately before (t=0) and at 5, 15, and 30 minutes after addition of 0, 0.1, 0.5, and 1 g liter$^{-1}$ furfural. Luciferase activity is expressed as relative luminescence units (RLU) per 0.4 OD$_{550}$ units. Error bars indicate SEM. (C) Firefly luciferase expression from the yqhD promoter in LY180ΔyqhC/pLOI4900. Conditions and symbols as for FIG. 22B.
Figure 22B:
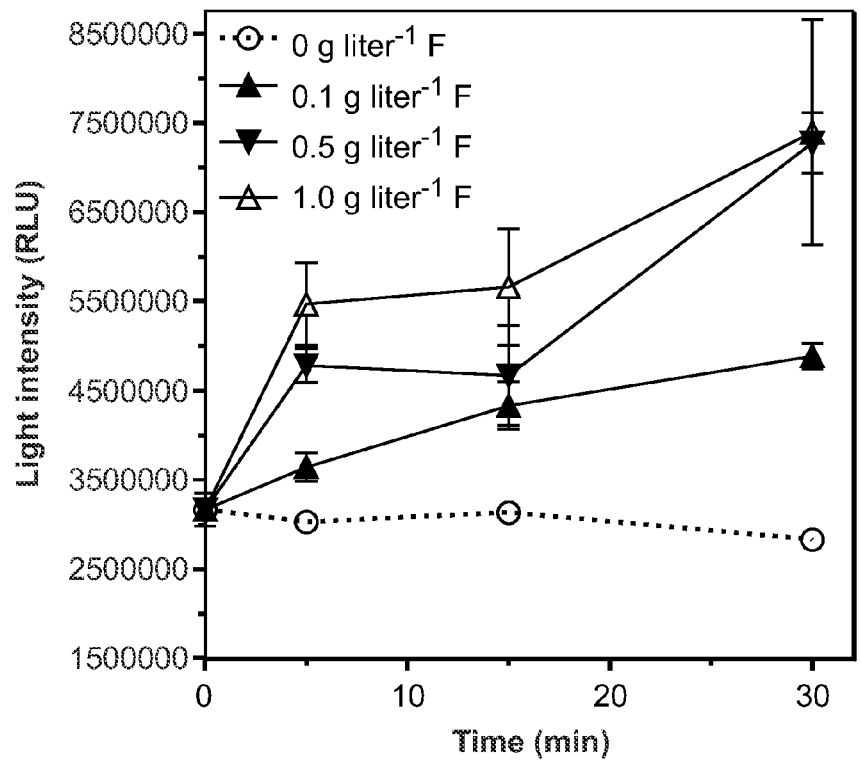
Figure 22C:
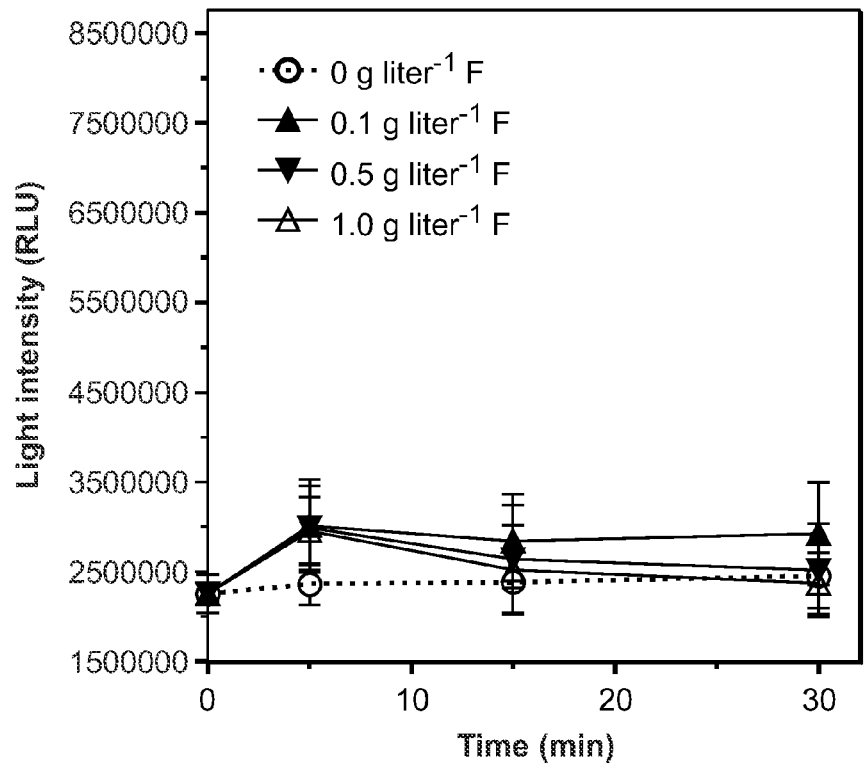

Plasmid pLOI4900 was constructed with the yqhD promoter region (151 bp) immediately upstream from a firefly luciferase reporter (FIG. 22A). This plasmid was used to investigate transcriptional regulation in the parent LY180 and LY180ΔyqhC. With LY180(pLOI4900), addition of furfural (1 mM, 5 mM, and 10 mM) resulted in a dose-dependent increase in luciferase activity that was evident within 5 min (FIG. 22B). In the yqhC deletion strain harboring this plasmid, no furfural-dependent response was observed (FIG. 22C). A steady state level of expression was observed in both strains but was lower in LY180ΔyqhC.

EMFR9 carrying pLOI4900 gave similar results (not shown) to those with LY180ΔyqhC(pLOI4900). The basal level of luciferase activity in the absence of furfural was low, and addition of furfural did not increase luciferase activity. No luciferase activity was detected in the absence of pLOI4900.

Other aldehydes known to be present in dilute acid hydrolysates of hemicellulose (Palmqvist et al. 2000 Biores. Technol. 74:25-33) were also tested at various concentration using LY180(pLOI4900) and LY180ΔyqhC (pLOI4900). All increased luciferase activity by 2-fold to 5-fold in LY180(pLOI4900) (data not shown). These included acetaldehyde (1 mM), propionaldehyde (1 mM), butyraldehyde (1 mM), 5-hydroxymethyl furfural (1 mM), and cinnamaldehyde (0.1 mM). Methylglyoxal (0.1 mM) was also found to increase luciferase activity in LY180 (pLOI4900). None of these compounds increased luciferase activity in LY180ΔyqhC.

Together, these results demonstrate that YqhC is a required, trans-active transcriptional activator for aldehyde-inducible expression from the yqhD promoter. Mutations of yqhC (IS10 insertion or deletion) eliminated the aldehyde-induced increase in transcription.

Example 13

Effect of a yqhC Deletion on Transcript Levels

Figure 20B:
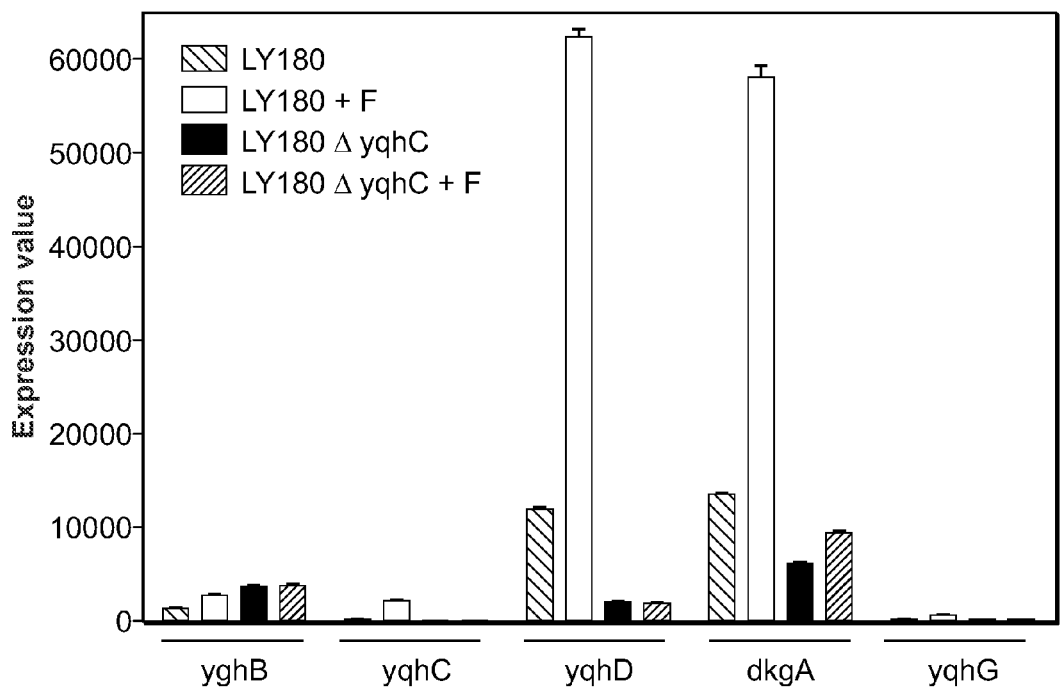

Total RNA was prepared from strains LY180 and LY180ΔyqhC immediately before and 15 min after the addition of 0.5 g liter$^{-1}$ furfural. Expression results for the yqhC-yqhD-dkgA region together with flanking genes yghB (conserved inner membrane protein) and yqhG (unknown function) are shown in FIG. 20B. In LY180, expression of yqhC, yqhD, and dkgA transcripts was up-regulated by the addition of furfural, as expected. This furfural response was absent in LY180ΔyqhC. Flanking genes were expressed at low levels and were less affected. The low level of apparent expression of yqhC in LY180ΔyqhC was similar to that observed for other gene deletions in LY180 such as ldhA, adhE, and frdBC, and reflected the background level of hybridization obtained with the *E. coli* K12 chip. These data are consistent with YqhC acting as a positive regulator of transcription from the yqhD promoter.

The presence of transcripts extending through the intergenic region between yqhD and dkgA was investigated by qPCR, using primers flanking the yqhD-dkgA gap. cDNA derived from RNA of LY180 cells grown without furfural was used as a template. A PCR product of the expected size for bridging the gap between the genes was recovered, and the quantity was only slightly less than that for a PCR product made with primers internal to yqhD (data not shown). Transcription from the yqhD promoter therefore appears to extend into the adjacent dkgA gene. The quantity of dkgA transcripts was higher than that seen for either yqhD or the yqhD-dkgA intergenic region, consistent with experimental evidence indicating the presence of an additional dkgA promoter (Gama-Castro et al. 2008 Nucleic Acids Res 36: D120-D124).

The question of whether YqhC regulates other regions besides the one adjacent to the yqhC gene was addressed by searching all of the microarray data for additional genes that are differentially expressed upon deletion of yqhC. A comparison of the expression levels for the 4,237 genes represented on the TI8333 microarray chip revealed that there are a total of 72 genes with expression differences of 2-fold greater or more between LY180 and LY180ΔyqhC in the absence of furfural. Of these, 41 were down-regulated in LY180ΔyqhC and 31 up-regulated. In the presence of furfural (0.5 g liter$^{-1}$), 134 genes were differentially regulated at the 2-fold level (32 down-regulated and 102 up-regulated in LY180ΔyqhC). A total of 34 genes differed in expression by 2-fold or more in both data sets (24 down-regulated in both sets, and 10 up-regulated in both sets). Genes down-regulated in LY180ΔyqhC under both conditions included yqhC, yqhD, dkgA, the tauABCD and ssuEADCB operons, the regulators cbl and nac, and others (fimC, mdaB, rspA, ybaY, ybeH, ycdF, ydhP, yeeO, yjfyY, and ymcD). Genes up-regulated by 2-fold or more in LY180ΔyqhC compared with LY180 under both conditions included cueO, copA, and cusCFB, which function in copper metabolism; and chbB, gdhA, hipB, ydeU, and ydeK.

The expression levels of these 34 genes were analyzed in previous datasets (Miller et al. 2009 Appl Environ. Microbiol. 75: 6132-6141; Miller et al. 2009 Appl. Environ. Microbiol. 75: 4315-4323) which compared LY180 and EMFR9 (IS10 insertion in yqhC) in the presence and absence of furfural. We reasoned that IS10 inactivation of yqhC in EMFR9 should result in the changes similar to those caused by the yqhC deletion (in LY180ΔyqhC). In all of the datasets examined, expression of yqhD and dkgA was consistently reduced in EMFR9 in comparison with LY180, both in the absence and presence of furfural. The fold reduction in yqhD expression with furfural for EMFR9 in comparison with LY180 was at least 6.0-fold and for dkgA at least 10.6-fold. However, the down-regulation by 2-fold or more for the tauABCD and ssuEADCB operons, cbl, and other genes was not observed for EMFR9 relative to LY180. The ten genes that were up-regulated in LY180ΔyqhC were not up-regulated in EMFR9. No genes, other than yqhC, yqhD and dkg, were consistently up- or down-regulated in the absence of a functional YqhC protein.

Example 14

Orthologs of yqhC and Associated Genes in Other Bacterial Genera

The presence of yqhC orthologs and relatives of the yqhD and dkgA genes in bacteria other than *E. coli* was investigated by searching genomes available at EcoCyc (Keseler et al. 2009 Nucleic Acids Res 37: D464-D470). Of the 46 genera containing orthologs of *E. coli* yqhC, 40 were Gram-negative organisms. The proximity of genes resembling yqhD and dkgA to yqhC orthologs was examined using the EcoCyc multigenome browser (FIG. 23). Most genera (34 of 46 genera) did not contain any recognizable yqhD or dkgA orthologs near the yqhC ortholog (*Acinetobacter* sp. and *Xanthomonas campestris* for example) including all of the Gram-positive organisms. However, 24 of these 34 genera did contain either a yqhD or dkgA ortholog elsewhere in the genome. Five of the 46 genera contained a nearby yqhD ortholog in addition to yqhC but no dkgA ortholog (*Aeromonas hydrophila* and *Vibrio parahaemolyticus* for example), and one (*Thermotoga maritima*, not shown) contained a nearby dkgA ortholog without a nearby yqhC ortholog. Five genera contained all three genes with an arrangement similar to *E. coli*. This group was limited to the Enterobacteriaceae and included: *Escheri-*

*chia, Shigella, Salmonella, Klebsiella, Pectobacterium,* and *Yersinia*. The arrangement of the genes in *P. atrosepticum* was unusual in that there was a probable nitroreductase gene, ECA0351, between the yqhC ortholog (ECA0352) and the yqhD ortholog (ECA0350).

Example 15

Strain EMFR9 Exhibits Increased Tolerance to 5-HMF

Mutations present in the furfural-resistant mutant, EMFR9, also increased resistance to 5-HMF (FIG. 24). At 1.0 g l$^{-1}$ 5-HMF, growth and ethanol production by EMFR9 were equal to that of LY180 (parent) in the absence of 5-HMF (FIG. 24A, 24B). 5-HMF was rapidly metabolized by EMFR9 during the initial 24 h of fermentation with no detrimental effect on cell yield or ethanol yield. The growth of LY180 was completely inhibited by 1.0 g l$^{-1}$ 5-HMF, although 5-HMF levels declined slowly during incubation (FIGS. 24A, 24B, and 24C). No decline was observed without inoculation (data not shown) confirming that this is the result of metabolic activity.

With EMFR9, ethanol production and growth were slowed by inclusion of 2.5 g 5-HMF l$^{-1}$ but proceeded to completion after 96 h (FIGS. 24D, 24E, and 24F). Cell and ethanol yields with this higher level of 5-HMF were comparable to LY180 without 5-HMF. The level of 5-HMF declined rapidly and completely with EMFR9. With LY180, metabolism of 5-HMF was slow and incomplete (FIG. 24F).

Example 16

Effects of YqhD and DkgA on 5-HMF Tolerance

Figure 25A:
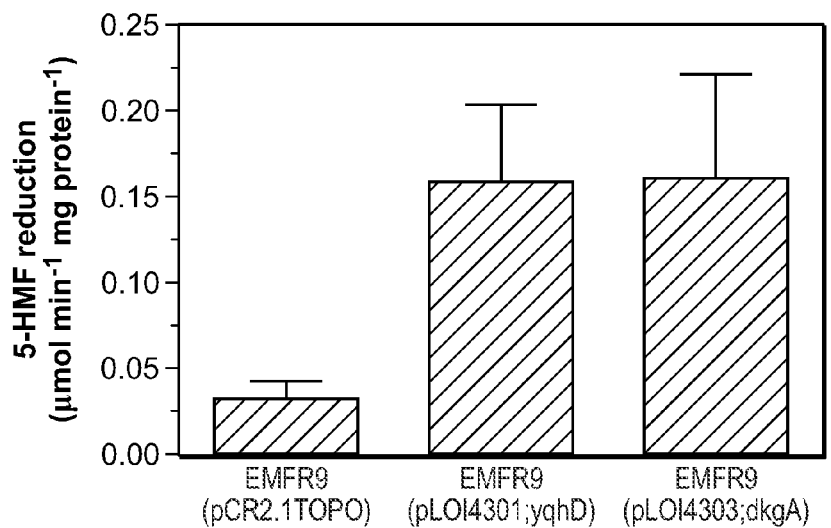
FIGS. 25A-C. Effect of YqhD and DkgA on the in vitro reduction of 5-HMF and on 5-HMF tolerance. A. Specific activity for 5-HMF reduction in vitro. Activity was measured in lysed cell extracts (2 mM NADPH, 20 mM 5-HMF). B. Effect of yqhD and dkgA expression from plasmids on the cell yield of EMFR9 (resistant mutant). Experiments were performed in tube cultures with AM1 medium containing 50 g l$^{-1}$ xylose and 1.0 g l$^{-1}$ 5-HMF (48 h incubation). Note that inclusion of kanamycin for plasmid maintenance lowers 5-HMF tolerance. Induced (Ind.) were grown with 0.1 mM IPTG. C. Effect of yqhD and dkgA deletions on the cell yield of LY180 (parent). Experiments were performed in tube cultures with AM1 medium containing 50 g l$^{-1}$ xylose and 2.5 g l$^{-1}$ 5-HMF (48 h incubation). All data are plotted as a mean with standard deviation (n=4).

Furfural tolerance in EMFR9 was previously demonstrated to result from the silencing of two NADPH-dependent oxidoreductases, YqhD and DkgA (Miller et al. 2009b Appl Environ Microbiol 75: 4315-4323). Genes encoding these activities were cloned into pCR2.1 TOPO, transformed into EMFR9, and induced with 0.1 mM IPTG. Cells were harvested, disrupted, and tested for 5-HMF reductase activity (FIG. 25A). Expression of yqhD and dkgA individually from plasmids resulted in a 5-fold increase in the rate of 5-HMF-dependent oxidation of NADPH, confirming that YqhD and DkgA use 5-HMF as a substrate.

Figure 25B:
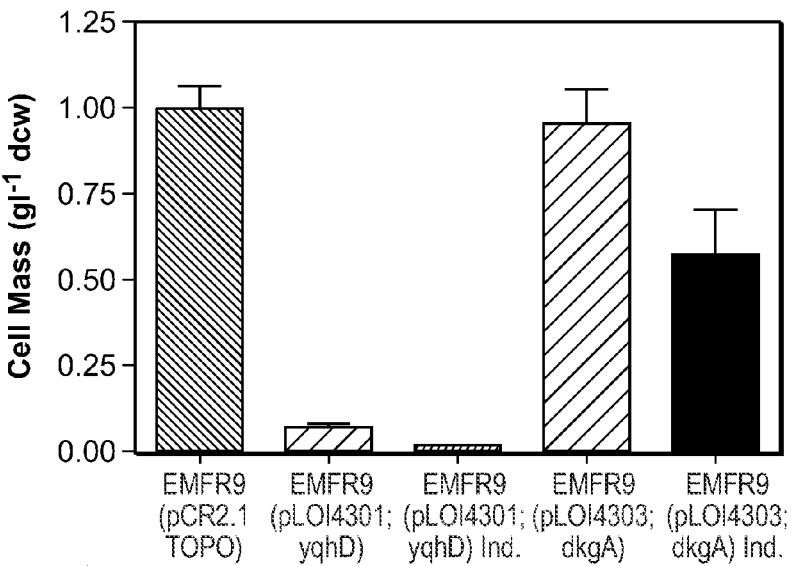

The individual expression of yqhD and dkgA from plasmids decreased the tolerance of EMFR9 to 5-HMF (FIG. 25B). Addition of kanamycin (12.5 mg l$^{-1}$) for plasmid maintenance decreased 5-HMF tolerance in all strains, requiring the use of a lower concentration of 5-HMF (1.0 g l$^{-1}$) in this experiment. Plasmid pCR2.1 is leaky for the expression of cloned genes in the absence of IPTG (Purvis et al. 2005 Appl Environ Microbiol 71:3761-3769). Even uninduced expression of yqhD was sufficient to restore the sensitivity of EMFR9 to 5-HMF. Growth inhibition by 5-HMF was further increased by yqhD induction. Expression of dkgA was less effective and required induction to restore 5-HMF sensitivity in EMFR9. Differences in effectiveness between these two oxidoreductases are consistent with the lower apparent $K_m$ of YqhD (8 µM) for NADPH compared to 23 µM for DkgA (Miller et al. 2009b Appl Environ Microbiol. 75: 4315-4323).

Figure 25C:
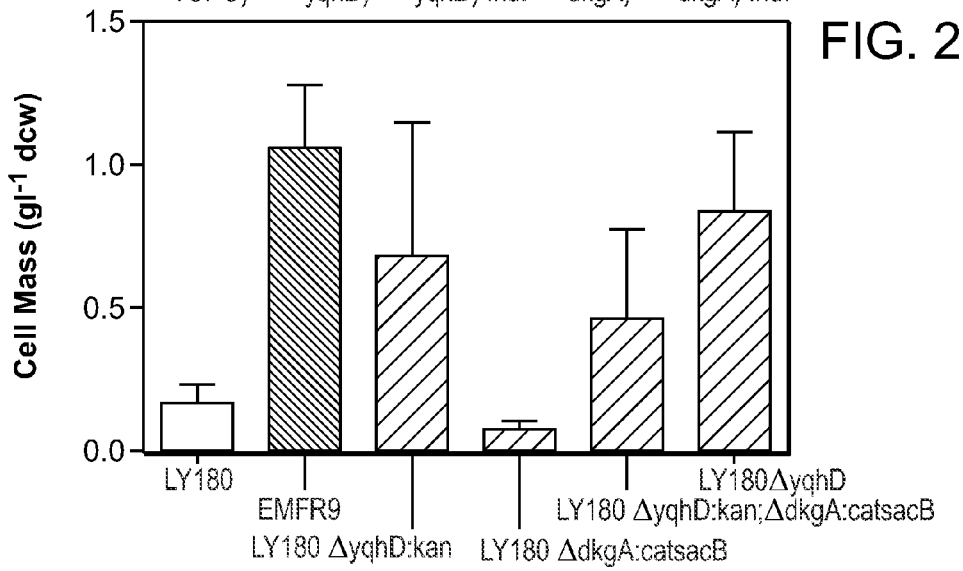

Deletion of yqhD from LY180 increased tolerance to 2.5 g l$^{-1}$ 5-HMF (FIG. 25C). Deletions in which markers remained in the chromosome were less effective but confirmed that the inactivation of yqhD was beneficial for 5-HMF tolerance in all cases.

Example 17

Increasing the Availability of NADPH Increased 5-HMF Tolerance

Figure 26A:
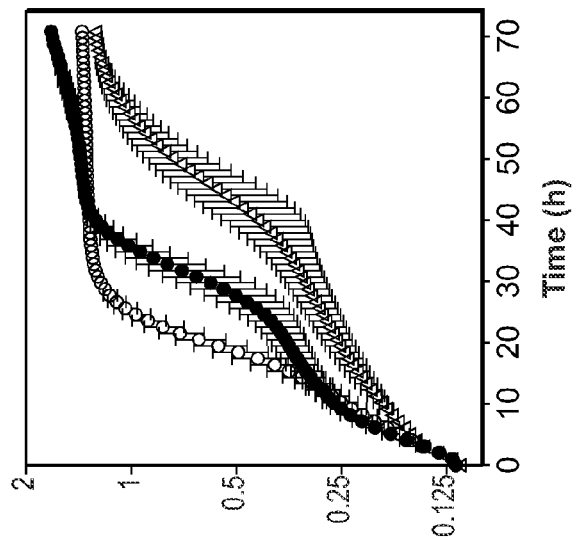
FIGS. 26A-C. Effect of pntAB expression from plasmids on 5-HMF tolerance. Experiments were conducted using the Bioscreen C growth curve analyzer with AM1 medium containing 50 g l$^{-1}$ xylose and 5-HMF as indicated. All data are plotted as a mean with standard deviation (n=10). Connecting points have been omitted for clarity. A. No supplement; B. Supplemented with 0.9 g l$^{-1}$ 5-HMF; and C. Supplemented with 1.8 g l$^{-1}$ 5-HMF. Symbols for all: Δ, LY180 (pTrc99a-control); ○, LY180 (pTrc99a-pntAB) uninduced; ●, LY180 (pTrc99a-pntAB) induced with 0.01 mM IPTG.
Figure 26B:
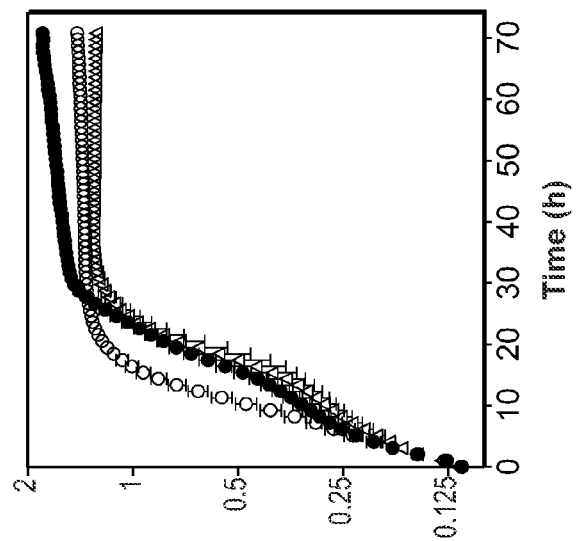
Figure 26C:
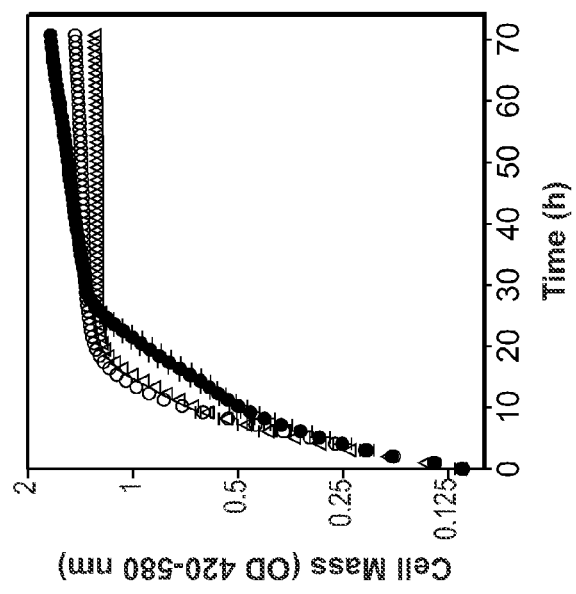

The proton-translocating transhydrogenase pntAB (Keseler et al. 2009 Nucleic Acids Res 37: D464-70) was overexpressed in LY180 (FIG. 26) to increase the availability of NADPH. In the absence of inhibitor (FIG. 26A), both LY180 with the vector (control) and LY180 (pTrc99a pntAB) grew at the same rate. Induction of LY180 (pTrc99a-pntA) with IPTG (0.01 mM) was detrimental in the absence of 5-HMF. Uninduced LY180 (pTcr99a pntAB), however, grew more rapidly than the vector control (FIGS. 26B and 26C) in the presence of 5-HMF (0.9 g l$^{-1}$ and 1.8 g l$^{-1}$). A similar benefit of pntAB was observed previously with furfural (Miller et al. 2009b). Thus the inhibition of growth by both furans appears to result from furan reduction, depleting the pool of NADPH required for biosynthesis. In addition, over-expression of pntAB led to an increase in overall growth after 72 h, even in the absence of furfural, indicating that biosynthesis may be limited by NADPH under these conditions.

Figure 27A:
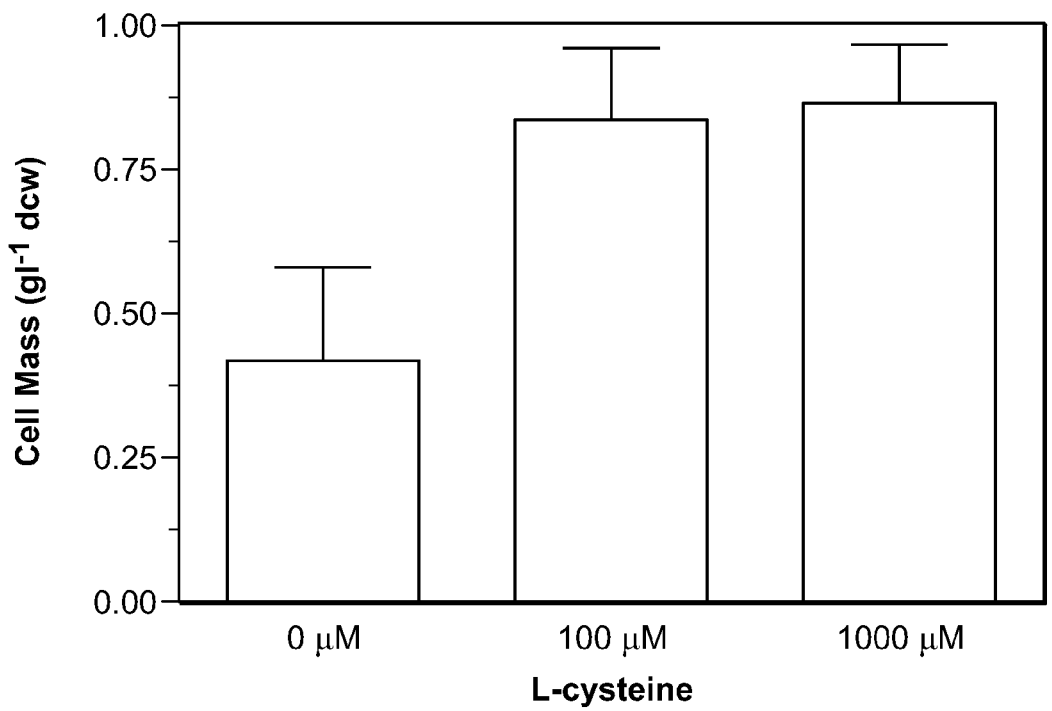
FIG. 27. Effect of L-cysteine on 5-HMF tolerance of LY180. Experiments were performed in tube cultures with AM1 medium containing 50 g l$^{-1}$ xylose and 5-HMF (24 h incubation). Cultures were supplemented with filter-sterilized L-cysteine as indicated. All data are plotted as a mean with standard deviation (n=4). A. 1.0 g l$^{-1}$ 5-HMF; B. 2.0 g l$^{-1}$ 5-HMF.
Figure 27B:
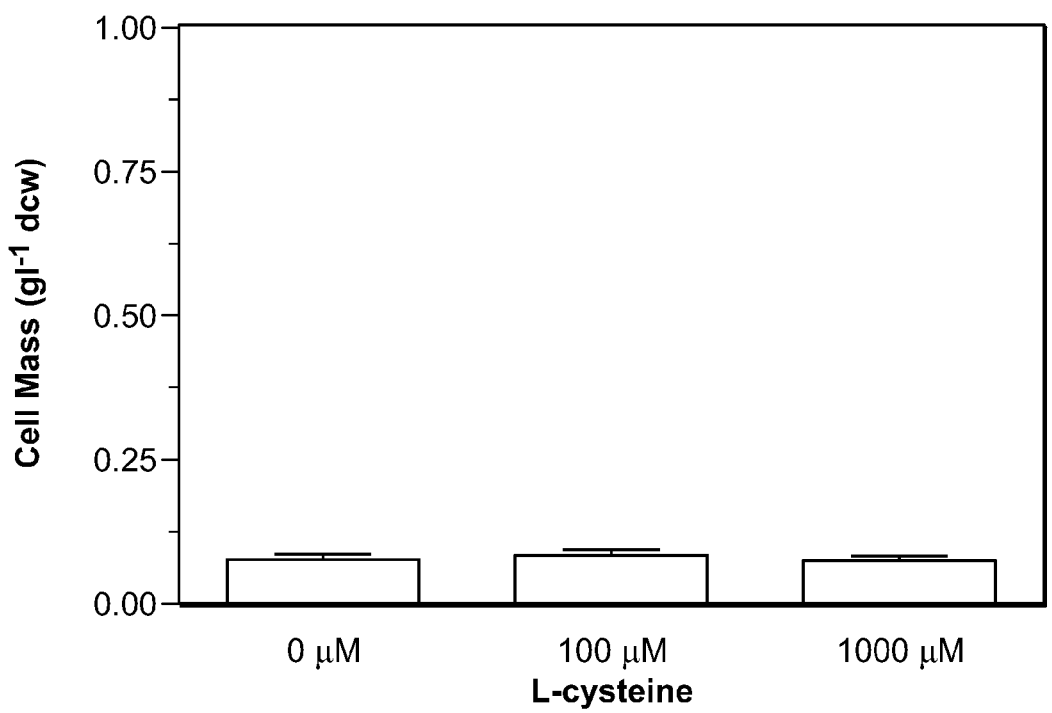
Figure 28:
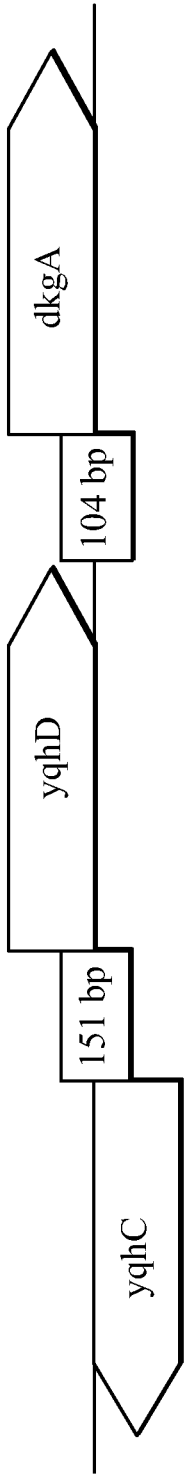
FIG. 28. Promoter orientation and alignment for yqhD (SEQ ID NO: 71) and dkgA (SEQ ID NO: 72).

Sulfur assimilation and cysteine biosynthesis have a particularly high requirement for NADPH. Supplementing with cysteine was previously shown to increase furfural tolerance in *E. coli* LY180 (Miller et al. 2009a Appl Environ Microbiol 75: 6132-6141) but was found to be of less benefit for 5-HMF tolerance (FIG. 27). Growth of LY180 was partially inhibited by 1 g l$^{-1}$ 5-HMF and completely restored by supplementing with 100 µM cysteine. Growth in the presence of 2.5 g l$^{-1}$ 5-HMF was not restored by 100 µM or 1000 µM cysteine (FIG. 27B). Unlike furfural, cysteine supplements did not increase the MIC for 5-HMF.

EQUIVALENTS

Those skilled in the art will recognize, or be able to ascertain using no more than routine experimentation, many equivalents to the specific embodiments of the invention described herein. Such equivalents are intended to be encompassed by this invention.

INCORPORATION BY REFERENCE

All publications, patent applications and patents identified herein are expressly incorporated herein by reference in their entirety.

What is claimed is:

1. An isolated *Escherichia coli* (*E. coli*) bacterium, wherein said *E. coli* bacterium has a deletion or inactivation of dkgA and yqhD genes so that the expression of dkgA and yqhD genes is eliminated or the activity of DkgA and YqhD proteins is eliminated and the isolated *E. coli* bacterium has increased resistance to furfural as compared to a wild-type *E. coli* bacterium.

2. The isolated *E. coli* bacterium of claim 1, wherein said *E. coli* bacterium is ethanologenic.

3. The isolated *E. coli* bacterium of claim 1, wherein said *E. coli* bacterium has increased ethanol production as compared to the wild-type *E. coli* bacterium.

4. The isolated *E. coli* bacterium of claim 1, wherein the isolated *E. coli* bacterium further comprises deletion or inactivation of yqhC gene so that the expression of yqhC gene is eliminated or the activity of YqhC protein is eliminated.

5. The isolated *E. coli* bacterium of claim 1 wherein said isolated *E. coli* bacterium is capable of producing ethanol and wherein said *E. coli* bacterium is prepared by a process comprising the steps of:
 a) growing an isolated *E. coli* bacterium in the presence of:
  (1) furfural or
  (2) increasing concentrations of furfural; and
 b) selecting an isolated *E. coli* bacterium that produces ethanol in the presence of furfural, and
 wherein the selected isolated *E. coli* bacterium has a deletion or inactivation of dkgA and yqhD genes so that the expression of dkgA and yqhD genes is eliminated or the activity of DkgA and YqhD proteins is eliminated and the isolated *E. coli* bacterium has increased resistance to furfural as compared to a wild-type *E. coli* bacterium.

6. A method for producing ethanol from a biomass, a hemicellulosic biomass, a lignocellulosic biomass, a cellulosic biomass or an oligosaccharide source comprising contacting the biomass, hemicellulosic biomass, lignocellulosic biomass, cellulosic biomass or oligosaccharide with the isolated *E. coli* bacterium of claim 1, thereby producing ethanol from the biomass, hemicellulosic biomass, lignocellulosic biomass, cellulosic biomass or oligosaccharide source.

7. The method of claim 6, wherein the biomass, hemicellulosic biomass, lignocellulosic biomass, cellulosic biomass or oligosaccharide source comprises furfural.

8. A kit comprising the isolated *E. coli* bacterium of claim 1 and instructions for use.

9. An isolated gram-negative bacterium of the genus *Escherichia, Salmonella*, and *Klebsiella*, wherein said gram-negative bacterium has a deletion or inactivation of dkgA gene and yqhD gene so that the expression of dkgA and yqhD genes is eliminated or the activity of DkgA and YqhD proteins is eliminated and the isolated gram-negative bacterium has increased resistance to furfural as compared to a corresponding wild-type gram-negative bacterium of the genus *Escherichia, Salmonella*, or *Klebsiella*.

10. The isolated *E. coli* bacterium of claim 1, wherein the deletion or inactivation of the dkgA or yqhD gene comprises deletion of the dkgA or yqhD gene promoter; replacement of the dkgA or yqhD gene promoter by a different promoter; inserting, substituting or removing nucleic acids in the dkgA or yqhD gene promoter; inserting or removing regulatory elements of the dkgA or yqhD gene; or inserting or removing motifs in the dkgA or yqhD gene promoter such that expression of DkgA or YqhD protein is eliminated.

11. The isolated gram-negative bacterium of claim 9, wherein the deletion or inactivation of the dkgA or yqhD gene comprises deletion of the dkgA or yqhD gene promoter; replacement of the dkgA or yqhD gene promoter by a different promoter; inserting, substituting or removing nucleic acids in the dkgA or yqhD gene promoter; inserting or removing regulatory elements of the dkgA or yqhD gene; or inserting or removing motifs in the dkgA or yqhD gene promoter such that expression of DkgA or YqhD protein is eliminated.

12. An *Escherichia coli* (*E. coli*) strain identified as EMFR9, wherein the *E. coli* strain has the Agricultural Research Culture Collection deposit number NRRL B-50240.

* * * * *

SEQUENCE LISTING

```
<160> NUMBER OF SEQ ID NOS: 74

<210> SEQ ID NO 1
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 1
acatcaggca gatcgttctc                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccacagctta gtggtgatga                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggagagccga atcatgtcta                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccggaacctg tctcaaccaa                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcctgctccg gtgagttcat                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccggctctgc atgatgatgt                                                   20

<210> SEQ ID NO 7
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 7
gctggagagg tatacatgtg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccgtattcg ctcgaagagt                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgcagcaca tgcaacttga                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atggcgctgc cgaccaatga                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgcatctgt atcgccggtt                                              20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccgatgcga gcatgattcg t                                            21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
attatcgagt ggaaagatat                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtagtctcc gttctgctta                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acctttcttt tttttgcct                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttacgaccgc tgccggaatc                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttattgcgac gcctgccgtt                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttcaatcac cgcttcttcg                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cctgccatgc tctacacttc                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctggttagat ggcgactatg                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aacttatctg ataacactaa                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccaacagcgg cgacaatgta                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcaggctgct gaattgtcag                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggcaccagat ccagttaatg                                               20

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
gttctctgcc ctcatattgg cccagcaaag ggagcaagta gtgtaggctg gagctgcttc    60

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gacgaaatgc ccgaaaacga aagtttgagg cgtaaaaagc catatgaata tcctcctta    59

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
acggttggat tagccatacg                                                20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gaccagttcg gcggctaaca                                                20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcctgctccg gtgagttcat                                                20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccggctctgc atgatgatgt                                                20

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
```
tgactctcga gatgaacaac tttaatctgc a                                           31

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agtcaggatc cttagcgggc ggcttcgtat a                                           31

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atatgcctcg agatggctaa tccaaccgtt at                                          32

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccgataggat ccttagccgc cgaactggtc agg                                         33

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cggcgaggta ctggtgac                                                          18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
catgttagcc gccgaact                                                          18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
tcatgttggc ttctgccg                                                 18
```

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

```
gcgcaatcgc tggtttac                                                 18
```

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
gttccgatga tgagcgtatt g                                             21
```

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
aggcgttttc gatcagaaag                                               20
```

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
ccagcaaccg gttcagaat                                                19
```

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
aacgcgtgaa aatagcgact                                               20
```

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
gcggtaaaga gattaaaagc gc                                            22
```

```
<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tatggctaat ccaaccgtta ttaag                                              25

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cccgcccgtt gttactct                                                      18

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccatccgcga cgagtctgaa                                                    20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggtgaagcgg aactgaacaa                                                    20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccatccgcga cgagtctgaa                                                    20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cgacgctcta tcacgccatt                                                    20
```

```
<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgcgctgttt aagatcgct                                               19

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
catgattgcc ttctcggg                                                18

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
actgagatga tctcaagcga ttg                                          23

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggaaacaacg cgagatacct                                              20

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ccacgctggc agaaaccta                                               19

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcgtatgcat gcaattttgt agcatttctc cagc                              34
```

```
<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gcggaattct acttgctccc tttgctggg                                           29

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
atggtccata tgaatatcct ccttag                                              26

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gagctcgagt aggctggagc tgcttc                                              26

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gagctcgaga tgcggcaatt tgattgtgcg c                                        31

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gtttcacggc gttcatcagc g                                                   21

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtctgggctg ctggctaag                                                      19

<210> SEQ ID NO 62
```

-continued

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tttcataagc cgggtttggc tc                                              22

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gacgattttc cccgttcccg gctgctgtac cgggaacgta t                         41

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
catatgaata tcctcctta                                                  19

<210> SEQ ID NO 65
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Asn Asn Phe Asn Leu His Thr Pro Thr Arg Ile Leu Phe Gly Lys
 1               5                  10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
```

```
                      165                 170                 175
Pro Val Tyr Thr Tyr Thr Leu Pro Pro Arg Gln Val Ala Asn Gly Val
                180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
        210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
                260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
        290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
        370                 375                 380

Ala Ala Arg
385

<210> SEQ ID NO 66
<211> LENGTH: 1164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
atgaacaact ttaatctgca caccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
accaaattta tcgccgcagc ggctaactat ccggaaaata tcgatccgtg gcacattctg     360
caaacgggcg gtaaagagat taaagcgcc atcccgatgg gctgtgtgct gacgctgcca     420
gcaaccggtt cagaatccaa cgcaggcgcg gtgatctccc gtaaaaccac aggcgacaag     480
caggcgttcc attctgccca tgttcagccg gtatttgccg tgctcgatcc ggtttatacc     540
tacaccctgc cgccgcgtca ggtggctaac ggcgtagtgg acgcctttgt acacaccgtg     600
gaacagtatg ttaccaaacc ggttgatgcc aaaattcagg accgtttcgc agaaggcatt     660
ttgctgacgc taatcgaaga tggtccgaaa gccctgaaag agccagaaaa ctacgatgtg     720
```

```
cgcgccaacg tcatgtgggc ggcgactcag gcgctgaacg gtttgattgg cgctggcgta    780
ccgcaggact gggcaacgca tatgctgggc cacgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa aatcatgaca ttacgttgga tgtcagccgc   1140
cgtatatacg aagccgcccg ctaa                                          1164
```

<210> SEQ ID NO 67
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Met Ala Asn Pro Thr Val Ile Lys Leu Gln Asp Gly Asn Val Met Pro
1               5                   10                  15

Gln Leu Gly Leu Gly Val Trp Gln Ala Ser Asn Glu Glu Val Ile Thr
            20                  25                  30

Ala Ile Gln Lys Ala Leu Glu Val Gly Tyr Arg Ser Ile Asp Thr Ala
        35                  40                  45

Ala Ala Tyr Lys Asn Glu Glu Gly Val Gly Lys Ala Leu Lys Asn Ala
    50                  55                  60

Ser Val Asn Arg Glu Glu Leu Phe Ile Thr Thr Lys Leu Trp Asn Asp
65                  70                  75                  80

Asp His Lys Arg Pro Arg Glu Ala Leu Leu Asp Ser Leu Lys Lys Leu
                85                  90                  95

Gln Leu Asp Tyr Ile Asp Leu Tyr Leu Met His Trp Pro Val Pro Ala
            100                 105                 110

Ile Asp His Tyr Val Glu Ala Trp Lys Gly Met Ile Glu Leu Gln Lys
        115                 120                 125

Glu Gly Leu Ile Lys Ser Ile Gly Val Cys Asn Phe Gln Ile His His
    130                 135                 140

Leu Gln Arg Leu Ile Asp Glu Thr Gly Val Thr Pro Val Ile Asn Gln
145                 150                 155                 160

Ile Glu Leu His Pro Leu Met Gln Gln Arg Gln Leu His Ala Trp Asn
                165                 170                 175

Ala Thr His Lys Ile Gln Thr Glu Ser Trp Ser Pro Leu Ala Gln Gly
            180                 185                 190

Gly Lys Gly Val Phe Asp Gln Lys Val Ile Arg Asp Leu Ala Asp Lys
        195                 200                 205

Tyr Gly Lys Thr Pro Ala Gln Ile Val Ile Arg Trp His Leu Asp Ser
    210                 215                 220

Gly Leu Val Val Ile Pro Lys Ser Val Thr Pro Ser Arg Ile Ala Glu
225                 230                 235                 240

Asn Phe Asp Val Trp Asp Phe Arg Leu Asp Lys Asp Glu Leu Gly Glu
                245                 250                 255

Ile Ala Lys Leu Asp Gln Gly Lys Arg Leu Gly Pro Asp Pro Asp Gln
            260                 265                 270

Phe Gly Gly
```

-continued

275

<210> SEQ ID NO 68
<211> LENGTH: 828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
atggctaatc caaccgttat taagctacag gatggcaatg tcatgcccca gctgggactg      60
ggcgtctggc aagcaagtaa tgaggaagta atcaccgcca ttcaaaaagc gttagaagtg     120
ggttatcgct cgattgatac cgccgcggcc tacaagaacg aagaaggtgt cggcaaagcc     180
ctgaaaaatg cctcagtcaa cagagaagaa ctgttcatca ccactaagct gtggaacgac     240
gaccacaagc gcccccgcga agccctgctc gacagcctga aaaaactcca gcttgattat     300
atcgacctct acttaatgca ctggcccgtt cccgctatcg accattatgt cgaagcatgg     360
aaaggcatga tcgaattgca aaagagggga ttaatcaaaa gcatcggcgt gtgcaacttc     420
cagatccatc acctgcaacg cctgattgat gaaactggcg tgacgcctgt gataaaccag     480
atcgaacttc atccgctgat gcaacaacgc cagctacacg cctggaacgc gacacacaaa     540
atccagaccg aatcctggag cccattagcg caaggaggga aaggcgtttt cgatcagaaa     600
gtcattcgcg atctggcaga taaatacggc aaaaccccgg cgcagattgt tatccgctgg     660
catctggata gcggcctggt ggtgatcccg aaatcggtca caccttcacg tattgccgaa     720
aactttgatg tctgggattt ccgtctcgac aaagacgaac tcggcgaaat tgcaaaactc     780
gatcagggca agcgtctcgg tcccgatcct gaccagttcg gcggctaa                  828

<210> SEQ ID NO 69
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Leu Gln Asn Cys Ala Gln Ser Asn Cys Arg Ile Ile Pro Lys Lys
1               5                   10                  15

Leu Arg Asp Met Lys Arg Glu Glu Ile Cys Arg Leu Leu Ala Asp Lys
                20                  25                  30

Val Asn Lys Leu Lys Asn Lys Glu Asn Ser Leu Ser Gly Leu Leu Pro
            35                  40                  45

Asp Val Arg Leu Leu Tyr Gly Glu Thr Pro Phe Ala Arg Thr Pro Val
        50                  55                  60

Met Tyr Glu Pro Gly Ile Ile Ile Leu Phe Ser Gly His Lys Ile Gly
65                  70                  75                  80

Tyr Ile Asn Glu Arg Val Phe Arg Tyr Asp Ala Asn Glu Tyr Leu Leu
                85                  90                  95

Leu Thr Val Pro Leu Pro Phe Glu Cys Glu Thr Tyr Ala Thr Ser Glu
                100                 105                 110

Val Pro Leu Ala Gly Leu Arg Leu Asn Val Asp Ile Leu Gln Leu Gln
            115                 120                 125

Glu Leu Leu Met Asp Ile Gly Glu Asp Glu His Phe Gln Pro Ser Met
        130                 135                 140

Ala Ala Ser Gly Ile Asn Ser Ala Thr Leu Ser Glu Glu Ile Leu Cys
145                 150                 155                 160

Ala Ala Glu Arg Leu Leu Asp Val Met Glu Arg Pro Leu Asp Ala Arg
            165                 170                 175

Ile Leu Gly Lys Gln Ile Ile Arg Glu Ile Leu Tyr Tyr Val Leu Thr
        180                 185                 190

Gly Pro Cys Gly Gly Ala Leu Leu Ala Leu Val Ser Arg Gln Thr His
    195                 200                 205

Phe Ser Leu Ile Ser Arg Val Leu Lys Arg Ile Glu Asn Lys Tyr Thr
210                 215                 220

Glu Asn Leu Ser Val Glu Gln Leu Ala Ala Glu Ala Asn Met Ser Val
225                 230                 235                 240

Ser Ala Phe His His Asn Phe Lys Ser Val Thr Ser Thr Ser Pro Leu
                245                 250                 255

Gln Tyr Leu Lys Asn Tyr Arg Leu His Lys Ala Arg Met Met Ile Ile
            260                 265                 270

His Asp Gly Met Lys Ala Ser Ala Ala Met Arg Val Gly Tyr Glu
        275                 280                 285

Ser Ala Ser Gln Phe Ser Arg Glu Phe Lys Arg Tyr Phe Gly Val Thr
290                 295                 300

Pro Gly Glu Asp Ala Ala Arg Met Arg Ala Met Gln Gly Asn
305                 310                 315

<210> SEQ ID NO 70
<211> LENGTH: 957
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atgctacaaa attgcgcaca atcaaattgc cgcattattc ctaagaaatt acgcgatatg      60
aaacgtgaag agatttgccg cttgctggcg gataaagtta ataaactgaa aaataaagaa     120
aatagtttgt caggactgtt gcccgatgtg cgtttgttgt atggcgagac gcctttcgca     180
cgtacaccgg tgatgtacga gcctggcatc ataattctct tttccgggca taaaatcggt     240
tatatcaatg aacgcgtgtt tcgttatgat gccaatgaat acctgctgct gacggtgccg     300
ttgccgtttg agtgcgaaac ctatgccacg tcagaggtgc cgctggcagg gttgcgtctc     360
aatgtcgata ttttgcagtt acaggaactg ttgatggaca ttggcgaaga tgagcatttc     420
cagccgtcga tggcagccag cgggattaac tccgccacgt tatcagaaga gatttttatgc    480
gcggcggagc ggttactcga cgtgatggag cgaccactgg atgcgcgtat tctcggcaaa    540
cagatcatcc gcgaaattct gtactacgtg ctgaccggac cttgcggcgg cgcgttactg    600
gcgctggtca gtcgccagac tcacttcagt ctgattagcc gcgtgctgaa acggattgag    660
aataaataca ccgaaaacct gagcgtcgag caactggcgg cagaagccaa catgagcgta    720
tcggcgttcc accataattt taagtctgtc accagtacct cgccgttgca gtatttgaag    780
aattaccgtc tgcataaggc gcggatgatg atcatccatg acggcatgaa ggccagcgca    840
gcagcgatgc gcgtcggcta tgaaagcgca tcgcaattta gccgtgagtt taaacgttac    900
ttcggtgtga cgccggggga agatgcggca agaatgcggg cgatgcaggg gaattaa       957

<210> SEQ ID NO 71
<211> LENGTH: 151

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gcaattttgt agcatttctc cagcactctg gaggaatagg caagacattg cagaaatga      60 gcattgagag ccagggcgct ggcgatcaca atgaaaaaca tcaggcagat cgttctctgc    120
cctcatattg gcccagcaaa gggagcaagt a                                   151

<210> SEQ ID NO 72
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72 gcttttacg cctcaaactt tcgttttcgg gcatttcgtc cagacttaag ttcacaacac      60
ctcaccggag cctgctccgg tgagttcata taaggagga acgt                      104

<210> SEQ ID NO 73
<211> LENGTH: 9048
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
atggcggaca aaaagcttga tactcaactg gtgaatgcag acgcagcaa aaaatacact       60 ctcggcgcgg taaatagcgt gattcagcgc gcttcttcgc tggtctttga cagtgtggaa    120
gccaaaaaac acgcgacgcg caatcgcgcc aatggtgagt tgttctatgg acggcgtgga    180
acgttaaccc atttctcctt acaacaagcg atgtgtgaac tggaaggtgg cgcaggctgc    240
gtgctatttc cctgcggggc ggcggcggtt gctaattcca ttcttgcttt tgtcgaacag    300
ggcgatcatg tgctgatgac caacaccgcc tatgaaccga gtcaggattt ctgtagcaaa    360
atcctcagca aactgggcgt aacgacatcg tggtttgatc cgctgattgg tgccgatatc    420
gttaagcatc tgcagccaaa cactaaaatc gtgtttctgg aatcgccagg ctccatcacc    480
atggaagtcc acgacgttcc ggcgattgtt gccgccgtac gcagtgtggc gccggatgcc    540
atcattatga tcgacaacac ctgggcagcc ggtgtgctgt ttaaggcgct ggattttggc    600
atcgatgttt ctattcaagc cgccaccaaa tatctggttg gcattcaga tgcgatgatt    660 ggcactgccg tgtgcaatgc ccgttgctgg gagcagctac gggaaaacgc ctatctgatg    720
ggccagatgg tcgatgccga taccgcctat ataaccagcc gtggcctgcg cacattaggt    780
gtgcgtttgc gtcaacatca tgaaagcagt ctgaaagtgg ctgaatggct ggcagaacat    840
ccgcaagttg cgcgagttaa ccaccctgct ctgcctggca gtaaaggcca cgaattctgg    900
aaacgagact ttacaggcag cagcgggcta ttttccttgt gcttaagaa aaaactcagt    960 aatgaagagc tggcgaacta tctggataac ttcagtttat tcagcatggc ctactcgtgg   1020
ggcgggtatg aatcgttgat cctggcgaat caaccagaac atatcgccgc cattcgccca   1080
caaggcgaga tcgattttag cgggaccttg attcgcctgc atattggtct ggaagatgtc   1140
gacgatctga ttgccgatct ggacgccggt tttgcgcgaa ttgtataaca ttgccacttt   1200

```
tggacaattt tgcagacatt taattgtgaa aagtcttaaa ttgttgcgtc cgggatcaag    1260
gcgtcccgga cgaatcagga gtacaatagg cagataaagg cttaaacgct gttccacagg    1320
aaagtccatg gctgttattc aagatatcat cgctgcgctc tggcaacacg actttgccgc    1380
gctggcggat cctcatattg ttagcgttgt ttactttgtc atgtttgcca cgctgttttt    1440
agaaaacggc ctgctgcccg cctcattttt gccaggcgac agcttgttga tactggcagg    1500
cgcattgatt gcccaggggg ttatggattt tctgcctacg attgcgattc tgaccgccgc    1560
agcaagtctg ggctgctggc taagttatat tcaggggcgc tggttaggga ataccaaaac    1620
ggtgaaaggc tggctggcac agcttcctgc taaatatcac cagcgcgcca cctgcatgtt    1680
tgaccgccac ggtctgctgg cgctgctggc tggacgtttt cttgcatttg tccgtacgct    1740
gctgccaacc atggcgggaa tttccggtct gccaaaccgc cgcttccagt ttttcaactg    1800
gttaagtgga ttgctgtggg tcagcgtggt aaccagtttt ggctatgcct aagtatgat    1860 tccgttcgtt aaacgccatg aagatcaggt aatgacgttc ctgatgatcc tgccaattgc    1920
cttgttaacc gctggcttgt taggcacgct gtttgtggtg attaaaaaaa aatactgtaa    1980
cgcctgacga ttttccccgt tcccggctgc tgtaccggga acgtatttaa ttcccctgca    2040
tcgcccgcat tcttgccgca tcttcccccg gcgtcacacc gaagtaacgt ttaaactcac    2100
ggctaaattg cgatgcgctt tcatagccga gcgcatcgc tgctgcgcta gccttcatgc    2160
cgtcatggat gatcatcatc cgcgccttat gcagacggta attcttcaaa tactgcaacg    2220
gcgaggtgct ggtgacagac ttaaaattat ggtggaacgc cgatacgctc atgttggctt    2280
ctgccgccag ttgctcgacg ctcaggtttt cggtgtattt attctcaatc cgtttcagca    2340
cgcggctaat cagactgaag tgagtctggc gactgaccag cgccagtaac gcgccgccgc    2400
aaggtccggt cagcacgtag tacagaattt cgcggatgat ctgtttgccg agaatacgcg    2460
catccagtgg tcgctccatc acgtcgagta accgctccgc cgcgcataaa atctcttctg    2520
ataacgtggc ggagttaatc ccgctggctg ccatcgacgg ctggaaatgc tcatcttcgc    2580
caatgtccat caacagttcc tgtaactgca aaatatcgac attgagacgc aaccctgcca    2640
gcggcacctc tgacgtggca taggtttcgc actcaaacgg caacggcacc gtcagcagca    2700
ggtattcatt ggcatcataa cgaaacacgc gttcattgat ataaccgatt ttatgcccgg    2760
aaaagagaat tatgatgcca ggctcgtaca tcaccggtgt acgtgcgaaa ggcgtctcgc    2820
catacaacaa acgcacatcg ggcaacagtt ctgacaaact attttcttta attttcagtt    2880
tattaacttt atccgccagc aagcggcaaa tctcttcacg tttcatatcg cgtaatttct    2940
taggaataat gcggcaattt gattgtgcgc aattttgtag catttctcca gcactctgga    3000
ggaataggca agacattggc agaaatgagc attgagagcc agggcgctgg cgatcacaat    3060
gaaaaacatc aggcagatcg ttctctgccc tcatattggc ccagcaaagg gagcaagtaa    3120
tgaacaactt taatctgcac accccaaccc gcattctgtt tggtaaaggc gcaatcgctg    3180
gtttacgcga acaaattcct cacgatgctc gcgtattgat tacctacggt ggcggcagcg    3240
tgaaaaaaac cggcgttctc gatcaagttc tggatgccct gaaaggcatg gacgtgctgg    3300
aatttggcgg tattgagcca aacccggctt atgaaacgct gatgaacgcc gtgaaactgg    3360
ttcgcgaaca gaaagtgact ttcctgctgg cggttggcgg cggttctgta ctggacggca    3420
ccaaatttat cgccgcagcg gctaactatc cggaaaatat cgatccgtgg cacattctgc    3480
aaacgggcgg taaagagatt aaaagcgcca tcccgatggg ctgtgtgctg acgctgccag    3540
```

```
caaccggttc agaatccaac gcaggcgcgg tgatctcccg taaaaccaca ggcgacaagc    3600
aggcgttcca ttctgcccat gttcagccgg tatttgccgt gctcgatccg gtttatacct    3660
acaccctgcc gccgcgtcag gtggctaacg gcgtagtgga cgcctttgta cacaccgtgg    3720
aacagtatgt taccaaaccg gttgatgcca aaattcagga ccgtttcgca gaaggcattt    3780
tgctgacgct gatcgaagat ggtccgaaag ccctgaaaga gccagaaaac tacgatgtgc    3840
gcgccaacgt catgtggggg gcgacgcagg cgctgaacgg tttgattggc gctggcgtac    3900
cgcaggactg ggcaacgcat atgctgggcc acgaactgac tgcgatgcac ggtctggatc    3960
acgcgcaaac actggctatc gtcctgcctg cactgtggaa tgaaaaacgc gagaccaagc    4020
gcgctaagct gctgcaatat gctgaacgcg tctggaacat cactgaaggt tccgatgatg    4080
agcgtattga cgccgcgatt gccgcaaccc gcaatttctt tgagcaatta ggcgtgccga    4140
cccacctctc cgactacggt ctggacggca gctccatccc ggctttgctg aaaaaactgg    4200
aagagcacgg catgacccaa ctgggcgaaa atcatgacat tacgttggat gtcagccgcc    4260
gtatatacga agccgcccgc taagcttttt acgcctcaaa ctttcgtttt cgggcatttc    4320
gtccagactt aagttcacaa cacctcaccg gagcctgctc cggtgagttc atataaagga    4380
ggaacgtatg gctaatccaa ccgttattaa gctacaggat ggcaatgtca tgccccagct    4440
gggactgggc gtctggcaag caagtaatga ggaagtaatc accgccattc aaaaagcgtt    4500
agaagtgggt tatcgctcga ttgataccgc cgcggcctac aagaacgaag aaggtgtcgg    4560
caaagccctg aaaaatgcct cagtcaacag agaagaactg ttcatcacca ctaagctgtg    4620
gaacgacgac cacaagcgcc cccgcgaagc cctgctcgac agcctgaaaa aactccagct    4680
tgattatatc gacctctact taatgcactg gcccgttccc gctatcgacc attatgtcga    4740
agcatggaaa ggcatgatcg aattgcaaaa agagggatta tcaaaagca tcggcgtgtg    4800 caacttccag atccatcacc tgcaacgcct gattgatgaa actggcgtga cgcctgtgat    4860
aaaccagatc gaacttcatc cgctgatgca acaacgccag ctacacgcct ggaacgcgac    4920
acacaaaatc cagaccgaat cctggagccc attagcgcaa ggagggaaag cgttttcga    4980 tcagaaagtc attcgcgatc tggcagataa atacggcaaa accccggcgc agattgttat    5040
ccgctggcat ctggatagcg gcctggtggt gatcccgaaa tcggtcacac cttcacgtat    5100
tgccgaaaac tttgatgtct gggatttccg tctcgacaaa gacgaactcg gcgaaattgc    5160
aaaactcgat cagggcaagc gtctcggtcc cgatcctgac cagttcggcg gctaacatgc    5220
aaattctccc ggtggcggta atgttccgct accggacttt tcagaaatca tttattcccc    5280
tcgcgtcccg cccgttgtta ctcttccttg ttcaggaatg ccaaatataa ggacatcatc    5340
atgcagagcc ggaagctctt aaaagaacaa ctcatctata tccgggataa acgcaacgga    5400
gaggtgaaaa acagatgaaa ataatacttc tgtttttagc agccctggca agttttaccg    5460
tacacgcaca gccccctca ctgaccgtag aacaaacagt ccggcatatt tatcagaact    5520
ataaatcaga tgccactgcc ccttattttg gtgaaaccgg agagcgggcg ataacttctg    5580
cgcgtattca acaggcgctt accctgaacg acaatcttac gctgccgggc aatattggct    5640
ggctggatta tgatccggtt tgtgattgtc aggattttgg cgatcggtg ctagaaagcg    5700 tagcgataac tcaaactgac gccgatcatg ccgatgccgt tgtgcgcttt cgtatcttta    5760
aagatgataa agaaaagacc acgcagacac tgaaaatggt ggcggaaaat ggtcgttggg    5820
tcattgacga tattgtcagc aatcatggca gcgtcttaca agcagttaat agcgagaatg    5880
aaaaaacgct ggccgcttta gcttcgttgc aaaaagaaca gccggaagcc tttgttgccg    5940
```

```
aactctttga acatattgct gattatagct ggccgtggac gtgggtggtt tccgactctt    6000
accgccaggc ggttaatgcc ttctataaaa ccaccttcaa gacggccaat aatcccgatg    6060
aagatatgca aatagaacgg caatttattt acgacaatcc gatctgtttt ggcgaagagt    6120
cgctattttc acgcgttgat gaaattcgag tcctggagaa aaccgccgat tccgcccgca    6180
ttcatgttcg ttttacgctg accaatggca acaacgaaga gcaagaactg gttttacagc    6240
ggcgcgaagg caagtgggaa atcgctgatt ttatccgccc gaacagcggc agcctactta    6300
agcagattga ggcaaaaacc gccgccagat taaagcaatg agctgaatta aataacaatt    6360
agccggaaca ataaataaaa gggaacacta tatgaaaacg attttcaccg tgggagttgt    6420
tgttctggca acctgcttgc tcagtggctg cgtcaatgag caaaaggtca atcagctggc    6480
gagcaatgtg caaacattaa atgccaaaat cgcccggctt gagcaggata tgaaagcact    6540
acgcccacaa atctatgctg ccaaatccga agctaacaga gccaatacgc gtcttgatgc    6600
tcaggactat tttgattgcc tgcgctgctt gcgtatgtac gcagaatgat aaaaaaatcc    6660
ccggcagcat gtcagttgcc ggggattttt tttaacgtcc aaccgccgct ttagggcgtt    6720
tcttcgcacc agcattcacc ggacgagatt gcgtagacga cgcttttttt gccgtagcag    6780
gcgtctgacg ctgagtcgcc atcggcgtat gtttcgtcaa cgccggacgg gtattgcggt    6840
tctggcgacg agcttcacgc atctcttcaa tggttggcgc aggcactaag caatcgcgac    6900
ggctgccaat cagatgcttt tgcccatcg cttccagcgc ctggcggatt aacggccagt    6960
ttgccggatc gtggtaacgc aacaacgctt tatgcaaacg acgctgtttg tcgcccttcg    7020
gtacgaagac gtcttcactc ttataaccaa tcttcgccag cgggtttttc ccggtgtaat    7080
acatggtggt tgagttcgcc agcggcgatg ggtagaagtt ctgtacctgg tcgagacgga    7140
aacgatgctt tttcagccac agcgccagat tcaccatatc ttcatcacgc gtaccggggt    7200
gcgcggagat gaaatagggg atcagatact gctctttacc tgcctgtttt gagtaagtat    7260
cgaacagctc tttaaagcgg tcatagctgc ccatgcccgg cttcatcatc ttcgataacg    7320
gcccttcttc ggtatgttcc ggggcaatct tcagataacc gccgacgtga tgggtcgcca    7380
actctttgat atagcgcgga tcttccacgg cgatgtcata acgtacgcct gaggcgatga    7440
ggattttttt aatgcctttc agatcacgcg cacggcgata gaggttgatc gtcggttcgt    7500
ggttagtgtc catgtgcgga caaatatccg gataaacgca cgacaaacgg cgacaagttt    7560
gttcagcgcg tggcgatttg cagcgcaaca tatacatgtt ggcagttggc ccaccgagat    7620
cggaaatcac gcccgtaaaa cctggaacgg tgtcgcggat cgcttcgatc tcattaatga    7680
tcgaatcttc cgaacggctc tgaataatgc gcccttcgtg ctcggtaata gaacagaaag    7740
aacagccgcc aaagcagccg cgcataatgt tgaccgaaaa acggatcatt tcgtaagccg    7800
gaatacgggc attgccatag gccggatgtg gcacgcgctt gtacggcagc gcaaaaacgc    7860
tgtccatctc ttcggtagaa agcgggatag caggcgggtt gatccacaca tagcggtcac    7920 cgtgttttttg catcaatgcg cgggcgcagc ctgggttggt ttcgtggtgc agaatgcgcg    7980
aagcatgggc gtacagcact ttatcgccct tcactttctc gaaagaaggc agcaacacgt    8040
aggttttttc ccacggtttc gggcgcggtg gctgcacggt tacggctttg gcttcctgct    8100
ttttcggtgc caccggtttg ttatccgcgc acggcaaatc ttcaccatac ggatgcggga    8160
ttgggtcgat ttttccaggg gtatcaagac gggtggaatc cacgccgctc agccaggca    8220 gcgcctcttt cacgataatc gcggtattac gcacatcgcg gatttcacta atcggctcgc    8280
```

```
ccatcgccag acggtgcgcc acctccacca gcggacgctc accgttacca aacatcagca    8340
tgtcggcttt cgaatccacc agcacggaac ggcgcacggt atcggaccag taatcataat    8400
gtgcggtacg gcgcagacta gcctcaatac cgccgaggat caccggtaca tctttccacg    8460
cctctttaca acgctgggta taaaccagtg tggcgcgatc cgggcgctta cccgcgacgt    8520
tatccggcgt gtaggcatcg tcatgacgta aacggcgatc ggcggtataa cggttgatca    8580
tcgaatccat gttgccagca gtaacaccga aaaacagatt cggtttaccc agacgcatga    8640
aatcgtcttt gctgctccag tctggctggg cgatgatccc gacgcgaaag ccctgtgctt    8700
ccagcatacg accgcaaatc gccatcccga agcttgggtg atcgacatac gcgtcgccag    8760
taaccaaaat gatgtcgcag ctatcccagc caagttgatc catctcttca cgagacatcg    8820
gcaaaaacgg tgccggtcca aaacaggcgg cccagtactg cggccaggag aacaggtcgc    8880
gatccggttg gatcagggag atagagctca ttttgcttcc agaaatgata aaaaaataat    8940
caaaggccgg ggattataag ccggaacgaa agagaaatcg aaaggtattc catactcgcc    9000
ctcctcgggc gagtatgaag attacggtac cggattgacc aaaagttg                 9048
```

<210> SEQ ID NO 74
<211> LENGTH: 3022
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
aataccaaaa cggtgaaagg ctggctggca cagcttcctg ctaaatatca ccagcgcgcc      60
acctgcatgt ttgaccgcca cggtctgctg gcgctgctgg ctggacgttt tcttgcattt     120
gtccgtacgc tgctgccaac catggcggga atttccggtc tgccaaaccg ccgcttccag     180
tttttcaact ggttaagtgg attgctgtgg gtcagcgtgg taaccagttt tggctatgcc     240
ttaagtatga ttccgttcgt taaacgccat gaagatcagg taatgacgtt cctgatgatc     300
ctgccaattg ccttgttaac cgctggcttg ttaggcacgc tgtttgtggt gattaaaaaa     360
aaatactgta acgcctgacg atttttcccg ttcccggctg ctgtaccggg aacgtattta     420
attcccctgc atcgcccgca ttcttgccgc atcttccccc ggcgtcacac cgaagtaacg     480
tttaaactca cggctaaatt gcgatgcgct ttcatagccg acgcgcatcg ctgctgcgct     540
agccttcatg ccgtcatgga tgatcatcat ccgcgcctta tgcagacggt aattcttcaa     600
atactgcaac ggcgaggtgc tggtgacaga cttaaaatta tggtggaacg ccgatacgct     660
catgttggct tctgccgcca gttgctcgac gctcaggttt cggtgtatt tattctcaat     720 ccgtttcagc acgcggctaa tcagactgaa gtgagtctgg cgactgacca cgccagtaa     780 cgcgccgccg caaggtccgg tcagcacgta gtacagaatt cgcggatga tctgtttgcc     840 gagaatacgc gcatccagtg gtcgctccat cacgtcgagt aaccgctccg ccgcgcataa     900
aatctcttct gataacgtgg cggagttaat cccgctggct gccatcgacg gctggaaatg     960
ctcatcttcg ccaatgtcca tcaacagttc ctgtaactgc aaaatatcga cattgagacg    1020
caaccctgcc agcggcacct ctgacgtggc ataggtttcg cactcaaacg gcaacggcac    1080
cgtcagcagc aggtattcat tggcatcata acgaaacacg cgttcattga tataaccgat    1140
tttatgcccg aaaagagaa ttatgatgcc aggctctgat gaatccccta atgattttgg    1200
taaaaatcat taagttaagg tggatacaca tcttgtcata tgatcaaatg gtttcgcgaa    1260
```

-continued

```
aaatcaataa tcagacaaca agatgtgcga actcgatatt ttacacgact ctctttacca  1320
attctgcccc gaattacact taaaacgact caacagctta acgttggctt gccacgcatt  1380
acttgactgt aaaactctca ctcttaccga acttggccgt aacctgccaa ccaaagcgag  1440
aacaaaacat aacatcaaac gaatcgaccg attgttaggt aatcgtcacc tccacaaaga  1500
gcgactcgct gtataccgtt ggcatgctag ctttatctgt tcgggcaata cgatgcccat  1560
tgtacttgtt gactggtctg atattcgtga gcaaaaacga cttatggtat tgcgagcttc  1620
agtcgcacta cacggtcgtt ctgttactct ttatgagaaa gcgttcccgc tttcagagca  1680
atgttcaaag aaagctcatg accaatttct agccgacctt gcgagcattc taccgagtaa  1740
caccacaccg ctcattgtca gtgatgctgg ctttaaagtg ccatggtata aatccgttga  1800
gaagctgggt tggtactggt taagtcgagt aagaggaaaa gtacaatatg cagacctagg  1860
agcggaaaac tggaaaccta tcagcaactt acatgatatg tcatctagtc actcaaagac  1920
tttaggctat aagaggctga ctaaaagcaa tccaatctca tgccaaattc tattgtataa  1980
atctcgctct aaaggccgaa aaaatcagcg ctcgacacgg actcattgtc accacccgtc  2040
acctaaaatc tactcagcgt cggcaaagga gccatgggtt ctagcaacta acttacctgt  2100
tgaaattcga acacccaaac aacttgttaa tatctattcg aagcgaatgc agattgaaga  2160
aaccttccga gacttgaaaa gtcctgccta cggactaggc ctacgccata gccgaacgag  2220
cagctcagag cgttttgata tcatgctgct aatcgccctg atgcttcaac taacatgttg  2280
gcttgcgggc gttcatgctc agaaacaagg ttgggacaag cacttccagg ctaacacagt  2340
cagaaatcga aacgtactct caacagttcg cttaggcatg gaagttttgc ggcattctgg  2400
ctacacaata acaagggaag acttactcgt ggctgcaacc ctactagctc aaaatttatt  2460
cacacatggt tacgctttgg ggaaattatg aggggatctc tcagtgccag gctcgtacat  2520
caccggtgta cgtgcgaaag gcgtctcgcc atacaacaaa cgcacatcgg gcaacagttc  2580
tgacaaacta ttttctttaa ttttcagttt attaacttta tccgccagca agcggcaaat  2640
ctcttcacgt ttcatatcgc gtaatttctt aggaataatg cggcaatttg attgtgcgca  2700
attttgtagc atttctccag cactctggag gaataggcaa gacattggca gaaatgagca  2760
ttgagagcca gggcgctggc gatcacaatg aaaaacatca ggcagatcgt tctctgccct  2820
catattggcc cagcaaaggg agcaagtaat gaacaacttt aatctgcaca ccccaacccg  2880
cattctgttt ggtaaaggcg caatcgctgg tttacgcgaa caaattcctc acgatgctcg  2940
cgtattgatt acctacgtgt gcggcagcgt gaaaaaaacc ggcgttctcg atcaagttct  3000
ggatgccctg aaagggcatg ga                                          3022
```